(12) United States Patent
Rokutan et al.

(10) Patent No.: US 7,734,422 B2
(45) Date of Patent: Jun. 8, 2010

(54) METHOD FOR EVALUATING DNA PROBES POSITION ON SUBSTRATE

(75) Inventors: Kazuhito Rokutan, Osaka (JP); Hiroyuki Tomita, Tachikawa (JP); Toshiro Saito, Hatoyama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 768 days.

(21) Appl. No.: 11/113,195

(22) Filed: Apr. 25, 2005

(65) Prior Publication Data

US 2005/0208561 A1 Sep. 22, 2005

Related U.S. Application Data

(62) Division of application No. 10/083,550, filed on Feb. 27, 2002, now abandoned.

(30) Foreign Application Priority Data

Feb. 28, 2001 (JP) ............................. 2001-053465
Jan. 31, 2002 (JP) ............................. 2002-022682

(51) Int. Cl.
- *G01N 33/48* (2006.01)
- *G06F 19/00* (2006.01)
- *G01N 31/00* (2006.01)
- *C07H 21/00* (2006.01)
- *C07H 21/04* (2006.01)
- *C12Q 1/68* (2006.01)
- *C12P 19/34* (2006.01)
- *C12M 1/00* (2006.01)

(52) U.S. Cl. ............................. 702/19; 702/20; 702/22; 536/23.1; 536/25.3; 435/6; 435/91.2; 435/283.1

(58) Field of Classification Search ........................ None
See application file for complete search history.

(56) References Cited

U.S. PATENT DOCUMENTS 6,372,249 B1  4/2002  Smith et al.

FOREIGN PATENT DOCUMENTS

WO  WO 98/53103  5/1998

OTHER PUBLICATIONS

Alon et al. "Broad patterns of gene expression revealed by clustering analysis of tumor and normal colon tissues probed by oligonucleotide arrays" (1999) Proc. Natl. Acad. Sci. USA, vol. 96, pp. 6745-6750.*
Lipshutz et al., "High Density Synthetic Oligonucleotide Arrays", Nature Genetics Supplement, vol. 21, (Jan. 1999), pp. 20-24.
Renu A. Heller et al., "DNA Microarray", Chapter 10, (Sep. 25, 2000), pp. 191-206.
Renu A. Heller et al., "DNA Microarray", Translation into English of the legend of Fig. 10-1 on p. 192, Chapter 10, (Sep. 25, 2000).
Tor-Kristian Jenssen, Astrid Laegreid, Jan Komorowski and Eivind Hovig, "A Literature Network of Human Genes for High-Throughput Analysis of Gene Expression", Nature Genetics, vol. 28, May 2001, pp. 21-28.
Ioannis Xenarios, Danny W. Rice, Lukasz Salwinski, Marisa K. Baron, Edward M. Marcotte and David Eisenberg, "DIP: The Database of Interacting Proteins", Nucleic Acids Research, 2000, vol. 28, No. 1, pp. 289-291.
Ananthan J., Goldberg AL, Voellmy R., "Abnormal Proteins Serve as Eukaryotic Stress Signals and Trigger the Activation of Heat Shock Genes", National Library of Medicine, PubMed, Science Apr. 25, 1986; 232 (4749); 522-4, p. 522-524.
Dick D. Mosser, Antoine W. Caron, Lucie Bourget, Claude Denis-Larose and Bernard Massie, "Role of the Human Heat Shock Protein hsp70 in Protection against Stress-Induced Apoptosis", Molecular and Cellular Biology, Sep. 1997, vol. 17, No. 9, pp. 5317-5327.
Watson et al., Biol. Psychiatry, vol. 45, pp. 533-543, 1999.
Schena et al., Proceeding of the National Academy of Sciences, vol. 93, pp. 10614-10619, Oct. 1996.
Iyer et al., Science, vol. 283, pp. 83-87, 1999.

* cited by examiner

*Primary Examiner*—Eric S Dejong
(74) *Attorney, Agent, or Firm*—Stites & Harbison PLLC; Juan Carlos A. Marquez, Esq.

(57) ABSTRACT

An oligonucleotide array comprising an array of multiple oligonucleotides with different base sequences fixed onto known and separate positions on a support substrate, wherein said oligonucleotides are biological stress related genes or complementary sequence chains to the said genes, and the said oligonucleotides are classified according to their gene functions, wherein the fixation region on the support substrate is divided into the said classification.

8 Claims, 15 Drawing Sheets

ALIVE · INFLAMMATION · ANTI-INFLAMMATION · DEATH

FIG. 11

| | i | | 3 | 2 | 1 | |
|---|---|---|---|---|---|---|
| | $(i-1)^2+1$ | | 5 | 2 | 1 | 1 |
| | $(i-1)^2+2$ | | 6 | 3 | 4 | 2 |
| | $(i-1)^2+3$ | | 7 | 8 | 9 | 3 |
| | ↓ | | | | → | |
| | $(i-1)^2+j$ | → | $j^2-2$ | $j^2-1$ | $j^2$ | j |
| | | | | | | |

METHOD FOR EVALUATING DNA PROBES POSITION ON SUBSTRATE

This application is a Divisional of U.S. Ser. No. 10/083,550 filed Feb. 27, 2002 now abandoned. Priority is claimed based on U.S. Ser. No. 10/083,550 filed Feb. 27, 2002, which claims priority to Japanese Patent Application Nos. 2001-053465 and 2002-022682 filed on Feb. 28, 2001 and Jan. 31, 2002, respectively.

BACKGROUND OF THE INVENTION (1) Field of the Invention

This Invention concerns a DNA array and an analytical method of stress using said DNA array for the simple evaluation of degrees of stress. This Invention also concerns a method of evaluation of expression of gene groups related to certain diseases, not limiting to stress, by positioning oligonucleotides on substrate based on degree of correlation.

(2) Description of the Related Art

Increases in diseases associated with life style and atopic allergy are one of the factors that are responsible for the increase in today's medical burden to the nation. Reported also are increases in the numbers of suicides, lowering age of criminals and increases in patients with post-traumatic stress disorder (PTSD). Medical experts agree that stress play a role in background or life style-associated diseases, allergy, suicide, crime and PTSD.

Stress is defined as a reaction of the living body to sudden invasion, both as specific reaction to each invasion and as generic non-specific reaction, which has a fixed pattern regardless of the type of invasion. Stress-causing stimuli, or stressor, include abnormal temperature, burn, inflammation, immune reaction, noise, electric shock, ultraviolet light, bacterial toxin, bacteria, virus, operation, exercise, pain stimulus, physical restrain, hypoxia, hypoglycemia, ischemia, tests, interpersonal friction, deaths of relatives, loneliness, broken heart, despair, disappointment, social unrest, war, terrorism and earth quake. With advancement in knowledge of the maintenance mechanism of bodily homeostasis, it has become clear that there is a close relationship between abnormalities of the three major regulatory mechanisms of the body, the nerve, endocrine and immune system, and stress.

In conventional oligonucleotide array, it is decided first which genes are placed on chips, and then, according to the order, such as alphabetical order, designated to genes, genes are placed on a plate, such as a 96-well plate, using a spotter with several needles. In this method, although genes are lined up systematically, a step is required at the actual evaluation to confirm the positions of genes by consulting address information on files and images that show where and which genes are placed.

However, no medicophysiological diagnostic method has been developed by which the degree of stress can be evaluated objectively. For instance, blood concentrations of stress hormones, such as catecholamine and adrenocortical hormone, vary greatly among individuals and change with time. In other words, blood concentrations of stress hormones do not change uniformly in response to stress stimuli, and are known to be insufficient to be used for evaluation of degree of stress. In addition, it is extremely difficult to evaluate bodily reactions only by measuring these limited stress hormones because stress is the reaction of complex systems, requiring multilateral evaluations. Stress also is studied in the field of social psychology. Psychological tests in the form of interviews or questionnaires have been developed to evaluate degree of stress. However, it cannot be said that psychological tests substantiate sufficiently physiological reaction of the body. That is to say, currently, there scarcely are methods for objective evaluation of stress of individual persons. However, stress is an important phenomenon that is related to abnormalities of the automatic nervous system, endocrine and immune, gastric ulcer, acute lesions of gastric mucus, mental diseases and reproductive dysfunction. If it is possible to evaluate degree of stress readily at not only specialty medical organizations but also general-practitioners, health facilities at business and school and health screening centers, it is a useful measure, as feedback can be implemented in daily life at home, workplace and school. From that standpoint, development of diagnostic instruments is sought that can determine the degree of stress.

The objective of this Invention is to provide a diagnostic method, specifically, oligonucleotide array, by which degrees of stress can be determined readily and at low cost. In particular, this Invention aims at minimizing the number of DNA fragments placed on the array by specifying groups of genes, which are imperative in determination of degrees of stress, and at providing an array for stress analysis with high reproducibility and reliability. This Invention also aims at instant evaluation of the correlation between genes that are related a certain disease by devising regulations in how genes are arranged.

SUMMARY OF THE INVENTION

As mentioned above, stress is the complex reaction in which various organs, such as the nervous, endocrine and immune systems, play roles and must be evaluated from many angles. Expressed at the gene level, stress reaction, which is a phenomenon with complex sources, occurs when the on-and-off switches of groups of genes related to stress are turned on, the volume of stress-related protein increases or decreases. The body mechanism is thought to be regulated according to the balance in activities of the whole protein. In other words, abnormalities of the on-and-off mechanism in stress-related gene groups induce the abnormalities of the balance in protein activities, resulting in the abnormalities of regulation of body mechanism, or occurrence of stress. The switching on and off of genes is controlled, for example, by increases or decreases in the level of gene expression. The level of gene expression can be measured using the level of messenger RNA or the level of protein as an index. With techniques currently available, the measurement can be performed extremely easily using the level of messenger RNA as an index rather than using the level of protein. Therefore, stress is evaluated easily by observing the increase or decrease in the level of expression of messenger RNA of several stress-related genes. DNA array (also called oligonucleotide array) developed recently is the most suitable for this purpose.

Here, the state of expression is explained in detail. The state of expression is one of genotype, and expression in the term "the state of expression" means the state, where the region of genes on DNA is transcribed on to RNA, or protein is translated through transcribed RNA. The state in the term "the state of expression" means a row of "n" pieces of genes, or gene 1, gene 2, so forth, ending with gene "n". When ON indicates that expression takes place and OFF indicated that expression does not take place, there is a row of (ON or OFF), (ON or OFF), repeating "n" times; this is called "state". When with "n" pieces of genes, UP indicates increased level of RNA transcription, EVEN indicate unchanged, and DOWN indicates decreased, there is a row of (UP, EVEN or DOWN), (UP, EVEN or DOWN), repeating "n" times; this is called "state". The correlation between 2 genes, any 2 among "n" pieces of genes, is "state", that is to say, when the intensity of measurement signal of gene i is X and the intensity of measurement signal of gene j is Y, and mean of X and Y in N times of experiments are m(X) and m(Y), and standard deviations are S(X) and S(Y), respectively, the matrix of the correlation coefficient "r", or r(i,j) is "state". Correlation coefficient can be expressed, for example, in the following equation (1).

$$r(i, j) = \sum_{k=1}^{N} (X - m(X))/S(X) \times (Y - m(Y))/S(Y) \Big/ (N - 1) \quad (1)$$

Changes in the above-mentioned the state expression, that is, changes in genotype induce changes in phenotype. Phenotype means phenomenon that can be observed from outside by some means. Phenotype, for example is disease or symptoms and sites of the body where symptoms appear. Disease is a pathophysiological state that physicians can diagnose by experience, such as diabetes mellitus and cancer. Symptom is a phenomenon persons feel subjectively, such as headache and abdominal pain. Symptom also is different from normal values that can be detected by test apparatus; for example, neutral fat is above the standard value in obesity. Included also in phenotype are some things that can be observed from outside by some means, excluding difference in cell configuration and in velocity of cell growth.

DNA array (oligonucleotide array) comprises plural DNA fragments (oligonucleotide) that are fixed on substrate. Each nucleotide corresponds to different genes. In measurement, complementary DNA (cDNA) fragments are synthesized in reaction with reverse transcriptase using messenger RNA as a template. At the time of the reaction with reverse transcriptase, an appropriate label binds with cDNA fragments or is incorporated when a strand is extended for labeling of cDNA (hereinafter, such cDNA is called labeled cDNA). Complementary binding takes place between oligonucleotide fixed on substrate and labeled cDNA fragments. Coordinates on substrate on which oligonucleotide are fixed, all differ. If it is known beforehand which oligonucleotide is fixed on which coordinates, increases or decreases in messenger RNA can be measured simultaneously in plural numbers of genes.

In order to achieve the objective that degree of stress is evaluated using oligonucleotide, this Inventors investigated and found that it is necessary to place on the same array many genes, or at least 30 or more different genes, and more desirably several hundred DNA fragments (oligonucleotide fragments; probe DNA). Those genes are; (1) internal; and external standard genes for proofreading (housekeeping genes), (2) stress-related genes such as heat shock protein (HSP) and hormone genes such as sex hormone that decreases under stress, (3) cytokine genes that induce immune response and inflammatory reaction, (4) genes that induce cell death, (5) genes related to anti-inflammation and wound healing, and genes related to cell growth inhibition, such as glucocorticoid, TGFβ and FGF, (6) transcription factor and signaling molecules related to immune response, (7) transcription factor and signaling molecules related to induction of cytokine, which causes cell injury, (8) transcription factor and signaling molecules related to growth inhibition, and (9) transcription factor and signaling molecules related to stress response. The above (1) to (5) are functional genes that govern specific functions in the body, and (6) to (9) are signal transfer genes that govern transmission of signals between functional genes.

This Inventors also found that by positioning DNA probes that are to be fixed on substrate according to gene classification of the above (1) to (9), results of measurement of DNA array can be understood and evaluated immediately. In addition, this Inventors found that by using leukocytes that are relatively easily collected from subjects, for whom messenger RNA is tested, as specimens for tests, degrees of stress can be easily evaluated. Thus, this Invention was completed. Concrete means to solve problems are explained below.

This Invention is an array on which plural oligonucleotides with different base sequences are fixed at known, different positions on a support medium, and the oligonucleotide array is characterized by the fact that the said oligonucleotides are those of genes mentioned in the above (1) to (9) or strands of complementary sequences on the said genes, and the base sequence of said oligonucleotides comprises bases that number at least 20 or more.

An oligonucleotide array of this Invention also is characterized by the fact that nucleotides are those of genes related to mediating factors that intermediate 3 parties of the endocrine, immune and nervous systems that are known to work in coordination in stress reaction, or those of strands of complementary sequences, and the base sequence of said oligonucleotides comprises bases numbering at least 20 or more. Examples of said mediating factors include corticotropin releasing hormone (CRH) and cytokine.

In addition, an oligonucleotide array of this Invention is characterized by the fact that oligonucleotides fixed on the same support medium have the base sequence comprising bases that number at least 20 or more, and consist of gene groups related to 2 or more different signal transfer pathways or strand groups of complementary sequences on said gene groups. Said gene groups comprise at least 2 or more types of genes that code intracellular signal transfer related protein groups that lie between cell membrane receptors and intranuclear receptors and transcription factors that are on the same signal transfer pathway.

Furthermore, this Invention is a gene expression analytical method using two oligonucleotide arrays. Using the first oligonucleotide array with plural oligonucleotides with different base sequences that are fixed on a support medium, gene expression analysis is conducted comprehensively to select gene groups that show changes in the level of expression and gene groups related to said gene groups. The second oligonucleotide array is made of oligonucleotides of the above selected gene groups, related gene groups and strands of complementary sequences on said selected gene groups and related gene groups. Said oligonucleotides have the base sequence comprising bases that number 20 or more and are fixed on a support medium. Said second oligonucleotide array also is used for gene expression analysis.

This invention was completed using the investigation results on stress response mentioned above. By using the oligonucleotide array of this invention, it is possible to easily evaluate the degree of disorder, malfunction, symptom (stress) judging from not only each gene but also focusing on the change of balance among the nervous system, endocrine system and immune system. Particularly, by arranging each gene on the substrate while taking into account two axes such as "life and death" and "inflammation and anti-inflammation", intuitive evaluation of the results is possible. Also, since the oligonucleotide probes on the array of this invention are narrowed down to those that have a deep relationship with stress response, the number of oligonucleotide types to be used as probes for the array are greatly reduced, thus allowing to reduce the price. Furthermore, by fixing a single type of oligonucleotide in several positions as a probe, the signal intensity of multiple positions can be averaged to increase reliability. Also, by making a rule for arranging the gene groups, relationships between genes related to a certain disorder can be evaluated at a glance.

Other objects, features and advantages of the invention will become apparent from the following description of the embodiments of the invention taken in conjunction with the accompanying drawings.

BRIEF DESCRIPTION OF THE DRAWINGS

FIG. 11 illustrates an example of positioning rule.

In the drawings, numerals represent the following:

1. Substrate, 2. Probe DNA fixation region, 11. Probe DNA of housekeeping genes, 12. Probe DNA of stress-tolerance and survival-related genes and hormones, 13. Probe DNA of inflammation-, immune response-, and cell proliferation-related genes, 14. Probe DNA of apoptosis and cell death-inducing genes, 15. Probe DNA of gene related to anti-inflammation, wound-healing, and cell growth inhibition, 16. Probe DNA of immune response related transcription factors and signaling molecules, 17. Probe DNA of cytokine inductive transcription factors and signaling molecules, 18. Probe DNA of cell growth inhibition related transcription factors and signaling molecules, 19. Probe DNA of stress response related transcription factors and signaling molecules, 20. Fluorescence detector, 21. DNA probe, 22. Fluorescence labeled gene, 23. Supporter, 24. Example of probe positioning according to expression pattern, 25. Gene, 26. Correlation score, 27. Gene, 28. Inter-gene pass way, 29. Reagent, 30. Spotter, 31. Computer for controlling the spotter, 32. Chip (being made), 33. Chip (finished), 34. Fluorescence detector, 35. Computer for controlling the fluorescence detector, 36. Positioning information file, 37. Public database, 38. In-house database, 39. Network connected computer, 40. Probe stock, 41. Automatic dispenser, 42. Probe to be spotted, 46. Experimental results, 47. Computer for experimental data analysis.

PREFERRED EMBODIMENT OF THE INVENTION

Figure 4:
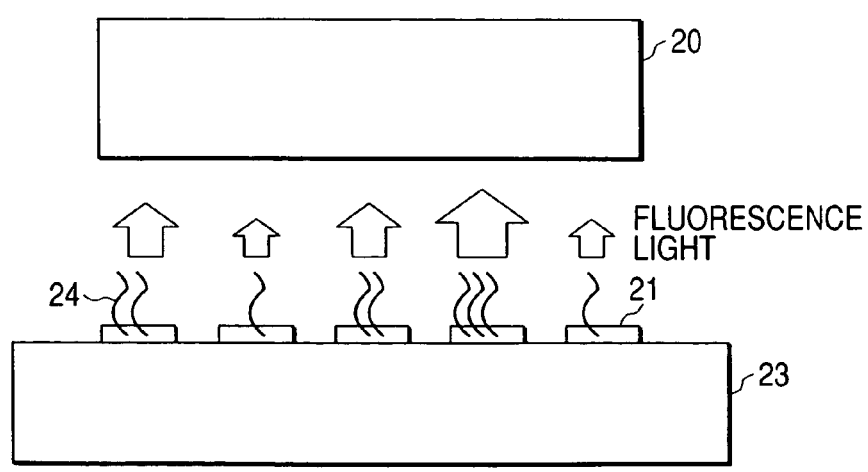
FIG. 4 illustrates an example of general structure of DNA chip.
Figure 14:
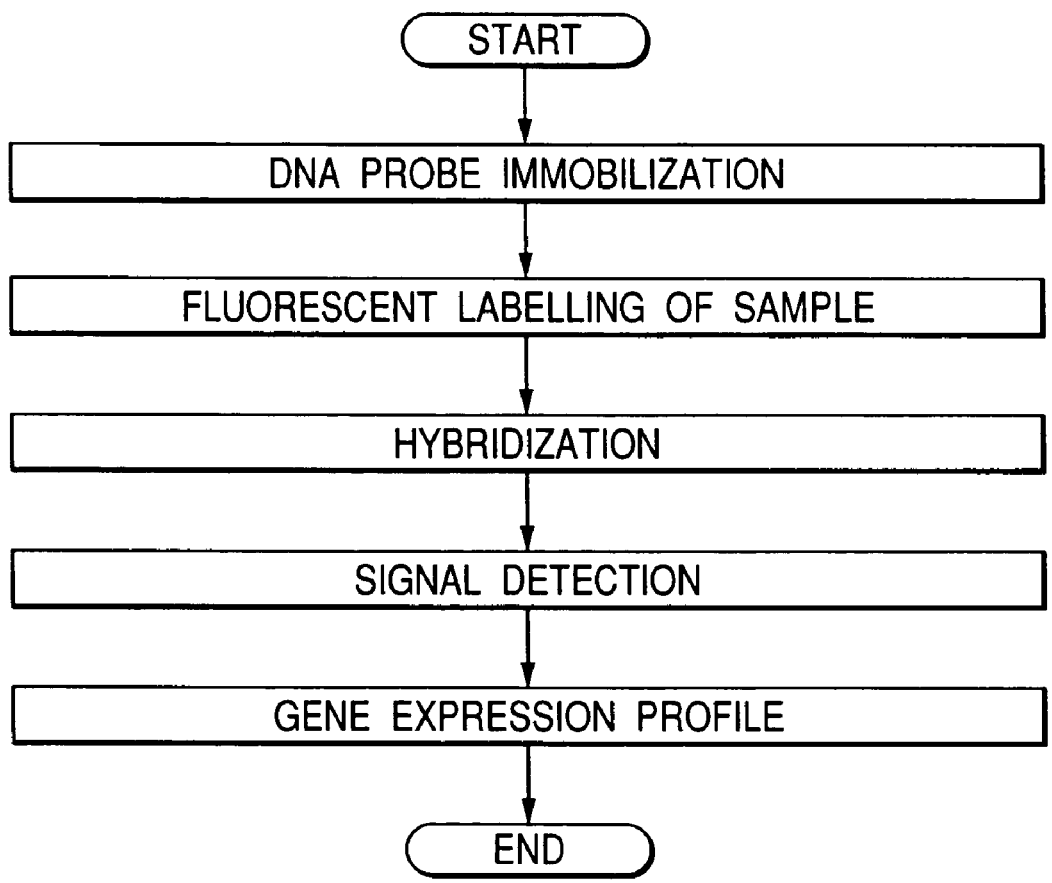
FIG. 14 illustrates a flow chart of measurement using DNA chip.

FIG. 4 illustrates a general structure of DNA chip. FIG. 14 illustrates a flow chart of measurement using DNA chip. First, DNA probes (21) are fixed on to a support medium (23). Gene fragments extracted from samples obtained from subjects of measurement are labeled with fluorescent label, etc. The fluorescent-labeled gene (22) and DNA probes (21) are hybridized. Then, fluorescence light originated from fluorescent label is detected by a detector (20). Detection demonstrates the level of fluorescent-labeled gene (22) that were hybridized with each of DNA probes (21). This is called gene expression profile.

Oligonucleotide, that is, DNA probe, is classified according to P value, FDD and SVD. The P value is a value called in statistics as significant probability, which expresses degrees of dissociation of statistics from null hypothesis in hypothesis testing. The P value is expressed between 0 and 1. The smaller the figure is the larger the dissociation is. The null hypothesis in the Specification of this application is defined as "there is no difference in the level of expression between gene A originating RNA and gene B originating RNA." When P is 0, it means that gene A originating RNA differs from gene B originating RNA, and when P is 1, it means that gene A originating RNA is the same as gene B originating RNA. The P value can be obtained in, for example, parametric tests such as t-test and F-test or non-parametric tests such as Wilcoxon test.

Differential display is one of methods of detecting the difference in messenger RNA that expresses in cells under different conditions. The principle of the method is that messenger RNA that is reverse transcribed using oligo dT primer is combined with various primers. The combinations are amplified in PCR for comparison of band patterns in electrophoresis in each sample. When fluorescent labeling is used for signal detection, it is called fluorescent differential display (FDD). Messenger RNA that expresses can be either known or unknown.

Support vector machine (SVM) is a method based on machine learning used for classification of hand-written letters and images, and one of methods used to classify given data into plural categories. SVM is an algorithm with which differences among messenger RNA expressing in cells under different conditions are classified. Thus, SVM is an algorithm of classification that belongs to supervised methods. Similar methods include nearest neighbor, discriminant analysis, neural network and classification tree boosting bagging. Although the Specification of this application mentions SMV as the typical example, any classification methods can be used.

For example in order to evaluate degrees of stress, it is necessary to conduct highly accurate analysis of the mechanism of function of stress response. It is clearly avoided that DNA fragments that should have complementary binding with one kind of genes bind with other genes (cross hybridization). It becomes progressively difficult, as the number of genes that are fixed on a piece of array increases. Consequently, it is extremely difficult to eliminate completely cross hybridization among five-thousands to several ten-thousand genes on one DNA-array for detection. It became clear in investigation on sequence homology based on blast algorithm that when the base length of DNA fragments used as probes is not more than 1,000 bases, it is desirable to place less than 1,000 to 1,500 kinds of genes on one array. Therefore, if the purpose of use of DNA array is to elucidate the mechanism of action of stress response, it is desirable to collect the least possible number of genes that are related to the mechanism of action of stress response and use only these genes for array. It is not desirable to place on array genes that are not related to stress response, which will result in increases in cost of making probes, leading to eventual increases in cost of oligonucleotides. In this Invention, the number of kinds of oligonucleotides used as probes on array can be restricted, any one kind of oligonucleotides can be fixed as probes at plural positions. Signal intensity can be obtained from plural positions, increasing reliability.

Concrete examples of positioning methods of gene groups are explained below.

1. Positioning Methods of Gene Groups Using Bioinformatics.

1) According to Gene Functions (Classification No. 1)

Figure 1:
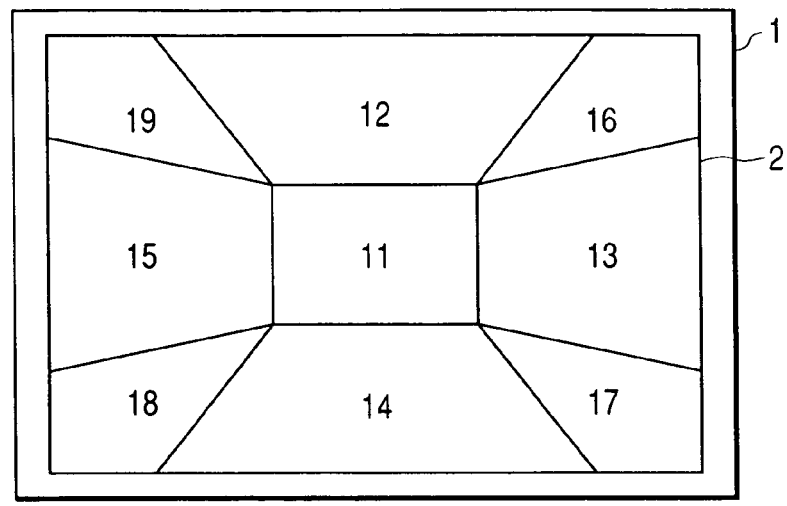
FIG. 1 illustrates DNA probe position on substrate (Example 1).
Figure 2:
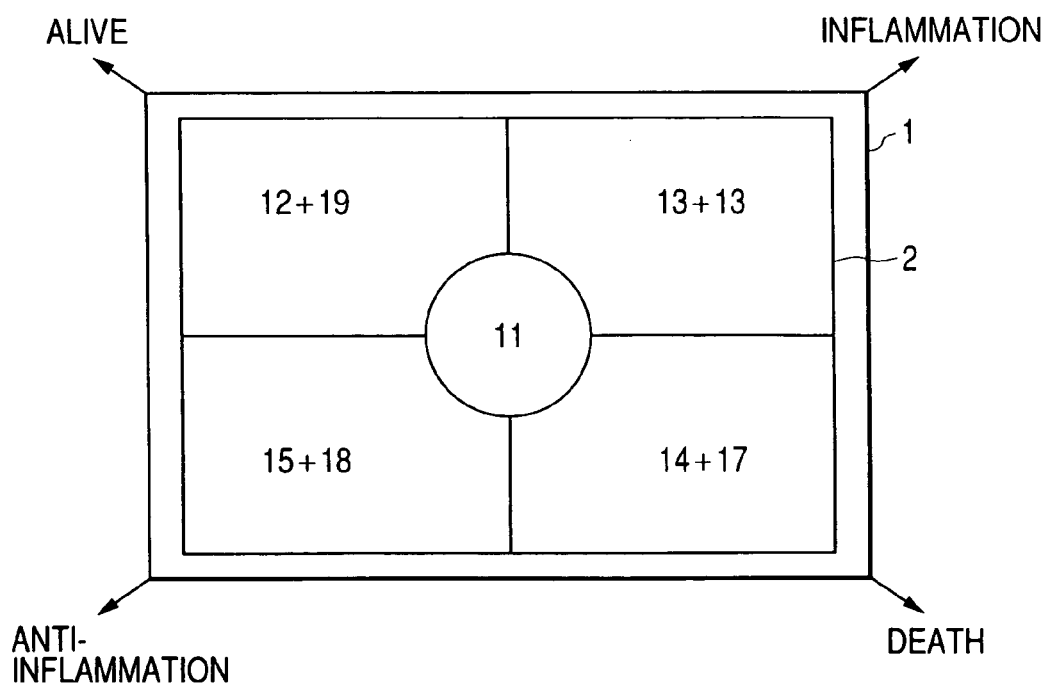
FIG. 2 illustrates DNA probe position on substrate (Example 2).

For example, gene groups are positioned as shown in FIGS. 1 and 2 in the Specification of this application. No. 11 indicates internal and external standard genes for proofreading (housekeeping genes), No. 12 stress and survival related genes and hormone genes, No. 13 inflammation, immune response, cell proliferation related genes, No. 14 apoptosis and cell death related genes, No. 15 anti-inflammation, wound-healing, cell growth inhibition related genes, No. 16 immune response related transcription factor signaling molecules, No. 17 cytokine inductive transcription factor, signaling molecules, No. 18 cell growth inhibition related transcription factor, signaling molecules, and No. 19 stress response related transcription factor, signaling molecules. FIG. 1 illustrates an example in which the above 11 to 19 are positioned at 9 fixed regions. FIG. 2 illustrates an example in which 11, 12 and 19, 13 and 16, 14 and 17, and 15 and 18 are positioned at 5 fixed regions.

Classification of genes into any among 11 to 19 is decided based on terminology defined in the ontology database constructed by the International Ontology Consortium. Gene related ontology can be searched on PubGene, which is one of publicly offered ontology database, or Gene Ontology (GO). The PubGene database connects gene with ontology through textual analysis of Medline, OMIM, etc. (refer to Tor-Kristian Jenssen et al. A literature network of human genes for high-throughput analysis of gene expression. Nature Genetics, vol. 28, pp21-28). In PubGene classification, HSPA1A, for example, which is a heat shock protein (HSP), is closely associated with Heat shock protein (GO No. 0003773) in the Functional Annotation and with transcription (GO No. 006350) and immune response (GO No. 0006955) in the Cell Process Annotation. Another HSP, HSPA1B, is classified to Heat shock protein (GO No. 0003773) in the Functional Annotation and apoptosis (GO No. 0006915) in the Cell Process Annotation. Therefore, according to the Functional Annotation in PubGene, for example, Both HSPA1A and HSPA1B belong to the same stress related gene, that is, heat stress protein. The two are classified to No. 12 Stress and survival-related genes and hormone genes. According to the Cell Process Annotation in PubGene, on the other hand, HSPA1A belongs to No. 13 Immune response related genes, and HSPA1B to No. 14 Apoptosis and cell death related genes. Ontology in the Functional Annotation and Cell Process Annotation in PubGene is listed in the order of scores. Therefore, ontology with the largest score or several numbers of ontology with relatively large scores are selected for classification. Along with PubGene, any tool or database can be used to search ontology based on gene names.

2) Gene Positioning within Fixation Regions (Classification No. 2)

The final positioning of genes that are distributed on fixation regions in the above 1) is decided according to any one or the combination of two or more of the following information; (1) gene correlation scores obtained through database, (2) information on pairing of ligand and receptor, (3) information on protein-protein interaction, and (4) information on gene pathway. The list of genes contained at each fixation region is obtained in Classification No. 1. Genes on the list are sorted out in the order of gene names (or gene symbol names) or put in order impromptu. For example, gene A on the top of list is fixed at the pre-determined position, such as at the corner or center of its fixation region. Then, genes that have strong correlation with gene A are sought. Supposing that gene B and gene C have strong correlation with gene A, then these two genes are positioned next to gene A. Gene B and gene C whose positions have been decided are eliminated from the list. Gene D, which is now at the top of the list, is positioned where genes A, B and C are not positioned. In the same manner as above, Gene E and gene F that have strong correlation with gene D are sought and positioned next to gene D. By repeating the process, genes with strong correlation with each other gather closely and form clusters within each fixation region. Methods of how to search for genes with strong correlations with each other are explained below.

Figure 7:
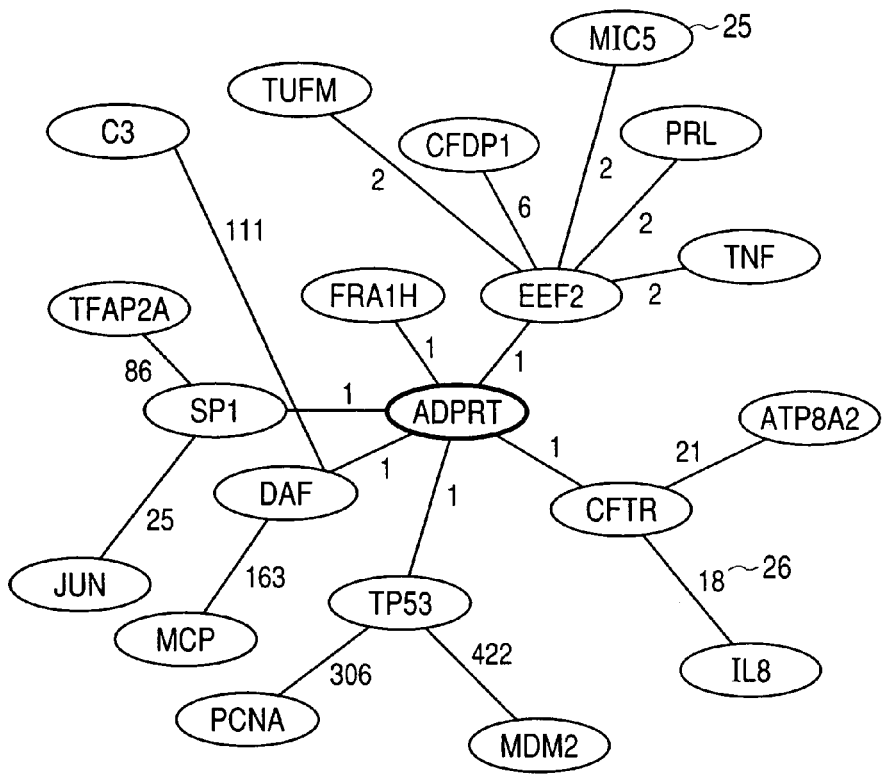
FIG. 7 illustrates an example of correlation score of genes.

In the method (1) above, it is regarded that the more frequently the two genes appear in the same sentence of the same database, the stronger the correlation between two genes is. The correlation score can be obtained, for example, by looking up PubGene database (refer to Tor-Kristian Jenssen et al. A Nature Genetics. Vol. 28, pp21-28.). FIG. 7 illustrates an example. Circles in FIGURE indicate genes, lines connecting circles the presence of correlation between genes, and numbers along lines the correlation scores. The correlation scores in FIG. 7 indicate the frequencies in which two genes connected with a line are mentioned in the same abstract in MEDLINE. Six genes that have strong correlations with ADPRT at the center of FIG. 7 are TP53, CFTR, EEF2, FRA1H, SP1 and ADF. Every one of 6 genes has a correlation score 1. When plural genes have the same correlation scores, genes are sorted, for example, in the alphabetical order and positioned around ADPRT accordingly. When the correlation scores differ, genes are positioned in the order of higher scores. The database used in PubGene is MEDILINE and OMIM by the American NCBI. Database in other references can also be used.

Positioning based on the above (2) information on pairing of ligand and receptor means that genes which proteins have a relationship of ligand and receptor are positioned adjacent to each other, for example insulin-like growth factor 1 (IGF1) and insulin-like growth factor 1 receptor (IGF1R) or insulin (INS) and insulin receptor (INSR) are positioned adjacent to each other.

Positioning based on the above (3) information on protein-protein interaction means that positioning of genes are decided according to protein interaction databases such as, for example, UCLA DIP (Database of Interacting Proteins by University California Los Angeles, USA, refer to I.Xenarios et al. DIP: the database of interacting proteins. Nucleic Acid Research. Vol. 28, pp. 289-291, 2000). In database of interacting proteins, proteins that interact each other are connected with lines as illustrated in FIG. 7. The intensity of interaction can be based on bonding strength of molecules, which can be indicated with, for example, dissociation constant obtained in experiments. The higher the bonding strength is, the greater the interaction intensity is. In addition, the interaction intensity that is confirmed in plural, or more than 2, experiments can be regarded stronger than that confirmed in just 1 experiment. Database of protein interaction other than DIP can be used.

Figure 8:
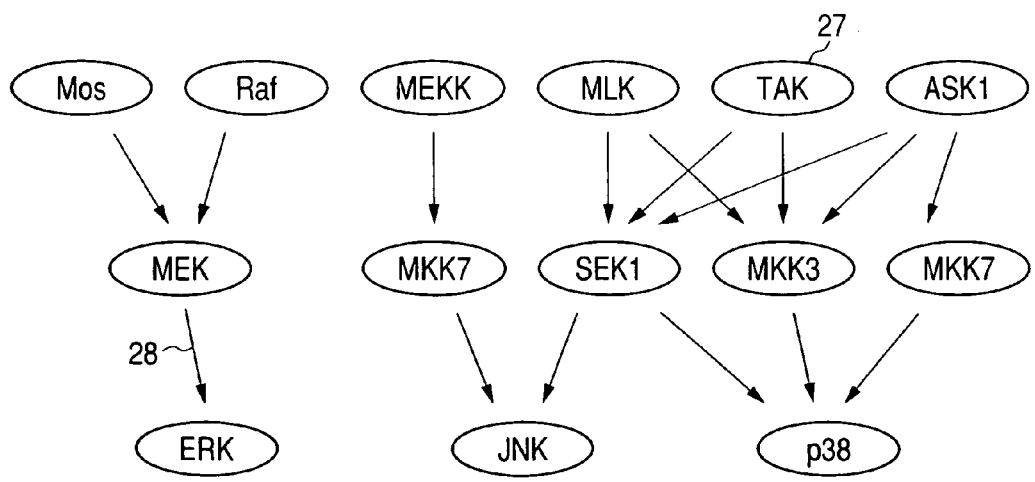
FIG. 8 illustrates an example of intergenic pathway.

Positioning based on the above (4) information on gene pathway means that genes related to intracellular and intercellular information transfer are positioned according to correlations in pathway. FIG. 8 illustrates the typical pathway, that is, MAPK (mitogen activated protein kinase) pathway. Circles indicate genes, and arrows connecting genes indicated the directions of information transfer between genes. For example, positioning of MEK gene adjacent to Mos gene and positioning Raf gene and ERK gene adjacent to MEK gene demonstrate that these genes belong to the same pathway and genes that transfer information directly are positioned close to each other. Other pathway information, for example, Pathway database, can also be used. Gene positioning can also be reflected on compiled information related to gene relationship, such as metabolic pathway database KEGG.

In this application, gene positioning on substrate on which DNA chips are fixed can be decided according to gene functions (Classification No. 1) using ontology in PubGene database, and gene positioning within fixation regions (Classification No. 2) can be decided based on gene correlations obtainable by searching PubGene database. However, the contents of PubGene database change, as information contained in literatures keeps increasing yearly. Consequently, gene correlation scores are expected to change, every time new findings appear. Accordingly, gene positionings on the fixation substrate have to change based on the content of information in literature. The positioning of DNA chips on the fixation substrate can be decided using, aside from PubGene, any or the combination of the following; gene interaction database based on experimental results, such as the above DIP, signal transfer pathway database, and metabolic pathway database. Furthermore, database describing gene interaction that will be newly constructed in the future.

Figure 15:
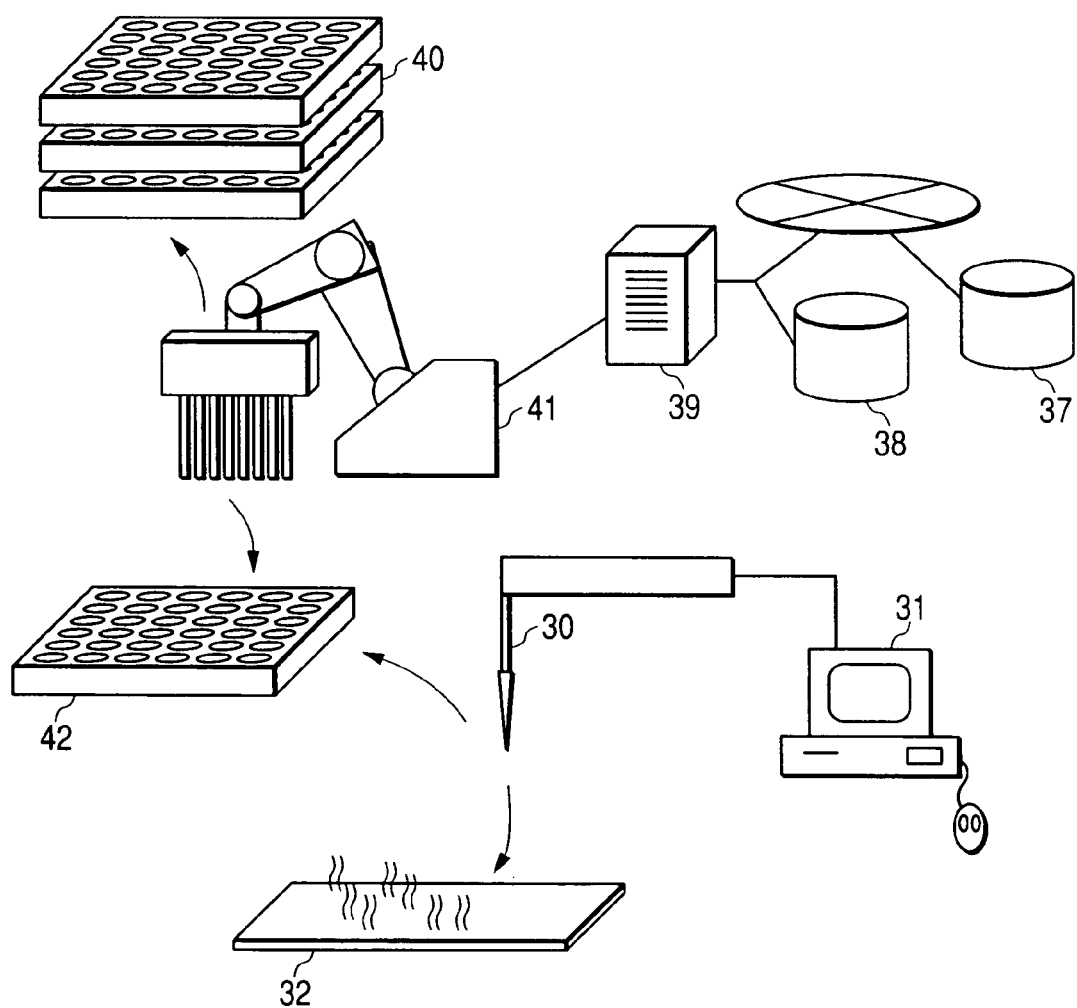
FIG. 15 illustrates an outline of DNA chip making using gene positioning in Bioinformatics.
Figure 16:
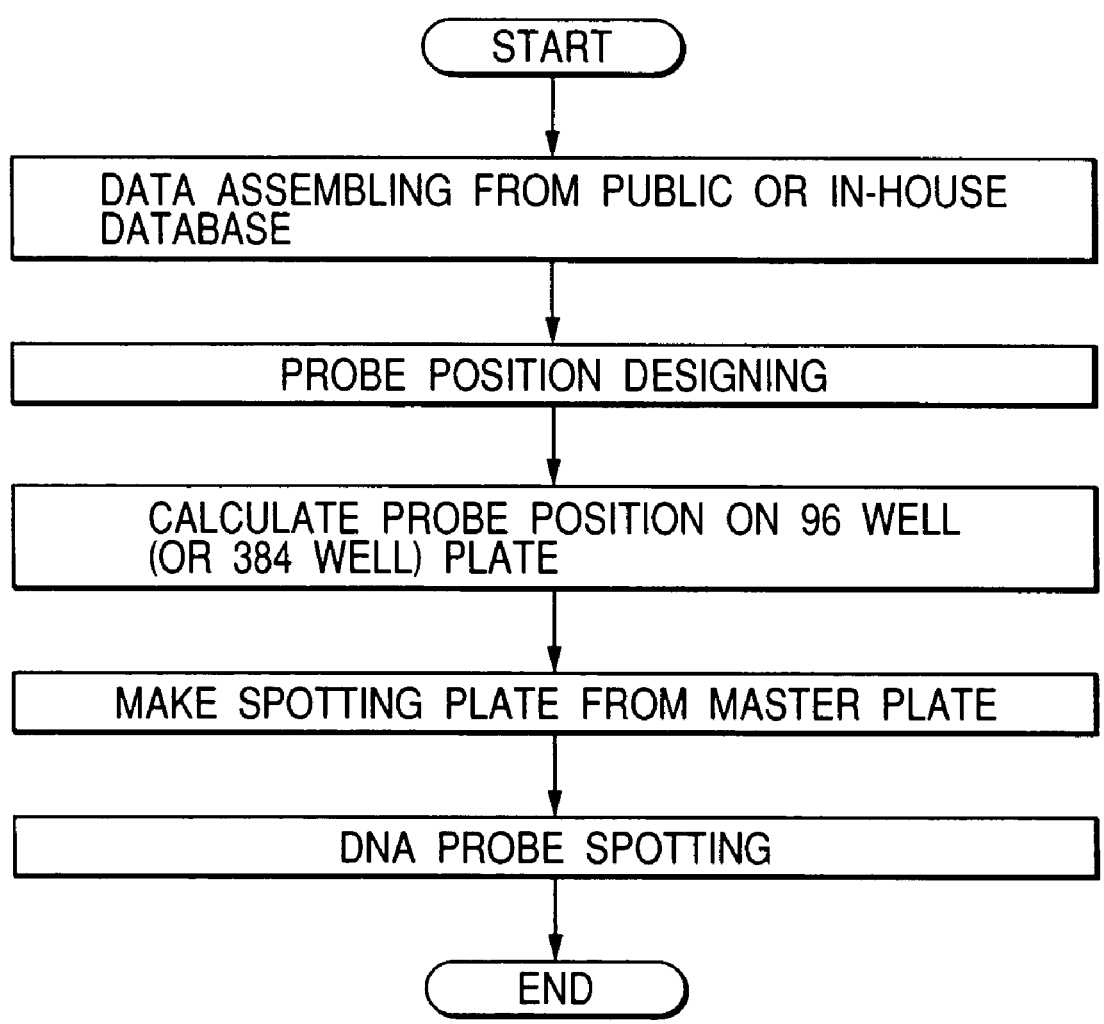
FIG. 16 illustrates a flow chart of DNA chip making using gene positioning in Bioinformatics.

FIG. 15 illustrates an outline of DNA chip making using gene positioning in Bioinformatics. FIG. 16 is a flow chart of the above. First, gene information is obtained from public database (37) through networking such as Internet or in-house database (38). Using methods published in this Specification based on obtained gene information, positioning of DNA probes (21) on the support medium (23) is decided. Positioning is processed, for example, by a computer (39) connected to networking. Positioning of DNA probes (21) on the support medium (23) is carried out, for example, using a spotter (30). The positioning of DNA probes (21) on a 96- or 384-well plate (42) that houses DNA probes for spotting is calculated backwards based on performance rules of the spotter (30) so that the previously decided positioning of DNA probes (21) on the support medium (23) is realized. If DNA probes are stocked in other plates (40), the DNA probes are transferred to the above plate (42) using a subdividing robot (41). The subdivision on the plate (42) using a robot (41) is carried out to meet the positioning of probes for spotting that is calculated to realize the previously decided positioning of probes is realized on the support medium. Finally, using the spotter (30), DNA probes (21) housed in the plate (42) are spotted on the support medium (23) to make DNA chips.

2. Positioning Methods of Gene Groups Based on Experimental Data

The above 1, demonstrates concrete examples of gene positioning on DNA chip fixation substrate using Bioinformatics and not based on experimental data. In this paragraph, gene positioning methods are described based on experimental data.

1) Data Assembling by Chips or FDD

First, 2 kinds of specimens are collected for comparison, and RNA is extracted from each specimen. Two kinds of specimens for comparison consist of, for example, specimens from patients with some disease and those from healthy persons. Specimens can be any of tissues, blood and cells that contain RNA. It is desirable for the consideration of individual differences to collect plural numbers of specimens, or as many as possible, from both patients and healthy persons. Gene expression in specimens from both subjects is analyzed using DNA chips or FDD. The DNA chip can be, for example, cDNA chips that uses as a probe the PCR-amplified DNA fragments using cDNA clone as template, or can be oligo chips that are used by Aphimetrics Co. in the USA. It is desirable to have gene probes of DNA chips as many as possible for the utmost analysis of the state of gene expression. For example, human genes are thought to number 30,000 to 40,000 and the transcription products to total approximately 100,000 including alternative splicings. Therefore, it is ideal to use DNA chips loaded with several tens of thousands of gene probes. If it is not possible to use DNA chips with a large number of gene probes, the state of gene expression can be analyzed, for example, in transcription products using FDD.

Figure 17:
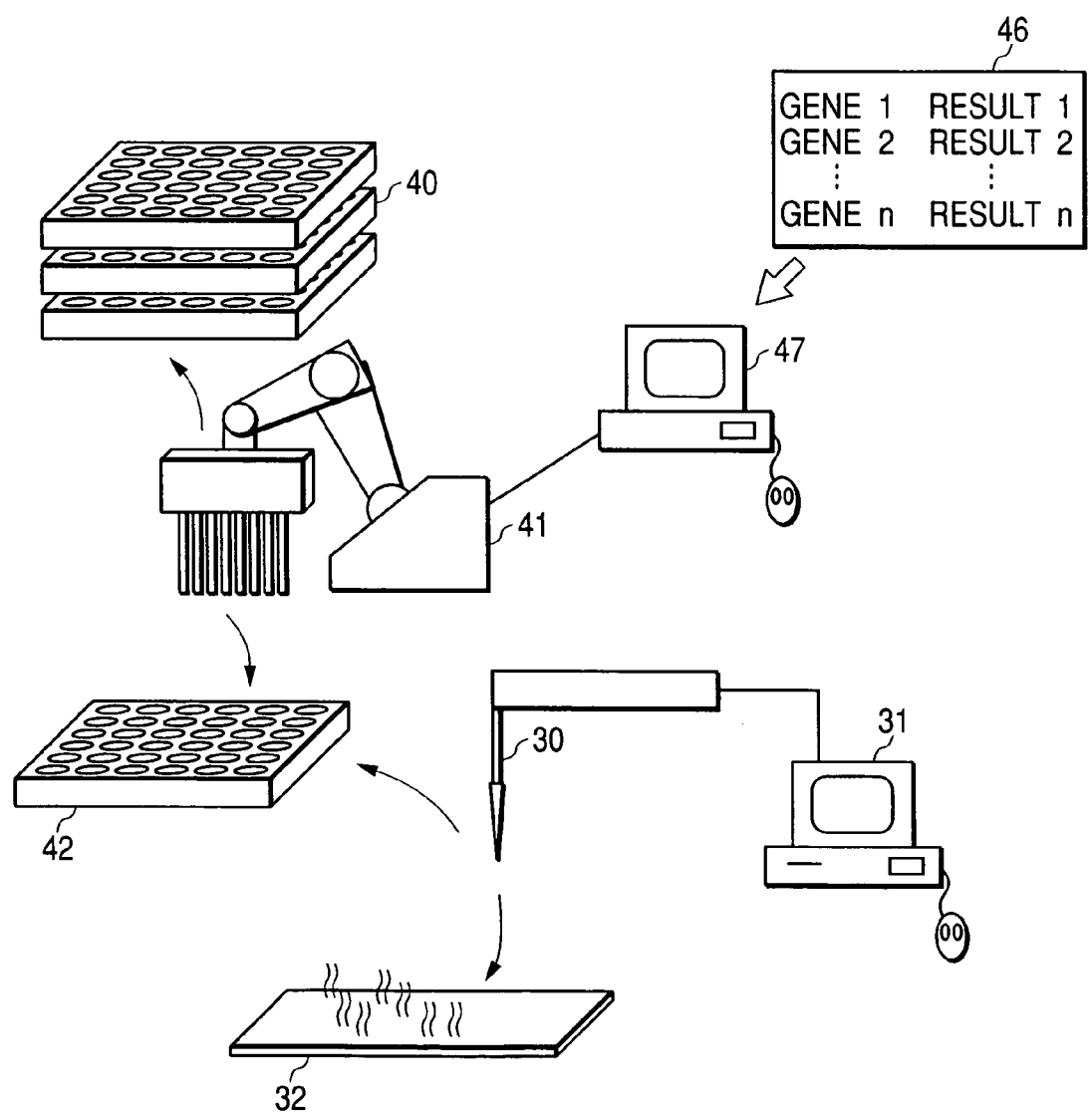
FIG. 17 illustrates an outline of DNA chip making using gene groups positioning based on experimental results.
Figure 18:
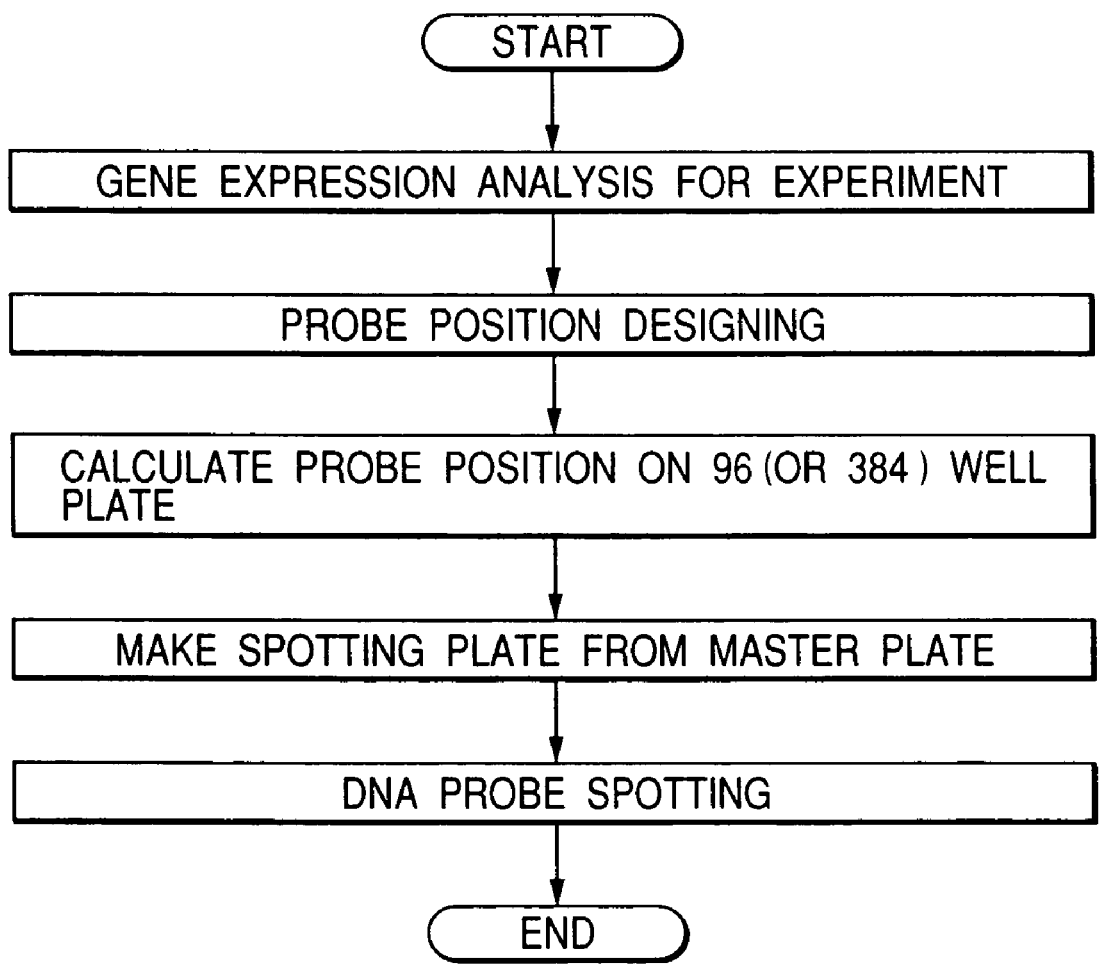
FIG. 18 illustrates a flow chart of DNA chip making using gene groups positioning based on experimental results.

FIG. 17 illustrate an outline of DNA chip making using gene positioning based on experimental data. FIG. 18 is a flow chart of FIG. 17. First, experimental data are assembled in FDD method or DNA chip method, and then, analyzed by a computer (47) to obtain gene information. Based on the obtained gene information, the positioning of DNA probes (21) on the support medium (23) is decided using the published methods in the Specification of this application. Processes following decision of the positioning are the same as those in DNA chip making using Bioinformatics illustrated in FIGS. 15 and 16.

2) Gene Positioning Based on Statistical Analysis

This paragraph describes methods of positioning of DNA chips on the fixation substrate in the Specification of this application, which are based on the results of measurement of the state of expression in 2 kinds of comparable specimens using DNA chip method or FDD method described above. When each of 2 kinds of specimens are plural, results of measurement are statistically analyzed and used for positioning of genes on the fixation substrate. Original data obtained in DNA chip experiments comprise the signal intensity of the 2 kinds of comparable specimens and ratios between the signal intensity of the 2 kinds of specimens. For example, when specimen 1 is labeled with fluorescent dye Cy3 and specimen 2 with Cy5, data obtained are Cy3 fluorescent intensity originated from specimen 1, Cy5 fluorescent intensity originated from specimen 2, and Cy3/Cy5, the ratio of fluorescent intensity.

Original data obtained in FDD experiments comprise the intensity of bands of lanes in electrophoresis of specimen 1, that of specimen 2, and the ratios between the intensities of bands derived from 2 specimens. For example, when both specimens 1 and 2 are labeled with the same dye (Cy3, for example), data obtained are Cy3 fluorescent intensity originating from specimen 1, that originated from specimen 2, and the ratio between 2 fluorescent intensities. Statistical analysis is conducted using (1) fluorescent intensity ratios or (2) fluorescent intensity originated from specimens 1 and 2.

TABLE 39 shows results of experiments using 2 kinds of specimens that are analyzed based on the above (1) fluorescent intensity ratios. Columns in TABLE 39 are, from the left, gene name (symbolic name in Unigene), mean fluorescent intensity ratios, standard deviation (SD) and CV value (SD/mean). In TABLE 39, specimen 1 is CD3+ cell (T cell) originating from peripheral blood of 3 healthy subjects, and specimen 2 is CD3− cell (lymphocytes other than T cell) originating from peripheral blood of 3 healthy subjects. Gene groups in specimens 1 and 2, the fluorescent intensity ratio of which is 3 or higher in the state of expression, are listed in the order of the mean value. TABLES 39 shows results of experiments using DNA chips with several thousands genes. Therefore, similar values can be obtained from other several thousands genes aside from those in TABLE 39, and these genes can be listed in the ascending or descending order of mean values, as one pleases. In TABLE 39, the fluorescent intensity ratios in the above (1) are those of CD3− cells/CD+ cells, and in (2) are those of CD+ cells/CD− cells. When DNA chips are newly created, the whole or part of several thousand gene probes can be positioned on the DNA chip fixation substrate according to the ascending or descending order of the mean fluorescent intensity. For example, probes can be positioned selecting genes among several thousand genes with the fluorescent intensity ratio 2 or higher, that is, the difference in gene expression between specimens 1 and 2 is twice or more.

Figure 5A:
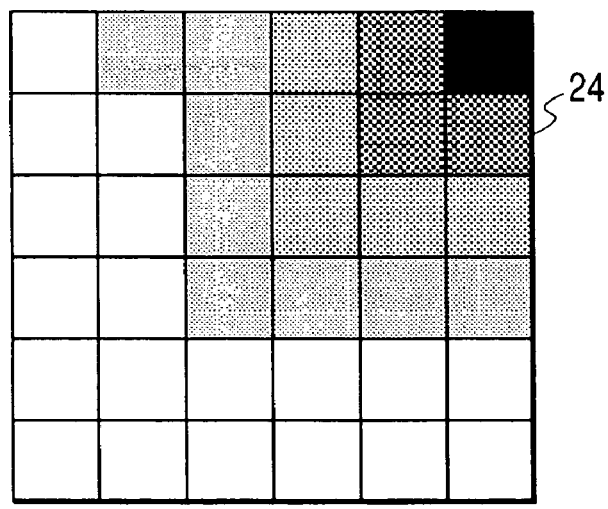
FIG. 5 is an example of positioning rule.
Figure 5B:
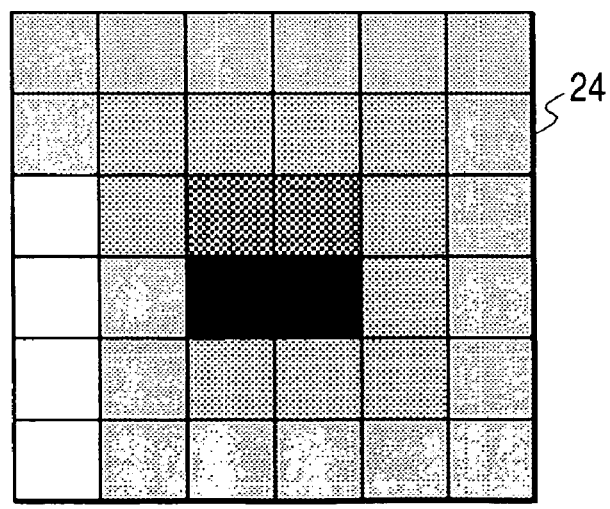
Figure 6A:
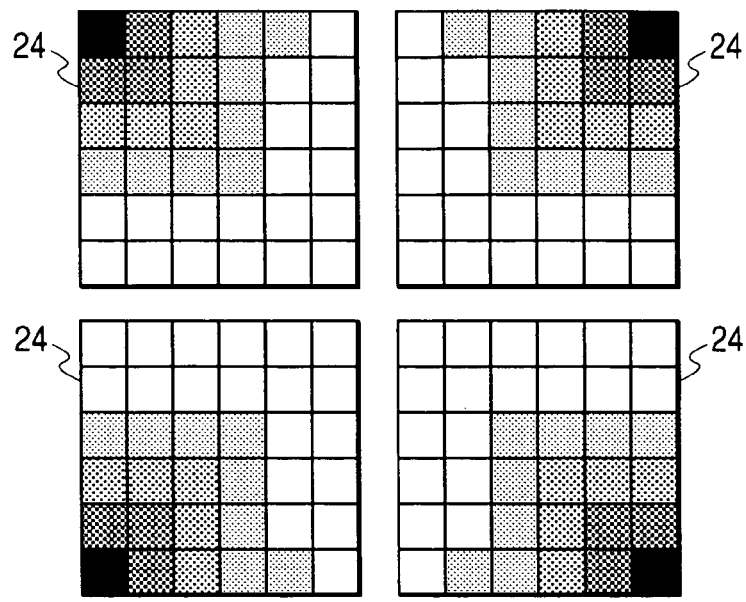
FIG. 6 illustrates an example of plural positioning on one DNA chip substrate.
Figure 6B:
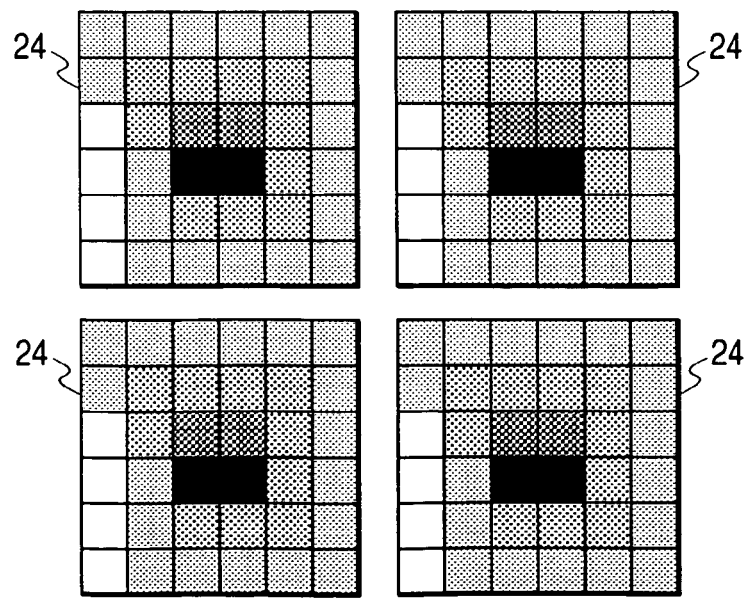

FIG. 5 illustrates an example of the positioning rule. Darkness of color is in proportion to the size of the mean fluorescent intensity ratio. FIG. 5(A) illustrates an example in which probes are positioned diagonally originating at the corner of DNA chip substrate. FIG. 5(B) illustrates an example in which probes are positioned concentrically originating at the center of DNA chip substrate. FIG. 6 illustrates examples in which positionings shown in FIG. 5 are placed side by side, or in plural numbers, on one DNA chip substrate. FIG. 6(A) illustrates 4 of the positioning shown in FIG. 5(A), and FIG. 6(B) illustrates 4 of the positioning shown in FIG. 5(B). FIG. 6 corresponds to gene positioning described in the above 1, in which genes are classified according to functions, and the final positioning is decided based on experimental data.

TABLE 40 shows results of experiments using 2 kinds of specimens same to TABLE 39 that are analyzed based on the above (2) specimen 1-originating fluorescent intensity and specimen 2-originating fluorescent intensity. Columns in TABLE 40 are, from the left hand side, gene name (symbolic name in Unigene), t value that is statistic value obtained in t-test, and P value that is significant probability derived from t value. Genes with P value, or significant probability, 0.003 or lower, are listed in the ascending order. TABLE 40 shows the results of experiments using DNA chips with several thousands of genes. Therefore, similar values are obtained from other several thousands of genes aside from those in TABLE 40, and these genes can be listed in the ascending or descending order of t value or P value, as one pleases. When DNA chips are newly created, the whole or part of several thousands of gene probes can be positioned on the DNA chip fixation substrate according to the ascending or descending order of t value or P value. Gene probes can be positioned on the DNA chip fixation substrate in the similar way using other statistic values obtained in testing methods other than t test, such as rank sum test.

When DNA chips are newly created, the whole or part of several thousands of gene probes can be positioned on the DNA chip fixation substrate according to the ascending or descending order of t value. For example, suppose the significant probability P is lower than 0.2, that is, the difference in the gene expression between specimens 1 and 2 is zero, probes can be positioned selecting genes among several thousands of genes with the 20% probability that the supposition is incorrect. Probe positioning can also be decided based on results of FDD in the same process as in TABLES 39 and 40. Aside from statistic analysis, using support vector machine (SVM) algorithm, well known in the field of machine learning, weight matrix factor (wi) corresponding to each gene is obtained and probe positioning can be decided in the ascending or descending order of wi. Probe positioning can be decided using any method, aside from statistic analysis and machine learning, that can rank genes based on experimental data.

As regards effects of stress on the body, various genes related to the nervous, immune and endocrine systems are thought to play roles. Details have been unclear. Therefore, this Inventors investigated changes in gene expression profile in human peripheral blood samples by creating array with a large number of genes/EST as probes and selected genes, the expression of which changed markedly as stress load increased. As the probes of array, 15,000 kinds of genes/EST were purchased from IMAGE Consortium and used to create DNA probes array for screening. Exercise stress and gastric ulcer stress were chosen as typical stress stimulants.

With respect to exercise stress, subjects on bicycle ergometers received for a continuous 60 minutes the load of approximately 80% (80% $VO_2max$) in relative value, when the maximal individual oxygen intake ($VO_2max$, the maximum value of oxygen taken up by blood in unit time) is defined as 100%. When measured in actual subjects, the 80% $VO_2max$ is approximately 180 watts at bicycle ergometer intensity. Pulse rates during exercise were between 150 and 175/min. The lactate threshold (LT) corresponds to approximately 60% $VO_2max$, and heart rates between 110 and 130/min. Therefore, the exercise load of 80% $VO_2max$ for 60 min was thought to be sufficient intensity as exercise stress load. Peripheral blood 50 cc was collected within 5 min after the completion of exercise. Messenger RNA was extracted from leukocyte and reverse transcribed in prescribed methods for DNA synthesis. At reverse transcription, fluorochrome-labeled DNA was synthesized using dCTP labeled with fluorescent dye Cy-5 (labeled cDNA: exercise stress load). Meanwhile, prior to exercise stress load, peripheral blood 50 cc was collected from the same subjects. Messenger RNA was extracted in the same process and reverse transcribed using Cy-3 labeled dCTP for cDNA synthesis (labeled cDNA: control).

Equivalent weight of labeled cDNA of exercise stress load and that of control were mixed, placed on the above-mentioned DNA probe array for screening, and hybridized under prescribed conditions. After rinsing, fluorescent intensity at each spot was measured using a laser scanner for evacuation of kinds and levels of genes expressed in cDNA of exercise stress load and that of control. TABLE 1 shows genes that had changes in the level of expression more than twice, when the level of expression was compared between the two. The increases in the level of expression in TABLE 1 are standardized assuming that the levels of expression of housekeeping genes, such as β-actin, HPRT and GAPDH, is stable. The level of expression of these genes is thought to be stable under various stimulations.

Under exercise stress, the increases in the level of expression were observed in genes related to hormones of the hypothalamic-posterior pituitary system such as vasopressin and anginine vasopressin, adrenocorticotropic hormone (ACTH) receptor genes and genes related to glucocorticoids (cortisol). The level of expression also increased in genes related to catecholamine such as monoamine oxidase. In addition, the expression increased in cytokine genes such as interleukin 6 (IL-6), transcription factors such as NF-κB, and HSP70 and HSP90, heat shock proteins. Observed also were changes in proton pump genes, that is, decreases in $Ca^{2+}$ATPase, and increases in expression of apoptosis related genes called GADD34.

With respect to gastric ulcer stress, messenger RNA was extracted from peripheral blood 50 cc collected from patients with gastric ulcer, and reverse transcribed in prescribed methods for cDNA synthesis. At reverse transcription, fluorochrome-labeled cDNA was synthesized using dCTP labeled with fluorescent dye Cy-5 (labeled cDNA: gastric ulcer stress). Meanwhile, peripheral blood 50 cc was collected from healthy subjects who do not have gastric ulcer. Messenger RNA was extracted and reverse transcribed using Cy-3 labeled-dCTP for cDNA synthesis in the same process. (labeled cDNA: control).

Equivalent weight of labeled cDNA of gastric ulcer stress and that of control were mixed, placed on the above-described DNA probe array for screening and hybridized under prescribed conditions. After rinsing, fluorescent intensity at each spot was measured using a laser scanner for evaluation of kinds and levels of gene expression in cDNA of gastric ulcer stress and that of control. TABLE 2 shows genes that had changes in the level of expression more than twice, when the level of expression was compared between the two. The increases in the level of expression in TABLE 2 are standardized assuming that the level of expression of housekeeping genes, such as β-actin, HPRT and GAPDH, is stable. The level of expression of these genes is thought to be stable under various stimulations.

Under gastric ulcer stress, the increases in the level of expression were observed in genes related to hormones of the hypothalamic-anterior pituitary system such as CRH, and genes related to ACTH and glucocorticoid. Conversely, there were little changes in the level of expression of genes related to hormones of the hypothalamus-posterior pituitary system such as vasopressin. Observed also were, as in exercise stress, increases in the expression of cytokine genes such as IL-6 and HSP70 and HSP90, heat shock proteins. The expression of ERK6, a signal transfer gene, and JUN, a transcription factor, as well as anti-inflammation related genes such as prostaglandin increased.

The above findings suggested that genes that had more than twice increases in the level of expression, in either exercise stress or gastric ulcer stress, included genes related to corticotropin-releasing hormones (CRH) such as vasopressin and oxytocin, ACTH and adrenocortical hormones such as glucocorticoid, reflecting activation of the pituitary glands and adrenal cortex by excitation of the hypothalamus. Hereinafter, the hypothalamic-pituitary adrenocortical system is called HPA system. Involvement of catecholamine related genes reflected the activation of sympathetic adrenomedullary (SAM) system. Hormones produced by the endocrine system such as HPA system and SAM system were secreted into blood and bound with hormone receptors on blood cells, increasing the expression of G-proteins and intracellular signal transfer related genes, such as adenylatecyclase and NF-κB. Finally, the expression of cytokine gene was induced. The expression of stress proteins such as heat shock protein increased as a part of stress reaction at cell level. Activation of glucocorticoid receptor by adrenocortical hormones (glucocorticoid) induced apoptosis in the calcium pathway. Changes in expression occurred in the similar gene groups under 2 completely different stresses suggested that it would be useful in analysis of complex system of stress reaction to observe changes in the expression intensity of these gene groups. That is to say, for analysis of degree of stress, DNA array is the most appropriate, on which the necessary but minimal amount of the following genes are fixed; (1) internal and external standard genes for proofreading genes, (2) stress resistant and survival related genes and hormone genes such as HSP, (3) cytokine genes, (4) apoptosis and cell death related genes, (5) anti-inflammation and cell growth inhibition related genes such as glucocorticoid, (6) immune response related transcription factor or signaling molecules, (7) cell injury-inducing cytokine inductive transcription factor or signaling molecules, (8) cell growth inhibition related transcription factor or signaling molecules, and (9) stress response related transcription factor or signaling molecules.

By dividing probe fixation regions on the support medium according to the above classification (1) to (9), persons performing measurements are able to recognize results in patterns. If probe fixation regions are not divided by gene functions, processes of displaying results are required after fluorescent signals are obtained, which include changes in positions of spots using computer, number plotting and graph display. By classifying probe genes according to functions and positioning said genes on substrate according to functions, persons performing measurements are able to judge instantly the degree of stress just by displaying fluorescent signals on the screen. Thus, simplification of equipment structure and lowering cost can be achieved easily. Proofreading is necessary in order to eliminate manufacturing variations, when plural numbers of array are created. Oligonucleotides for proofreading are called internal and external standard genes for proofreading. An example of internal standard gene for proofreading is housekeeping gene. The housekeeping gene works in coding of structural proteins and enzymes of the energy metabolism system that are necessary for cell survival. The gene is thought to exist in any cell with different differentiation. For example, β-actin, GAPDH, HPRT, α-tubulin, transferrin receptor and ubiquitin are housekeeping genes. As the gene is already present in subjects' samples such as those of leukocyte, the gene can be the internal standard for proofreading. Internal standard means substances that are already present in samples without being added from outside and can be standard at proofreading. External standard genes for proofreading are gene sequences that are not present in humans but present in plants, microorganisms and insects. For example, *Arabidopsis thaliana* gene, plasmid DNA, bacteriophage DNA and firefly luciferase gene are external standard. As the gene is not present in subjects' samples such as those of leukocytes, external standard genes at known concentrations are added to samples at the time of measurement to be used as external standard for proofreading. External standard means substances that are not already present in samples and added separately from outside to be standard for proofreading.

Stress related genes are proteins that are induced at the time of stress caused by physical and environmental factors such as heat shock. For example, HSP, a kind of stress protein, expresses when cells are exposed to high temperature. This HSP expresses and increases by not only external stimulation such as exposure to high temperature but also direct injection of denatured protein into cells (Anathan, J. et al. Abnormal proteins serve as eukaryotic stress signals and trigger the activation of heat shock genes. Science, 232, 252-254, 1986). That is to say, the expression of HSP is not induced by the bodily systems such as nervous, endocrine and immune systems, but by changes occurring inside cells. HSP70, a HSP, is known to have the function of inhibition of apoptosis, which is called program cell death (Mosser, D. D. Roles of the human heat shock protein hsp70 in protection against stress-induced apoptosis. Mol. Cell Biol., 17, 5317-5327, 1997). Apoptosis is a form of cell death that occurs in cells that are exposed to viral infections, oxidation stress, radiation and anticancer drugs. Apoptosis is induced by excessive stress on cells. HSP70 inhibits cell death by providing cells with stress resistance. Cells in which HSP70 expresses are not only continuously resistant to stress that was the direct cause but also resistant to other stresses (cross resistance), suggesting that HSP is the stress reaction processing mechanism that cells possess. It is extremely useful to know degrees of, or increase or decrease in, expression of stress protein, in order to evaluate degrees of stress at the cellular level. More than 30 kinds of stress proteins are known to exist. Therefore, it is desirable to fix approximately 30 or more oligo probes, including stress proteins, on the oligonucleotide array of this Invention. Stress proteins include, for example, HSP27 (small HSP), HSP40 (Hdj1), HSP47, HSP60/HSP10, HSC70, HSP70, mtHSP70, HSP90, HSP100 (GRP95), HSP150 (ORP150), Bip (GRP78) and TriC.

Genes related to cell survival include, aside from stress proteins, for example, cyclin, which regulates cell cycle, cyclin dependent kinase (CDK), CDK inhibitors (CKI) such as cyclin A, cyclin B, cyclin D, cyclin E, CDK1, CDK2, CDK4 and CDK6.

"Hormones" means organic compounds that are produced in endocrine glands, secreted in blood and carried to target organs, where microdose demonstrates specific physiological actions. Typical endocrine systems include (a) HPA system, (b) SAM system, (c) automatic nervous-pancreatic endocrine system, (d) hypothalamic-sympathetic-renin angiotensin system, (e) hypothalamic-posterior pituitary system, and (f) opioid peptide system. Hormone-related genes include, for example, vasopressin (AVP), vasopressin receptor (AVPR), CRH, CRH receptor (CRHR), MC2R, REN, TH, TSHB and TSHR.

"Cytokines" are general names of bioactive peptides that induce cell growth differentiation and are secreted by blood cells. Cytokines differ from hormones in that cytokine works near where they are secreted and blood concentrations of cytokines are equal to or lower than those of hormones. Major cytokines include granulocyte-colony stimulating factor (G-CSF), macrophage-colony stimulating factor (M-CSF), granulocyte-macrophage colony stimulating factor (GM-CSF), erythropoietin, thrombopoietin, stem cell factor (SCF), interleukin-1, -2, -3, -4, -5, -6, -7, -8, -9, -10, -11, and -12, tumor necrosis factor (TNF) and interferon.

Most of the genes with functions of inducing cell death due to stress are thought to be apoptosis-related genes, because almost all cell deaths in the body are those called apoptosis. Pathways where apoptosis occurs include calcium pathway, death signal pathway, ceramid pathway, mitochondria pathway and DNA injury pathway. In calcium pathway, phosphatidyl-inositol-3-phosphate receptor, calmodulin, ALG2 and carpine play roles. In death signal pathway, TNFα, Fas ligand, TRADD, FADD, RAIDD, FADD, RIP, RAIDD, CASP8, CASP1, CASP3, TRAMP and TRAIL are known to play roles. In ceramid pathway, stress-activated protein kinase (SAPK)/Jun terminal-N kinase (JNK) plays a role. In mitochondria pathway, Bcl-2 associated X protein (Bax2), Bcl-2, Bcl-xL, and caspase gene play roles. In DNA injury pathway, p53, p21, p51, p73 and MDM2 genes play roles. Genes related to anti-inflammation such as glucocorticoid and genes related to growth inhibition include cytochrome P450 gene 11B1 (CYP11B1), CYP11B2, CYP17, CYP21A2, glucocorticoid modulatory element binding protein (GMEB), glucocorticoid receptor repression factor (GRLF), myocilin (MYOC), glucocorticoid receptor α (NR3C1), proopiomelanocortin (POMC) and prostaglandin G/H synthase precursor.

Transcription factors and signaling molecules related to immune response, cytokine induction, growth inhibition and stress resistance include, for example, ATF/CREB transcription factor, NF-κB transcription factor, JUN gene and 14-3-3n gene. In most signal transfers, signals are generally transferred in the mechanism that protein is activated by chemical change of phosphorylation and the activated protein in turn induces phosphorylation of the adjacent protein, and so forth. Signal transfer pathways are called pathways, which are generally differentiated by naming with representative proteins on pathways. Known are, for example, MAPK (mitogen activated protein kinase), ATM (ataxia telangiectasia mutated), BCR (B cell receptor), CD40 (related to tumor necrosis factor receptor), CXCR4 (related to chemokine receptor), EGF (epidermal growth factor), EPO (erythropoietin), FAS (fatty-acyl-CoA synthase), FcEpsilon (Fc fragment of IgE receptor), IFN (interferon) alpha, IFN (interferon) gamma, IGF-1 (insulin-like growth factor-1), IL (interleukin)-2, -3, -4, -5, -6, and -18, NFκB (nuclear factor κB), NCF (nerve growth factor), p53, PDGF (platelet derived growth factor), PLC (phospholipase C), SODD (silencer of death domains), TCR (T cell receptor), TGFβ (transforming growth factor β), TNFR1 (tumor necrosis factor receptor 1), TNFR2 (tumor necrosis factor receptor 2), TPO (thrombopoietin), and Wnt (wingless/int-1). By placing genes that work in coding of proteins that are keys of these pathways on array as probes, signal transfer pathways induced by stress stimulation can be identified. In particular, for patients with chronic stress, which is caused due to dysfunction of one of the proteins on the signal transfer pathway, treatment plans can be determined by identifying the site where signal transfer is interrupted.

Another example of DNA chip is described, in which oligonucleotides are placed in such a way so that the presence or absence of stress can be understood instantly. This example of practice is one of the examples of gene positioning based on experimental data.

Figure 10A:
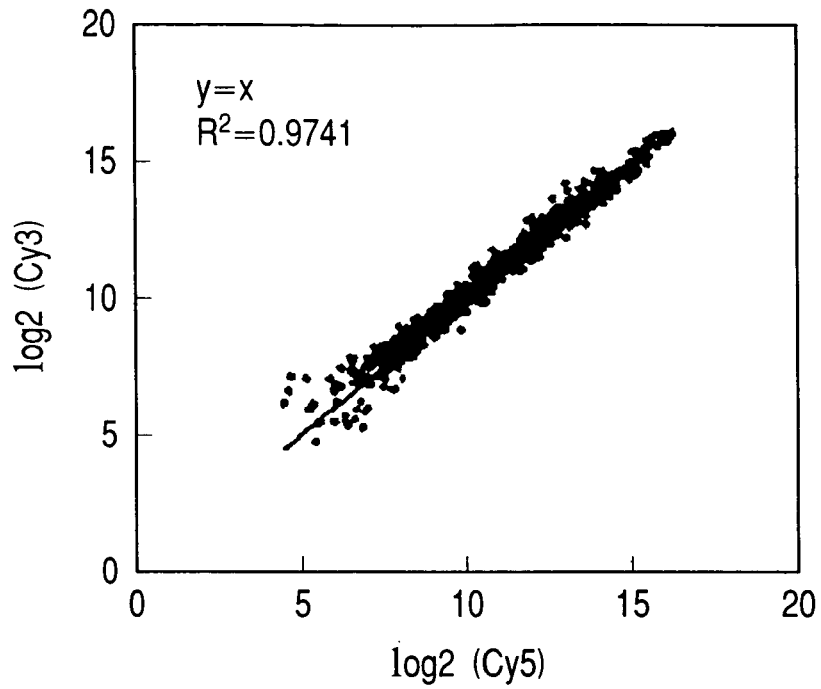
FIG. 10(A) illustrates control scatter plot.
Figure 10B:
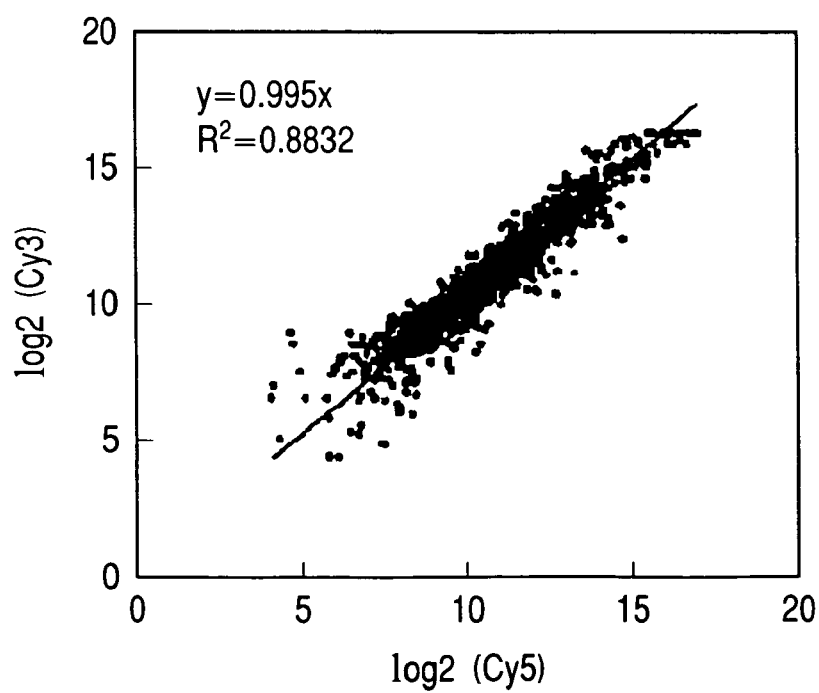
FIG. 10(B) illustrates a patient's scatter plot.
Figure 12A:
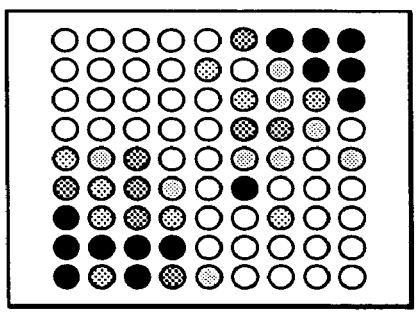
FIG. 12 illustrates fluorescence patterns of control A to E.
Figure 12B:
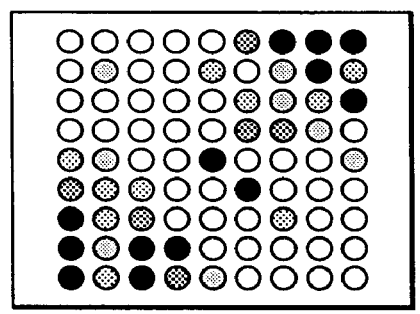
Figure 12C:
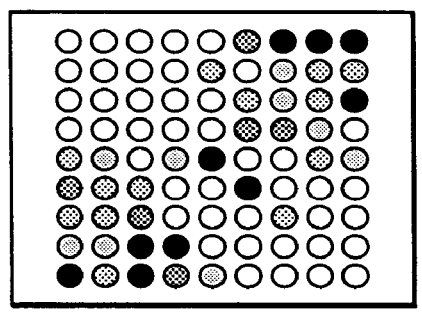
Figure 12D:
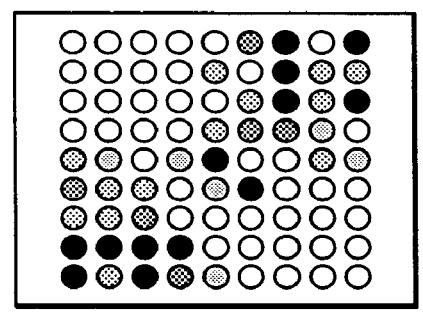
Figure 12E:
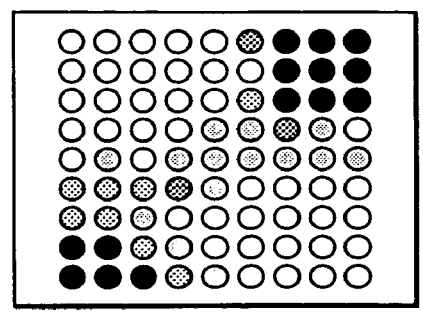
Figure 13:
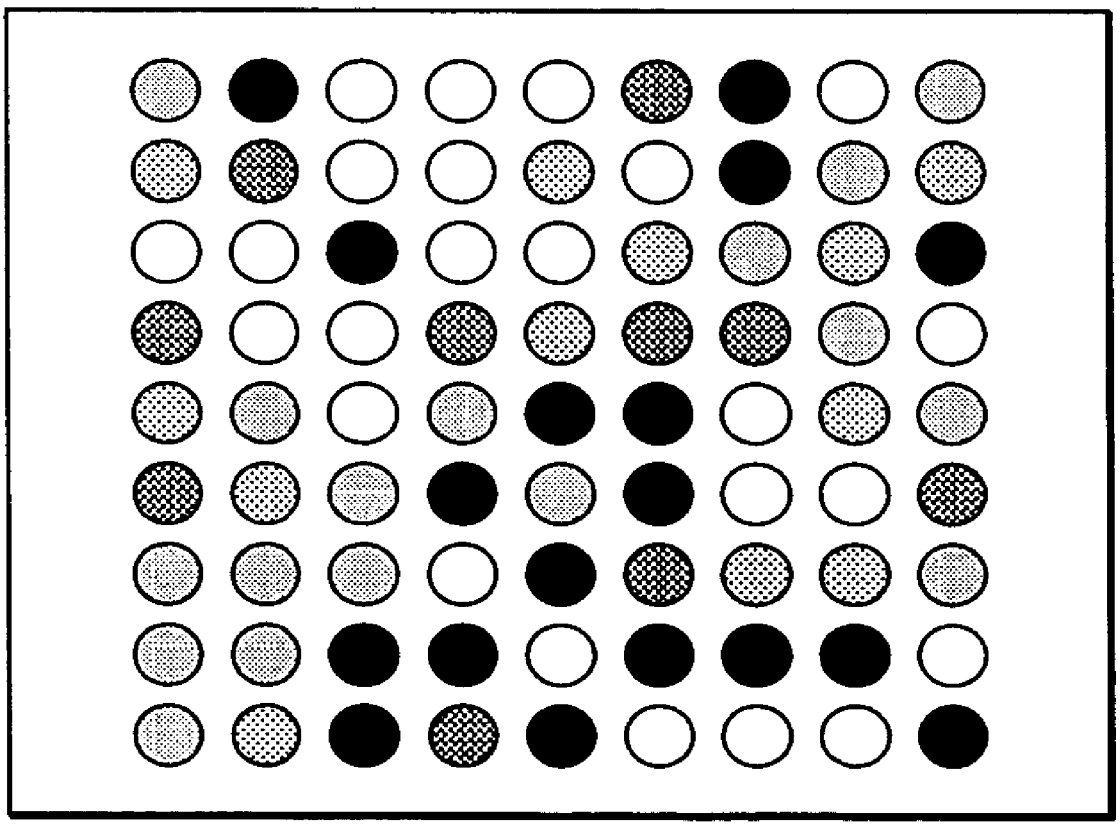
FIG. 13 illustrates a patient's fluorescence pattern.

One week before and 5 hours after an examination, peripheral blood 10 cc was collected from one person (patient A) who became excessively tense during examination and 5 persons (control A, B, C, D and E) who did not feel much tension during the same examination. Total RNA was extracted from lymphocytes from both groups. Degrees of stress of patient A, who experienced excessive tension and 5 controls were significantly different in tests by interview conducted by a specialist. Tests by interview confirmed that 5 persons who did not feel excessive tension were not in the state of stress. In experiments with DNA chip housing several thousands genes, the state of expression 1 week before examination was compared with that 5 hours after examination in control A to E. The difference in the state of expression was small between the two. Correlation ($R^2$) between fluorescent intensity before examination and that after examination was 0.94 to 0.97. FIG. 10(A) shows scatter plot of control A. Correlation of the same sample is 0.99. Therefore, values 0.94 to 0.97 indicate that the state of expression before examination did not differ greatly from that after examination. The means of fluorescent intensity ratios with several thousands of genes were obtained in control A to E and listed in ascending order. Then, gene probes were positioned originating at the right upper corner of chip substrate toward the left lower corner following the rules of FIG. 11. Each square of FIG. 11 is the position where gene probes are fixed. Numbers in squares indicate that genes are positioned following the direction of arrows in FIG. 11 in the order of size of the fluorescent intensity ratio (Cy5/Cy3). The positioning of FIG. 11 shows that genes with large Cy5/Cy3 are concentrated and fixed at the right upper portion and genes with large Cy3/Cy5 at the left lower portion. FIG. 12 shows patterns obtained following measurement of RNA by DNA chip in FIG. 11 in 5 controls, A to E. In FIG. 12, the greater the change in the gene expression, or the greater the ratio Cy5/Cy3 or Cy3/Cy5 is, the darker the gene is. FIGS. 12(A) to 12(E) illustrate patterns of control A to E. In all five, the patters are similar, or the right upper and left lower portions have dark circles and the intermediate is light. FIG. 13 shows the pattern obtained in measurement in patient A using DNAA chip in FIG. 11. In FIG. 13, the right upper and left lower portions have fewer dark circles. The differences between the 2 figures are instantly recognizable. The correlation ($R^2$) between fluorescent intensity before and after examination in patient A was 0.88 (see FIG. 10(B)), which is apparently different from that in 5 controls and the differences are demonstrated in FIGS. 12 and 13.

In order to place the oligonucleotides with the sequence of the above-described genes as probes on the array, it is necessary to decide which parts of the gene sequences are the probes. What must be taken into consideration at that time are melting temperature (Tm) and cross hybridization. In order to carry out highly accurate and highly stringent hybridization between DNA fragments fixed on the DNA array and DNA fragments originating from samples, the relationship is important between hybridization temperature (Th) and Tm of fixed DNA fragment. It is necessary that the difference between the Tm of fixed DNA fragments and the Th does not exceed 30° C. Cross hybridization occurs when there is high homology among DNA sequences. Therefore, in order to prevent cross hybridization from occurring, it is necessary that any of fixed DNA fragments and sample-originated DNA fragments have low homology with DNA fragments that do not hybridize originally with fixed DNA fragments. Furthermore, it is desirable that these DNA fragments do not contain portions that have high homology with sequences with mini hair pin structure or repetitive sequence that is known in human genes as Alu sequence. It is also necessary to calculate the homology not only between gene sequences fixed on one piece of array but also between DNA sequences and gene sequences of species listed on GENBANK etc. It is desirable not to select DNA sequences for fixed DNA fragments that have high homology with DNA sequences of gene groups that are possibly contained in samples to be measured.

DNA fragments to be fixed as probes can be synthesized in PCR reaction using commercially available cDNA library as template. Oligonucleotide array can be created from synthesized DNA fragments by preparing prescribed concentrations (0.1 to 1.0 μG/μL), and spotting using a spotter on slide glasses that are already coated with polylysine or aminosilane. Degrees of stress are studied using the above-described oligonucleotide array in the following procedure. First, peripheral blood samples are collected from several volunteers who do not have stress symptoms, and messenger RNA is extracted from leukocytes. For example, a messenger RNA pool of average healthy people can be obtained by mixing messenger RNA from many persons. This messenger RNA pool is described hereinafter in the Specification of this application as Universal Control. Next, peripheral blood samples are collected from test subjects, and messenger RNA is extracted from leukocytes. With messenger RNA of peripheral blood of test subjects, labeled cDNA is synthesized using Cy5-dCTP in reverse transcription using oligo dT primer. With messenger RNA in Universal control, labeled cDNA is synthesized using Cy3-dCTP. Test subjects' cDNA (Cy5 labeled) and Universal control cDNA (Cy3 labeled) are mixed and placed on the same, above-described oligonucleotide array for hybridization at prescribed temperature and duration. It is desirable to have hybridization temperature between 45° C. and 70° C., and time between 6 and 18 hours. Following hybridization, fluorescent intensity of Cy5 and Cy3 at each site where genes are spotted is measured using a fluorescent scanner and compared for the difference in the level of expression. Extraction of messenger RNA is performed with either monocytes, which account for 3 to 7% of leukocytes, or lymphocytes, which account for 25 to 33%. Analysis can be expected to reflect better the degrees of stress, because the monocyte has capability to differentiate to macrophage, which is an important cell in the natural immune system, and the lymphocyte to T cell and B cell, which are important cells in the acquired immune system. In addition, these leukocytes have difference cell rotation (dynamics) including maturation in bone marrow, retention time in peripheral blood and life duration. Therefore, it is possible to evaluate acute bioresponse using polynuclear leukocytes (neutrophil), short-term reaction using monocytes and relatively long-term bioresponse using lymphocytes.

Below is an example in which changes in degrees of stress in daily activities were studied in one subject.

The 793 genes (TABLE 3 and TABLE 38) were selected from GENBANK Unigene by way of key words retrieval, etc. based on the rationale described in the above "Summary of the Invention". These genes work in coding of (1) internal and external standard genes for proofreading, (2) stress resistance and survival related genes such as HSP and hormone genes, (3) cytokine genes, (4) apoptosis and cell death related genes, (5) anti-inflammation related genes such as glucocorticoid and cell growth inhibition related genes, (6) immune response related transcription factor and signaling molecules, (7) cell injury inducing cytokine inductive transcription factor and signaling molecules, (8) cell growth inhibition related transcription factor and signaling molecules, and (9) stress response related transcription factor and signaling molecules.

Next, 793 oligonucleotide probes with highly specific and similar Tm were designed following algorithm consisting of the following procedures; 1. Reading of gene sequence files, 2. Input of salt concentrations and experimental conditions at hybridization, 3. Input of length of fixed DNA fragments, 4. Calculation of melting temperature (Tm) of fixed DNA fragments, followed by elimination from lists of candidates of DNA fragments whose melting temperature does not meet a certain range of Tm, 5. Elimination from the candidate lists of DNA fragments with specific superorganization or repetitive sequences, 6. Elimination from the candidate lists of DNA fragments with high homology with repetitive sequences such as Alu sequence, and 7. Elimination from the candidate lists of DNA fragments with high homology with other gene sequences. Each of the designed 793 sequences were synthesized using an oligonucleotide synthesizer. The total 796 kinds oligonucleotides comprising the above 793 human gene probes and 3 kinds of oligonucleotide sequences that are not present in humans (lambda DNA, pUC18 plasmid DNA and M13 mp18DNA) and are added as external standard genes for proofreading were fixed on a glass substrate in the method published below.

First, commercially available slide glasses (manufactured by Gold Seal Brand) were soaked at room temperature for 2 hours in alkaline solution (sodium hydroxide; 50 g, distilled water; 150 ml and 95% ethanol; 200 ml). The slide glasses were transferred to distilled water for rinsing three times to remove alkaline solution completely. The rinsed slide glasses were soaked for 1 hour in 10% poly-L-lysine solution (manufactured by Sigma), pulled out of solution and centrifuged at 500 rpm for 1 min in a centrifuge for microtiter plate to remove poly-L-lysine solution. The slide glasses were placed in suction incubator for drying at 40° C. for 5 minutes. Amino group was introduced on the slide glasses. The slide glasses with amino group were soaked for 2 hours in 1 mM GMBS (by PIERCE) dimethyl sulfoxide solution and rinsed with dimethyl sulfoxide. Maleamide group was introduced on the surface of the slide glasses. Using a DNA synthesizer (manufactured by Applied Biosystem, model 394), oligonucleotides to which thiol group was introduced were synthesized, and purified in high performance liquid chromatography (HPLC). Next, 1 µl of 2 µM synthesized purified oligonucleotides, 4 µL of HEPES buffer (N-2-hydroxyethylpiperazine-N, -2-ethane sulfonic acid; 10 mM, pH 6.5), and 5 µl of additive (ethylene glycol) were mixed to make spotting solution. The prepared spotting solution was spotted randomly on slide glasses using a spotter (manufactured by Hitachi Soft, SPB10 2000). The slide glasses were left at room temperature to fix oligonucleotides on slide glasses.

At that time, with the intention that persons performing measurements can instantly recognize and judge results on the array, probes were fixed in the positions that were published in FIG. 1 or FIG. 2. Probe positioning was carried out based on the above-described gene classification (1) to (9).

Peripheral blood 50 cc was collected from a test subject who sat up for 3 nights immediately after the sit-up completed. Immediately, messenger RNA was extracted from leukocytes and preserved at −80° C. Peripheral blood 50 cc was collected from the same test subject after a good rest for 1 week. Messenger RNA was extracted in the same manner. From messenger RNA obtained immediately after sit-up, Cy5-labeled cDNA was synthesized in reverse transcription using Cy5-dCTP. From messenger RNA obtained after good rest, Cy3-labeled cDNA was synthesized in reverse transcription using Cy3-dCTP.

Figure 3:
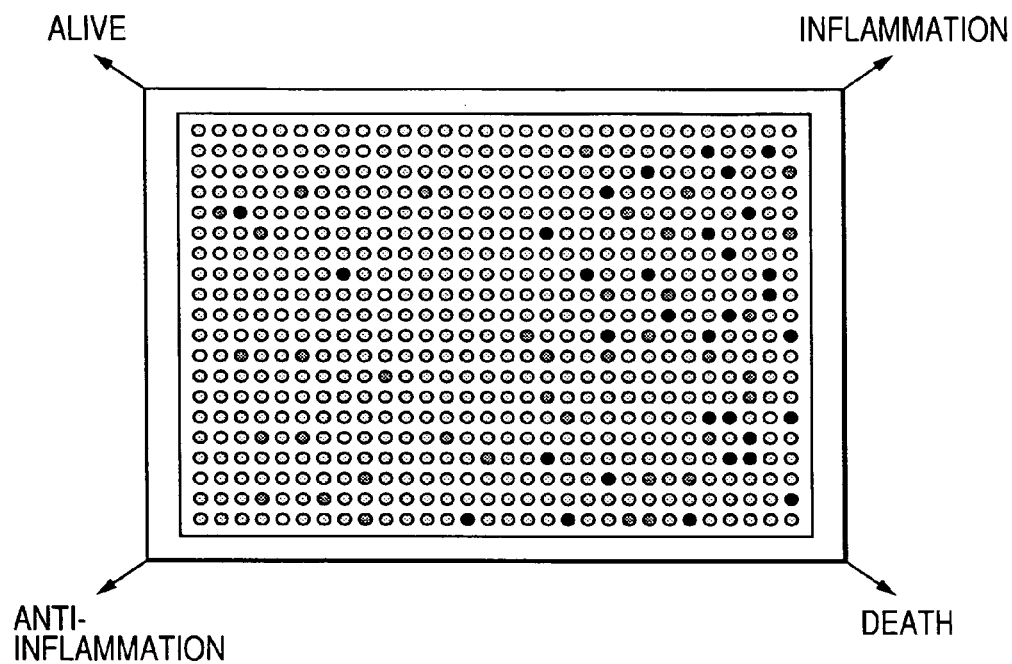
FIG. 3 illustrates an example of stress evaluation.

Equivalent weight of Cy5-labeled cDNA and Cy3-labeled cDNA were mixed, placed on the above-described oligonucleotide array for hybridization at 62° C. for 2 hours. After rinsing, the fluorescent intensity at each spot was measured using a scanner (manufactured by GSI-Lumonics, ScanArray 5000). FIG. 3 shows an image after measurement. Fixed probes were positioned as shown in FIG. 2. The greater the ratio of Cy5 fluorescent intensity/Cy3 fluorescent intensity (sit-up/rest) was, the darker the circle was in FIG. 3. It is known by experience that immune intensity lowers due to loss of sleep. FIG. 3 demonstrates that many genes related to inflammation and cell death related genes in FIG. 2 expressed, suggesting that sitting up for 3 nights resulted in acute malaise, inducing the expression of genes in immune system and apoptosis. The expression of part of stress resistance genes such as HSP increased as a part of stress response. Concerning gene groups related to diseases other than stress.

Cancer can be diagnosed by using DNA chips on which genes that play major roles in cancerization, infiltration and metastasis such as cancer genes, cancer inhibition genes, growth factor, transcription factor, cytokine, apoptosis, cell cycle modulator and DNA repair genes are fixed. Particularly, by positioning at opposites to each other on the support medium the probes that hybridize with cancer genes and probes that hybridize with transcription products of cancer inhibition genes, it will become easier to recognize instantly the correlation between cancer genes and cancer inhibition genes.

Methods of Evaluation

Method for Labeling RNA to Produce cDNA

From the total RNA or messenger RNA extracted from cells and tissues, cDNA is synthesized in transcription reaction originating at primer such as oligo-dT primer using transcription enzymes. At the DNA synthesis, for example, fluorescent labels are taken up by cDNA by adding to solution deoxynucleotides to which fluorescent dyes such as Cy3-dCTP, Cy3-dUTP, Cy5-dCTP and Cy5-dUTP are bound. By hybridizing the fluorescent-labeled cDNA with probes fixed on the DNA chip substrate, RNA profile of genes can be measured using the level of fluorescence.

When the level of the total RNA or messenger RNA in cells and tissues is low, labeling is performed using RNA amplification. Amplifications include, for example, T7 or SP3 amplification using T7 or SP3 polymerase reaction. In T7 amplification, transcription originates at T7dT primer that has T7 sequence and a sequence with several tens of T bases. T7 sequence is present at the terminal of synthesized cDNA in reverse transcription. Synthesis of RNA that is complementary on cDNA and recognizes this T7 sequence is called in vitro transcription using T7. RNA can be amplified several tens to several hundreds times in in vitro transcription. Fluorescent-labeled cDNA can be synthesized using RNA obtained in this RNA amplification in the same method described above as synthesis of cDNA labeled with RNA. By hybridizing this fluorescent-labeled cDNA with probes fixed on the DNA chip substrate, RNA profile of genes can be measured by the level of fluorescence.

Manufacturing Methods of Chip

When oligonucleotide groups are positioned on the DNA chip using a spotter, it is necessary to house beforehand oligonucleotide group in a 96- or 384-well plate. Positioning of wells of the 96- or 384-well plate on coordinates on the DNA chip is determined by how a spotter is set up. When the positioning on the DNA chip is already determined based on Bioinformatics or experimental data as in the Specification of this application, it is necessary to establish the housing positions of oligonucleotide groups on a 96- or 384-well plate according to the establishment of the spotter. Conventionally, the position of oligonucleotide groups on the DNA chip was established according to the housing position of oligonucleotide groups in a 96-well plate. In the Specification of this application, conversely, the housing position of oligonucleotide groups on a 96-well plate is established according to the position of oligonucleotide groups on the DNA chip.

Methods of Display

1. Real Display

The value of fluorescent intensity of Cy5 and Cy3 labeling are displayed in quasi-color according to the intensity. In another quasi-color display, red indicates Cy5 labeling and green Cy3 labeling. On quasi-color images, boarder lines that divide plural sections can be overlapped for display. It is possible to convert images in left and right, or top and bottom inversions and rotation. Graphic displays with bars are possible according to the fluorescent intensity. Three-dimensional bar graphs can be displayed corresponding to the probe fixation positions.

2. Virtual Display

More than 2 DNA chips can be displayed on one piece. For example, using quasi-colors, the mean value of each probe, the largeness of standard deviation, correlation between one probe and another probe can be displayed in the order of the size of correlation. Re-positioning can be displayed based on information of probe positions already registered on computer.

DNA Chip Making Kit

Figure 9:
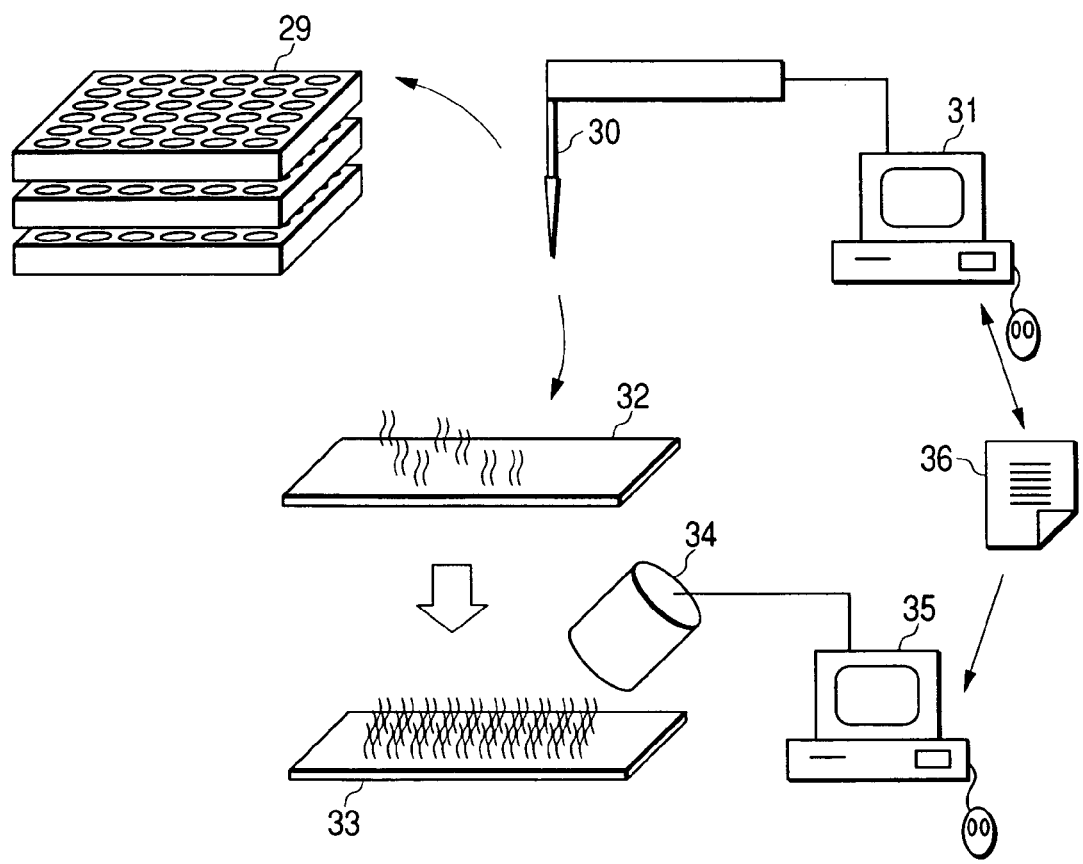
FIG. 9 illustrates an example of DNA chip making kit.

DNA chip making kit can be offered, which is not a completed DNA kit but a partially completed one. For example, as shown in FIG. 9, a kit containing a set consisting of substrate for DNA fixation, basic probe set, positioning information on basic probe set, spotter and computer can be offered. Because of being partially completed, in addition to the basic probe set offered as a kit, new probes can be added as the user desires. The user inputs information on gene functions and the state of expression of added probes. Thus, classification of gene functions and the state of expression housed in positioning information of the basic probe set merge to classification of gene functions and the state of expression of added probe set. Real display and virtual display are materialized on computer screen based on the merged classification of gene functions and the state of expression.

As described above, degrees of stress can be evaluated by using the array of this Invention. It is thought that various changes in and close interaction among the three systems or the nervous, endocrine and immune systems lead to complex stress reaction. Conventional methods of measurement of specific hormones in blood are only measuring the endocrine system, but ignoring the interactions among the three, the nervous, endocrine and immune systems. Consequently, it is difficult to find the correlation between hormone level and degrees of stress in conventional methods because of the individual differences in hormone level and other reasons. In view of defects of conventional methods, this Invention took notice of not only changes in each of the nervous, endocrine and immune systems but also interactions among the three systems, particularly the balance in the interactions. Thus, this Invention was achieved.

It should be further understood by those skilled in the art that the foregoing description has been made on embodiments of the invention and that various changes and modifications may be made in the invention without departing from the spirit of the invention and the scope of the appended claims.

For example, other aspects of this invention are as follows:

(11) A method of displaying results of label detection of hybridization wherein labeled cell-derived RNA are hybridized to an oligonucleotide array comprising multiple subblock regions and oligonucleotides with different base sequences positioned to each of said multiple subblock regions, wherein said oligonucleotides are positioned according to an arrangement pattern wherein oligonucleotides with a first correlation degree are positioned closer to each other than oligonucleotides that have a lower correlation degree; and results of label detection of said hybridization are displayed.

(12) A method of displaying results of label detection of hybridization wherein labeled cell-derived RNA are hybridized to an oligonucleotide array comprising multiple subblock regions and oligonucleotides with different base sequences positioned to each of said multiple subblock regions, wherein said oligonucleotides are positioned according to an arrangement pattern wherein oligonucleotides with a first correlation degree are positioned closer to each other than oligonucleotides that have a lower correlation degree; and results of label detection of said hybridization are rearranged on a screen with determined correlation between oligonucleotides.

(13) A kit for fabrication of an oligonucleotide array comprising multiple subblock regions and oligonucleotides with different base sequences positioned to each of said multiple subblock regions, wherein said oligonucleotides are positioned according to an arrangement pattern wherein oligonucleotides with a first correlation value are positioned closer to each other than oligonucleotides that have a lower correlation value, wherein said kit comprises an oligonucleotide fixation substrate, fixation probes, probe positioning information, a spotter to spot said probes, a monitor screen to display addressing information of the spotter and detection results, or a computer with a monitor that determined the correlation value are provided.

TABLE 1

| GenkBank | Name of gene |
|---|---|
| M14758 | P-glycoprotein (PGY1) mRNA (MDR1) |
| M25647 | vasopressin mRNA; Arginine vasopressin |
| NM_000707 | arginine vasopressin receptor 1B |
| Z11687 | antidiuretic hormone receptor |
| NM_001402 | eukaryotic translation elongation factor 1 alpha 1 |
| U83981 | Homo sapiens apoptosis associated protein (GADD34) |
| NM_006582 | glucocorticoid modulatory element binding protein 1 |
| AB034989 | KIAA0025 gene product |
| M69177 | Human monoamine oxidase B |
| J04027 | ATPase, Ca++ transporting, plasma membrane 1 |
| NM_002415 | macrophage migration inhibitory factor |
| NM_000261 | Homo sapiens myocilin |
| M14584 | Human interleukin 6 mRNA |
| NM_001078 | Homo sapiens vascular cell adhesion molecule 1 |
| NM_005345 | heat shock 70 kD protein 1 |
| M58603 | Human nuclear factor kappa-B DNA binding subunit p105 |
| M34664 | Heat shock 60 kD protein 1 |
| AF028832 | Heat shock 90 kD protein 1, alpha |

TABLE 2

| GenkBank | Name of gene |
|---|---|
| AF022224 | Bcl-2-binding protein |
| NM_004244 | CD163 antigen |
| U82812 | scavenger receptor cysteine rich Sp alpha |
| U47741 | CREB-binding protein |
| X58022 | corticotropin-releasing factor binding protein |
| NM_001402 | eukaryotic translation elongation factor 1 alpha 1 |
| NM_000862 | hydroxy-delta-5-steroid dehydrogenase, 3 beta- and steroid delta-isomerase 1 |
| NM_002228 | v-jun avian sarcoma virus 17 oncogene homolog (JUN) mRNA |
| M14584 | Human interleukin 6 mRNA |
| X79483 | ERK6 mRNA for extracellular signal regulated kinase |
| NM_000529 | melanocortin 2 receptor (adrenocorticotropic hormone) |
| NM_001043 | solute carrier family 6 member 2 (SLC6A2) |
| M59979 | prostaglandin G/H synthase 1 precursor |
| X54079 | Heat shock 27 kD protein 1 |
| D90224 | glycoprotein 34 (gp34) |
| NM_005345 | heat shock 70 kD protein 1 |
| AF028832 | Heat shock 90 kD protein 1, alpha |

TABLE 3

| | |
|---|---|
| M14758 | Homo sapiens P-glycoprotein (PGY1) mRNA (MDR1) |
| M14752 | V-abl Abelson murine leukemia viral oncogene homolog 1 |
| NM_000789 | Homo sapiens dipeptidyl carboxypeptidase 1 (angiotensin I converting enzyme) (ACE) |
| X00351 | cytoplasmic beta-actin (ACTB) |
| L17075 | Human TGF-b superfamily receptor type I mRNA; activin receptor-like kinase 1 (ACVRL1; ALK1) |
| U92649 | Homo sapiens snake venom-like protease (cSVP) mRNA, A disintegrin and metalloproteinase domain 17 (tumor necrosis factor, alpha, converting enzyme) |

TABLE 3-continued

| | |
|---|---|
| L05500 | *Homo sapiens* adenylate cyclase 1 (ADCY1); Human fetal brain adenylyl cyclase mRNA, 3' end |
| AF070583 | *Homo sapiens* clone 24648 adenylyl cyclase mRNA, partial cds |
| NM_004036 | *Homo sapiens* adenylate cyclase 3 (ADCY3) |
| AF250226 | *Homo sapiens* adenylyl cyclase type VI mRNA |
| NM_001114 | *Homo sapiens* adenylate cyclase 7 (ADCY7) |
| Z35309 | *H. sapiens* mRNA for adenylyl cyclase |
| NM_001116 | *Homo sapiens* adenylate cyclase 9 (ADCY9) |
| NM_001117 | *Homo sapiens* adenylate cyclase activating polypeptide 1 (pituitary) (ADCYAP1) |
| NM_001118 | *Homo sapiens* adenylate cyclase activating polypeptide 1 (pituitary) receptor type I (ADCYAP1R1) |
| M18112 | Human poly(ADP-ribose) polymerase mRNA (ADPRT), PARP |
| M87290 | Human angiotensin II type 1 receptor mRNA |
| X65699 | *H. sapiens* mRNA for angiotensin II receptor |
| NM_000686 | *Homo sapiens* angiotensin receptor 2 (AGTR2) |
| NM_005161 | *Homo sapiens* angiotensin receptor-like 1 (AGTRL1) |
| NM_005162 | *Homo sapiens* angiotensin receptor-like 2 (AGTRL2) |
| NM_003488 | *Homo sapiens* A kinase (PRKA) anchor protein 1 (AKAP1) |
| NM_007202 | *Homo sapiens* A kinase (PRKA) anchor protein 10 (AKAP10) |
| AB014529 | A kinase (PRKA) anchor protein 11 (AKAP11); *Homo sapiens* mRNA for KIAA0629 protein, partial cds |
| NM_005100 | *Homo sapiens* A kinase (PRKA) anchor protein (gravin) 12 (AKAP12) |
| NM_007203 | *Homo sapiens* A kinase (PRKA) anchor protein 2 (AKAP2) |
| NM_006422 | *Homo sapiens* A kinase (PRKA) anchor protein 3 (AKAP3) |
| NM_003886 | *Homo sapiens* A kinase (PRKA) anchor protein 4 (AKAP4) |
| NM_004857 | *Homo sapiens* A kinase (PRKA) anchor protein 5 (AKAP5) |

TABLE 4

| | |
|---|---|
| NM_004274 | *Homo sapiens* A kinase (PRKA) anchor protein 6 (AKAP6) |
| NM_016377 | *Homo sapiens* A kinase (PRKA) anchor protein 7 (AKAP7) |
| NM_005858 | *Homo sapiens* A kinase (PRKA) anchor protein 8 (AKAP8) |
| NM_005751 | *Homo sapiens* A kinase (PRKA) anchor protein (yotiao) 9 (AKAP9) |
| M63167 | Human rac protein kinase alpha mRNA (akt1), complete cds |
| NM_001283 | *Homo sapiens* AP1S1adaptor-related protein complex 1, sigma 1 subunit (AP1S1) |
| NM_003916 | *Homo sapiens* adaptor-related protein complex 1, sigma 2 subunit (AP1S2) |
| AF013263 | *Homo sapiens* apoptotic protease activating factor 1 (Apaf-1) mRNA, complete cds |
| M74088 | adenomatous polyposis coli protein (APC protein); DP2.5 |
| AB023421 | *Homo sapiens* mRNA for heat shock protein apg-1; Heat shock protein (hsp110 family) |
| U45879 | Human inhibitor of apoptosis protein 2 mRNA; Apoptosis inhibitor 1 |
| U45878 | Human inhibitor of apoptosis protein 1 mRNA; Apoptosis inhibitor 2 |
| X06820 | *H. sapiens* rhoB gene mRNA; Ras homolog gene family, member B |
| L25081 | *Homo sapiens* GTPase (rhoC) mRNA, complete cds; Ras homolog gene family, member C |
| X95282 | *H. sapiens* mRNA for Rho8 protein; Ras homolog gene family, member E |
| X61587 | *H. sapiens* rhoG mRNA for GTPase; Ras homolog gene family, member G (rho G) |
| U02570 | Human CDC42 GTPase-activating protein mRNA, partial cds |
| X78817 | *H. sapiens* partial C1 mRNA; Rho GTPase activating protein 4 |
| U17032 | Human p190-B (p190-B) mRNA, complete cds; Rho GTPase activating protein 5 |
| AF177663 | *Homo sapiens* GTPase-activating protein 6 isoform 4 (ARHGAP6) mRNA, alternatively spliced, complete cds; Rho GTPase activating protein 6 |
| NM_015366 | *Homo sapiens* Rho GTPase activating protein 8 (ARHGAP8), mRNA |

TABLE 5

| | |
|---|---|
| X69550 | *H. sapiens* mRNA for rho GDP-dissociation Inhibitor 1 |
| L20688 | Human GDP-dissociation inhibitor protein (Ly-GDI) mRNA, D4-GDI |
| U82532 | *Homo sapiens* GDI-dissociation inhibitor RhoGDIgamma mRNA, complete cds; Rho GDP dissociation inhibitor (GDI) gamma |
| U64105 | Human guanine nucleotide exchange factor p115-RhoGEF mRNA, partial cds; Rho guanine nucleotide exchange factor (GEF) 1 |
| Z35227 | *H. sapiens* TTF mRNA for small G protein; Ras homolog gene family, member H |
| U96750 | *Homo sapiens* putative tumor supressor NOEY2 mRNA; Ras homolog gene family, member I |
| NM_005171 | *Homo sapiens* activating transcription factor 1 (ATF1) |
| M31630 | Human cyclic AMP response element-binding protein (HB16) mRNA, 3' end |
| L19871 | Human activating transcription factor 3 (ATF3) mRNA |
| NM_001675 | *Homo sapiens* activating transcription factor 4 (tax-responsive enhancer element B67) (ATF4) |
| NM_012068 | *Homo sapiens* activating transcription factor 5 (ATF5) |
| NM_007348 | *Homo sapiens* activating transcription factor 6 (ATF6) |
| NM_006856 | *Homo sapiens* activating transcription factor 7 (ATF7) |
| U33841 | Human ataxia telangiectasia (ATM) mRNA |
| M25647 | Human vasopressin mRNA; Arginine vasopressin (neurophysin II, antidiuretic hormone, diabetes insipidus, neurohypophyseal) |
| L25615 | Human arginine vasopressin receptor 1 (AVPR1) mRNA, complete cds |
| NM_000707 | *Homo sapiens* arginine vasopressin receptor 1B (AVPR1B), mRNA |
| Z11687 | *H. sapiens* mRNA for antidiuretic hormone receptor; Arginine vasopressin receptor 2 (nephrogenic diabetes insipidus) |
| AF009674 | *Homo sapiens* axin (AXIN1), partial cds |
| NM_004655 | *Homo sapiens* axin 2 (conductin, axil) (AXIN2), mRNA |
| U66879 | Human Bcl-2 binding component 6 (bbc6) mRNA; BAD protein |
| AF022224 | *Homo sapiens* Bcl-2-binding protein (BAG-1) mRNA |
| AF111116 | *Homo sapiens* silencer of death domains (SODD) mRNA; BCL2-associated athanogene 4 |
| NM_017450 | *Homo sapiens* BAI1-associated protein 2 (BAIAP2), transcript variant 1, mRNA |
| U23765 | Human bcl2 homologous antagonist/killer (BAK) |
| L22474 | Human Bax beta mRNA, apoptosis regulator bax |
| U29680 | Human A1 protein; BCL-2-related protein A1 (BCL2A1); BFL1 protein |

TABLE 6

| | |
|---|---|
| Z23115 | *H.sapiens* bcl-xL mRNA; BCL2-like 1 |
| U59747 | Human apoptosis regulator bclw; KIAA0271; BCL2L2 |
| U34584 | Human Bcl-2 interacting killer (BIK); NBK apoptotic inducer protein; BP4; BIP1 |
| U14680 | Human breast and ovarian cancer susceptibility (BRCA1) |
| X58957 | *H.sapiens* atk mRNA for agammaglobulinaemia tyrosine kinase |
| Y14153 | *Homo sapiens* mRNA for beta-transducin repeat containing protein (beta-TrCP) |
| X83703 | *H.sapiens* mRNA for cytokine inducible nuclear protein; Cardiac ankyrin repeat protein |
| U13699 | Human interleukin 1-beta converting enzyme isoform delta (IL1BCE) mRNA |
| U60519 | Human apoptotic cysteine protease Mch4 (Mch4) mRNA, complete cds |
| U13021 | Human positive regulator of programmed cell death ICH-1L (Ich-1) mRNA, complete cds |
| U13737 | Human cysteine protease CPP32 isoform alpha mRNA, complete cds |
| U28014 | Human cysteine protease (ICErel-II) mRNA, complete cds |
| U28015 | Human cysteine protease (ICErel-III) mRNA, complete cds |
| U20536 | Human cysteine protease Mch2 isoform alpha (Mch2) mRNA, complete cds |
| U37448 | Human Mch3 isoform alpha (Mch3) mRNA, complete cds |
| U60520 | Human apoptotic cysteine protease Mch5 isoform alpha (Mch5) mRNA, complete cds |
| U60521 | Human protease proMch6 (Mch6) mRNA, complete cds |
| U66838 | Human cyclin A1 mRNA, complete cds |
| X51688 | Human mRNA for cyclin A; Cyclin A2 |
| M25753 | Human cyclin B mRNA, 3' end.; Cyclin B1 |
| AF002822 | Human cyclin B2 mRNA, complete cds |
| M74091 | Human cyclin mRNA |
| M64349 | Human G1/S-specific cyclin D1 (CCND1); cyclin PRAD1; bcl-1 oncogene |

TABLE 7

| | |
|---|---|
| M90813 | Human D-type cyclin (CCND2) mRNA, complete cds; cyclin D2 |
| M92287 | *Homo sapiens* cyclin D3 (CCND3) mRNA, complete cds |
| M73812 | Human cyclin E mRNA sequence |
| U47413 | Human cyclin G1 mRNA, complete cds |
| U47414 | Human cyclin G2 mRNA, complete cds |
| U11791 | Human cyclin H mRNA, complete cds |
| D50310 | Human mRNA for cyclin I, complete cds |
| U28694 | Human eosinophil CC chemokine receptor 3 mRNA, complete cds |
| U54994 | Human CC chemokine receptor 5 (CCR5) mRNA, complete cds |
| NM_004244 | *Homo sapiens* CD163 antigen (CD163) |
| M14362 | Human T-cell surface antigen CD2 (T11) mRNA, complete cds |
| J02988 | Human T-cell-specific homodimer surface protein CD28 mRNA, complete cds |
| NM_000732 | *Homo sapiens* CD3D antigen, delta polypeptide (TiT3 complex) (CD3D), mRNA |
| X03884 | Human mRNA for T3 epsilon chain (20K) of T-cell receptor (from peripheral blood lymphocytes). |
| X04145 | Human mRNA for T-cell receptor T3 gamma polypeptide, RON alpha |
| J04132 | Human T cell receptor zeta-chain mRNA, complete cds |
| M12807 | Human T-cell surface glycoprotein T4 mRNA, complete cds |
| M59040 | CD44 antigen (homing function and Indian blood group system) |
| U82812 | Human scavenger receptor cysteine rich Sp alpha mRNA |
| M80462 | Human MB-1 mRNA; CD79A antigen (immunoglobulin-associated alpha) |
| M89957 | Human immunoglobulin superfamily member B cell receptor complex cell surface glycoprotein (IGB) mRNA, CD79B |

TABLE 7-continued

| | |
|---|---|
| M27533 | CD80 antigen (CD28 antigen ligand 1, B7-1 antigen) |
| U04343 | Human CD86 antigen mRNA, complete cds |
| M12828 | *Homo sapiens* T-cell surface protein T8 mRNA |
| M36712 | Human T lymphocyte surface glycoprotein (CD8-beta) mRNA, complete cds |
| S72008 | hCDC10 = CDC10 homolog [human, fetal lung, mRNA, 2314 nt]. |
| U18291 | Human CDC16Hs mRNA, complete cds |
| X05360 | Human CDC2 gene involved in Cell Cycle control; CDK1 |
| M81933 | Human cdc25A mRNA, complete cds |
| M81934 | Human cdc25B mRNA, complete cds. |
| M34065 | Human cdc25Hs mRNA, complete cds |

TABLE 8

| | |
|---|---|
| U00001 | Human homologue of *S. pombe* nuc2+ and *A. nidulans* bimA; Cell division cycle 27 |
| AF067524 | *Homo sapiens* PITSLRE protein kinase beta SV12 isoform (CDC2L2) mRNA, complete cds |
| M80629 | Human cdc2-related protein kinase (CHED) mRNA; Cell division cycle 2-like 5 (cholinesterase-related cell division controller) |
| L22005 | Human ubiquitin conjugating enzyme mRNA, partial cds; Cell division cycle 34 |
| U63131 | Human CDC37 homolog mRNA, complete cds |
| M35543 | Human GTP-binding protein (G25K) mRNA, complete cds |
| AF022109 | *Homo sapiens* HsCdc18p (HsCdc18) mRNA, complete cds |
| L33264 | *Homo sapiens* CDC2-related protein kinase (PISSLRE) mRNA; Cyclin-dependent kinase (CDC2-like) 10 |
| M68520 | Human cdc2-related protein kinase mRNA, complete cds |
| X66357 | *H. sapiens* mRNA cdk3 for serine/threonine protein kinase |
| M14505 | Human (clone PSK-J3) cyclin-dependent protein kinase mRNA; cyclin-dependent protein kinase 4 (CDK4) |
| X66364 | *H. sapiens* mRNA PSSALRE for serine/threonine protein kinase. |
| X80343 | *H. sapiens* p35 mRNA for regulatory subunit of cdk5 kinase |
| U34051 | Human cyclin-dependent kinase 5 activator isoform p39i mRNA, complete cds. |
| X66365 | *H. sapiens* mRNA PLSTIRE for serine/threonine protein kinase |
| X77743 | *H. sapiens* CDK activating kinase mRNA |
| X85753 | *Homo sapiens* mRNA for CDK8 protein kinase. |
| L25676 | *Homo sapiens* CDC2-related kinase (PITALRE) mRNA, complete cds |
| L25610 | *Homo sapiens* cyclin-dependent kinase inhibitor mRNA; melanoma differentiation-associated protein 6 (MDA6); CDK-interacting protein 1 (CIP1); WAF1; p21 |

TABLE 9

| | |
|---|---|
| NM_004064 | *Homo sapiens* cyclin-dependent kinase inhibitor 1B (p27, Kip1) (CDKN1B) mRNA |
| U22398 | Human Cdk-inhibitor p57KIP2 (KIP2) mRNA, complete cds |
| L27211 | Human CDK4-inhibitor (p16-INK4) mRNA; cyclin-dependent kinase 4 inhibitor (CDK4I; CDKN2); multiple tumor suppressor 1 (MTS1); p16 |

TABLE 9-continued

| | |
|---|---|
| U17075 | Human p14-CDK inhibitor mRNA, complete cds.; p15 |
| AF041248 | *Homo sapiens* cyclin-dependent kinase inhibitor (CDKN2C) mRNA, complete cds.; p18 |
| U40343 | Human CDK inhibitor p19INK4d mRNA, complete cds; p19 |
| NM_005194 | *Homo sapiens* CCAAT/enhancer binding protein (C/EBP), beta (CEBPB) mRNA; NF-IL6 |
| AF010127 | *Homo sapiens* Casper mRNA; CASP8 and FADD-like apoptosis regulator; I-FLICE |
| AF016582 | checkpoint kinase 1 (CHK1) |
| AF009225 | *Homo sapiens* IkB kinase alpha subunit (IKK alpha) mRNA, complete cds; IKK1 |
| L29222 | *Homo sapiens* clk1 mRNA; CDC-like kinase 1 |
| L29216 | *Homo sapiens* clk2 mRNA; CDC-like kinase 2 |
| L29220 | *Homo sapiens* clk3 mRNA; CDC-like kinase 3 |
| M58525 | *Homo sapiens* catechol-O-methyltransferase (COMT) mRNA |
| NM_001873 | *Homo sapiens* carboxypeptidase E (CPE) |
| Y00816 | Complement component (3b/4b) receptor 1, including Knops blood group system; CD35 |
| M26004 | Complement component (3d/Epstein Barr virus) receptor 2; CD21 |
| U84388 | Human death domain containing protein CRADD mRNA; CASP2 and RIPK1 domain containing adaptor with death domain |
| NM_004379 | *Homo sapiens* cAMP responsive element binding protein 1 (CREB1) |
| U47741 | Human CREB-binding protein (CBP) mRNA, complete cds |
| U47741 | Human CREB-binding protein (CBP) mRNA, complete cds |
| NM_000756 | *Homo sapiens* corticotropin releasing hormone (CRH), mRNA. |
| X58022 | Human mRNA for corticotropin-releasing factor binding protein (CRF-BP). |
| L23332 | Human corticotropin releasing factor receptor mRNA |
| U34587 | Human corticotropin-releasing factor receptor 2 mRNA |
| U33286 | Human chromosome segregation gene homolog CAS mRNA, Chromosome segregation 1 (yeast homolog)-like |

TABLE 10

| | |
|---|---|
| M37435 | Human macrophage-specific colony-stimulating factor (CSF-1) mRNA, complete cds |
| M10663 | Human T-cell granulocyte-macrophage colony stimulating factor (GM-CSF) mRNA |
| M73832 | Human GM-CSF receptor (GM-CSF receptor) mRNA, complete cds |
| M59941 | Human GM-CSF receptor beta chain mRNA; IL3R-beta |
| X03438 | Human mRNA for granulocyte colony-stimulating factor (G-CSF). |
| M59818 | Human granulocyte colony-stimulating factor receptor (G-CSFR-1) mRNA, complete cds |
| NM_001317 | *Homo sapiens* chorionic somatomammotropin hormone 1 (placental lactogen) (CSH1) mRNA |
| V00573 | Human mRNA encoding placental lactogen hormone |
| L37042 | *Homo sapiens* casein kinase I alpha isoform (CSNK1A1) mRNA |
| M55265 | Human casein kinase II alpha subunit mRNA, complete cds. |

TABLE 10-continued

| | |
|---|---|
| M55268 | Human casein kinase II alpha' subunit mRNA, complete cds |
| X16312 | Human mRNA for phosvitin/casein kinase II beta subunit |
| M92934 | Human connective tissue growth factor (CTGF) |
| X87838 | *H. sapiens* mRNA for beta-catenin |
| U96136 | *Homo sapiens* delta-catenin mRNA, complete cds, Arm |
| L06797 | Human (clone L5) orphan G protein-coupled receptor mRNA, complete cds; Chemokine (C-X-C motif), receptor 4 (fusin) |
| NM_000497 | *Homo sapiens* cytochrome P450, subfamily XIB (steroid 11-beta-hydroxylase), polypeptide 1 (CYP11B1), mRNA. |
| NM_000498 | *Homo sapiens* cytochrome P450, subfamily XIB (steroid 11-beta-hydroxylase), polypeptide 2 (CYP11B2) mRNA. |
| M14564 | Human cytochrome P450cl7 (steroid 17-alpha-hydroxylase/17, 20 lyase) mRNA, complete cds. |
| M17252 | Human cytochrome P450c21 mRNA, 3' end |
| U18321 | Human ionizing radiation resistance conferring protein mRNA; Death associated protein 3 |
| X76104 | *H. sapiens* DAP-kinase mRNA |
| AF015956 | *Homo sapiens* Fas-binding protein Daxx mRNA, complete cds |
| NM_000787 | Dopamine beta-hydroxylase (dopamine beta-monooxygenase) |

TABLE 11

| | |
|---|---|
| M76180 | Dopa decarboxylase (aromatic L-amino acid decarboxylase) |
| AB029497 | *Homo sapiens* gadd153 mRNA for CHOP alternatively spliced isoform (CASIS) |
| U91985 | Human DNA fragmentation factor-45 mRNA, DFF |
| AF241254 | *Homo sapiens* angiotensin converting enzyme-like protein mRNA |
| M60278 | Human heparin-binding EGF-like growth factor mRNA (HBEGF); diphtheria toxin receptor (DTR) |
| X68277 | *H. sapiens* CL 100 mRNA for protein tyrosine phosphatase, Dual specificity phosphatase 1, MKP1 |
| U46461 | Human dishevelled homolog (DVL) mRNA, complete cds. |
| NM_004422 | *Homo sapiens* dishevelled 2 (homologous to *Drosophila* dsh) (DVL2), mRNA |
| U49262 | Human dishevelled (DVL) mRNA, complete cds |
| M96577 | *Homo sapiens* (E2F-1) pRB-binding protein mRNA; retinoblastoma-binding protein 3 (RBBP3); |
| NM_001402 | *Homo sapiens* eukaryotic translation elongation factor 1 alpha 1 (EEF1A1) |
| X04571 | Human mRNA for kidney epidermal growth factor (EGF) precursor; urogastrone |
| U01877 | Human p300 protein mRNA, complete cds |
| X02157 | Human mRNA for fetal erythropoietin |
| M60459 | Human erythropoietin receptor mRNA, complete cds |
| U24231 | Human Fas-associating death domain-containing protein mRNA |
| AJ271408 | *Homo sapiens* mRNA for Fas-associated factor, FAF1 |
| X06948 | Human mRNA for high affinity IgE receptor alpha-subunit (FcERI); Fc fragment of IgE, high affinity I, receptor for; alpha polypeptide |
| M33195 | Human Fc-epsilon-receptor gamma-chain mRNA; Fc fragment of IgE, high affinity I, receptor for; gamma polypeptide |

TABLE 11-continued

| | |
|---|---|
| M28696 | Fc fragment of IgG, low affinity IIb, receptor for (CD32) |
| X51943 | acidic fibroblast growth factor (AFGF) + heparin-binding growth factor 1 precursor (HBGF-1); |
| U67918 | Human keratinocyte growth factor 2 mRNA, complete cds |
| U66199 | Human fibroblast growth factor homologous factor 3 (FHF-3) mRNA, complete cds |
| U66197 | Human fibroblast growth factor homologous factor 1 (FHF-1) mRNA, complete cds |
| U66198 | Human fibroblast growth factor homologous factor 2 (FHF-2) mRNA, complete cds |

TABLE 12

| | |
|---|---|
| U66200 | Human fibroblast growth factor homologous factor 4 (FHF-4) mRNA, complete cds |
| M27968 | Human basic fibroblast growth factor (FGF) mRNA (BFGF; FGFB; FGF2) |
| M17446 | Human Kaposi's sarcoma oncogene fibroblast growth factor mRNA, complete cds |
| M37825 | Human fibroblast growth factor-5 (FGF-5) mRNA, complete cds |
| X63454 | Human fibroblast growth factor 6 precursor (FGF6); HBGF6; HST2 |
| M60828 | Human keratinocyte growth factor mRNA; fibroblast growth factor 7 (FGF-7) |
| U36223 | Human fibroblast growth factor 8 (FGF8); androgen-induced growth factor precursor (AIGF); HBGF8 |
| D14838 | Human mRNA for FGF-9 |
| M34641 | Human fibroblast growth factor (FGF) receptor-1 mRNA |
| M80634 | Human keratinocyte growth factor receptor mRNA; fibroblast growth factor receptor 2 (FGFR2) |
| M58051 | Human fibroblast growth factor receptor (FGFR3) mRNA |
| L03840 | Human fibroblast growth factor receptor 4 (FGFR4) mRNA, complete cds. |
| Y12863 | *Homo sapiens* mRNA for growth factor FIGF; C-fos induced growth factor (VEGF D) |
| U01134 | Human soluble vascular endothelial cell growth factor receptor (sflt) mRNA; vascular endothelial growth factor receptor 1 (VEGFR1); |
| U02687 | Human growth factor receptor tyrosine kinase (STK-1) mRNA; FLK2 |
| X69878 | *H. sapiens* Flt4 mRNA for transmembrane tyrosine kinase; vascular endothelial growth factor receptor 3 precursor (VEGFR3) |
| X16707 | Human fra-1 mRNA; FOS-like antigen-1 |
| NM_005479 | *Homo sapiens* frequently rearranged in advanced T-cell lymphomas (FRAT1) mRNA |
| NM_000510 | *Homo sapiens* follicle stimulating hormone, beta polypeptide (FSHB) |
| M65085 | Human follicle stimulating hormone receptor mRNA |
| AB017363 | *Homo sapiens* mRNA for frizzled-1, complete cds |
| X02492 | Human interferon-inducible mRNA fragment (cDNA 6-16). |
| M32865 | Human Ku protein subunit mRNA; Thyroid autoantigen 70 kD (Ku antigen) |
| U83981 | *Homo sapiens* apoptosis associated protein (GADD34) mRNA |
| M60974 | Human growth arrest and DNA-damage-inducible protein (gadd45) mRNA |

TABLE 13

| | |
|---|---|
| NM_015675 | *Homo sapiens* growth arrest and DNA-damage-inducible, beta (GADD45B) |
| NM_006705 | *Homo sapiens* growth arrest and DNA-damage-inducible, gamma (GADD45G) |
| X01677 | liver glyceraldehyde 3-phosphate dehydrogenase (GAPDH) |
| NM_000805 | *Homo sapiens* gastrin (GAS) |
| J04040 | Human glucagon mRNA, complete cds |
| L20316 | Human glucagon receptor mRNA |
| NM_000515 | *Homo sapiens* growth hormone 1 (GH1) |
| M38451 | Human placenta-specific growth hormone mRNA |
| NM_000163 | *Homo sapiens* growth hormone receptor (GHR) |
| NM_000823 | *Homo sapiens* growth hormone releasing hormone receptor (GHRHR) |
| NM_004122 | *Homo sapiens* growth hormone secretagogue receptor (GHSR) |
| NM_006582 | *Homo sapiens* glucocorticoid modulatory element binding protein 1 (GMEB1) |
| NM_012384 | *Homo sapiens* glucocorticoid modulatory element binding protein 2 (GMEB2) |
| M69013 | Human guanine nucleotide-binding regulatory protein (G-y-alpha) mRNA; Guanine nucleotide binding protein (G protein), alpha 11 (Gq class) |
| L22075 | Human guanine nucleotide regulatory protein (G13) mRNA; Guanine nucleotide binding protein (G protein), alpha 13 |
| NM_004297 | *Homo sapiens* guanine nucleotide-binding protein 14 (GNA14) mRNA |
| M63904 | Human G-alpha 16 protein mRNA, complete cds; Guanine nucleotide binding protein (G protein), alpha 15 (Gq class) |
| X04526 | Human liver mRNA for beta-subunit signal transducing proteins Gs/Gi (beta-G); Guanine nucleotide binding protein (G protein), beta polypeptide 1 |
| M16538 | Human signal-transducing guanine nucleotide-binding regulatory (G) protein beta subunit mRNA; Guanine nucleotide binding protein (G protein), beta polypeptide 2 |
| M24194 | Human MHC protein homologous to chicken B complex protein mRNA; Guanine nucleotide binding protein (G protein), beta polypeptide 2-like 1 |
| M31328 | Human guanine nucleotide-binding protein beta-3 subunit mRNA; Guanine nucleotide binding protein (G protein), beta polypeptide 3 |

TABLE 14

| | |
|---|---|
| AF017656 | *Homo sapiens* G protein beta 5 subunit mRNA; Guanine nucleotide binding protein (G protein), beta 5 |
| U31383 | Human G protein gamma-10 subunit mRNA; Guanine nucleotide binding protein 10 |
| U31384 | Human G protein gamma-11 subunit mRNA; Guanine nucleotide binding protein 11 |
| NM_012202 | *Homo sapiens* guanine nucleotide binding protein (G protein), gamma 3 (GNG3), mRNA |
| AF052149 | *Homo sapiens* clone 24733 mRNA sequence; Guanine nucleotide binding protein (G protein), gamma 3, linked |
| U31382 | Human G protein gamma-4 subunit mRNA; Guanine nucleotide binding protein 4 |
| AF038955 | *Homo sapiens* G protein gamma 5 subunit mRNA; Guanine nucleotide binding protein (G protein), gamma 5 |
| AB010414 | *Homo sapiens* mRNA for G-protein gamma 7; Guanine nucleotide binding protein (G protein), gamma 7 |
| S62027 | transducin gamma subunit; Guanine nucleotide binding protein (G protein), gamma transducing activity polypeptide 1 |
| X01059 | Human placenta mRNA for luteinizing hormone releasing hormone precursor (LHRH). |
| NM_005311 | *Homo sapiens* growth factor receptor-bound protein 10 (GRB10), mRNA |

TABLE 14-continued

| | |
|---|---|
| M96995 | *Homo sapiens* epidermal growth factor receptor-binding protein GRB2 (EGFRBP-GRB2) mRNA sequence |
| M73077 | Human glucocorticoid receptor repression factor 1 (GRF-1) mRNA |
| X12510 | Human mRNA for melanoma growth stimulatory activity (MGSA), groucho |
| X53799 | Human mRNA for macrophage inflammatory protein-2alpha (MIP2alpha,; GRO2 oncogene |
| L33801 | Human protein kinase mRNA; glycogen synthase kinase 3 beta (GSK3 beta); tau kinase subunit; factor A |
| X17644 | Human GST1-Hs mRNA for GTP-binding protein; G1 to S phase transition 1 |
| AF250138 | Protein kinase H11; *Homo sapiens* small stress protein-like protein HSP22 mRNA |
| D49742 | Human mRNA for HGF activator like protein (hyaluronan-binding protein 2) |
| D50405 | Human mRNA for RPD3 protein, Histone deacetylase 1 |
| D16431 | Human mRNA for hepatoma-derived growth factor, complete cds |

TABLE 15

| | |
|---|---|
| M60718 | Human hepatocyte growth factor mRNA (HGF); scatter factor (SF); hepatopoeitin A |
| D14012 | Human mRNA for hepatocyte growth factor (HGF) activator precursor |
| U51004 | *Homo sapiens* protein kinase C inhibitor (PKCI-1) mRNA, Histidine triad nucleotide-binding protein |
| X58536 | Human mRNA for HLA class I locus C heavy chain |
| K01171 | Human HLA-DR alpha-chain mRNA; Class II MHC alpha |
| X02902 | Human mRNA for HLA class II DR-beta 1 (Dw14); Class II MHC beta |
| M11867 | Human MHC class II HLA DR5 DR-beta-chain mRNA, complete cds |
| U40992 | *Homo sapiens* heat shock protein hsp40 homolog mRNA, complete cds; DnaJ-like heat shock protein 40 |

TABLE 16

| | |
|---|---|
| V00530 | Human hypoxanthine-guanine phosphoribosyltransferase (HPRT) IMP: pyrophosphate phosphoribosyltransferase |
| U76376 | *Homo sapiens* activator of apoptosis Hrk (HRK) mRNA; Harakiri, BCL2-interacting protein (contains only BH3 domain) |
| AF068754 | *Homo sapiens* heat shock factor binding protein 1 HSBP1 mRNA; Heat shock factor binding protein 1 |
| AF088982 | *Homo sapiens* heat shock protein hsp40-3 mRNA; Heat shock cognate 40 |
| NM_000196 | *Homo sapiens* hydroxysteroid (11-beta) dehydrogenase 2 (HSD11B2) |
| NM_000862 | *Homo sapiens* hydroxy-delta-5-steroid dehydrogenase, 3 beta- and steroid delta-isomerase 1 (HSD3B1) |
| M64673 | Human heat shock factor 1 (TCF5) mRNA, complete cds; Heat shock transcription factor 1 |
| M65217 | Human heat shock factor 2 (HSF2) mRNA, complete cds; Heat shock transcription factor 2 |
| AB007131 | *Homo sapiens* mRNA for HSF2BP; Heat shock transcription factor 2 binding protein |
| D87673 | *Homo sapiens* mRNA for heat shock transcription factor 4; Heat shock transcription factor 4 |

TABLE 16-continued

| | |
|---|---|
| X63368 | *H. sapiens* HSJ1 mRNA; Heat shock protein, neuronal DNAJ-like 1 |
| L08069 | Human heat shock protein, *E. coli* DnaJ homologue mRNA, complete cds; Heat shock protein, DNAJ-like 2 |
| AB003333 | Molecular cloning, expression and localization of human 105 kDa heat shock protein, hsp105D |
| NM_006597 | *Homo sapiens* heat shock 70 kD protein 10 (HSC71) (HSPA10), mRNA |
| NM_005345 | *Homo sapiens* heat shock 70 kD protein 1 (HSPA1A), mRNA; Heat shock 70 kD protein 1 |
| NM_005346 | *Homo sapiens* heat shock 70 kD protein 1 (HSPA1B), mRNA |
| D85730 | *Homo sapiens* HSPA1L mRNA for Heat shock protein 70 testis variant, complete cds; Heat shock 70 kD protein-like 1 |
| U56725 | Human heat shock protein mRNA, complete cds; Heat shock 70 kD protein 2 |
| L12723 | Human heat shock protein 70 (hsp70) mRNA; Heat shock 70 kD protein 4 |
| X87949 | *H. sapiens* mRNA for BiP protein; Heat shock 70 kD protein 5 (glucose-regulated protein, 78 kD) |
| X51758 | Human mRNA for heat shock protein HSP70B'; Heat shock 70 kD protein 6 |

TABLE 17

| | |
|---|---|
| L15189 | *Homo sapiens* mitochondrial HSP75 mRNA; Heat shock 70 kD protein 9B (mortalin-2) |
| X54079 | Human mRNA for heat shock protein HSP27; Heat shock 27 kD protein 1 |
| D89617 | *Homo sapiens* mRNA for MKBP; Heat shock 27 kD protein 2 |
| U15590 | *Homo sapiens* heat shock 17 kD protein 3 (HSPB3) mRNA, complete cds; Heat shock 27 kD protein 3 |
| AJ243191 | *Homo sapiens* mRNA for cardiovascular heat shock protein; Heat shock 27 kD protein family, member 7 (cardiovascular) |
| AF028832 | *Homo sapiens* Hsp89-alpha-delta-N mRNA; Heat shock 90 kD protein 1, alpha |
| M16660 | Human 90-kDa heat-shock protein gene, cDNA; Heat shock 90 kD protein 1, beta |
| M34664 | Heat shock 60 kD protein 1 (chaperonin) |
| U07550 | Human chaperonin 10 mRNA; Heat shock 10 kD protein 1 |
| D49547 | Human mRNA for heat-shock protein 40; Heat shock 40 kD protein 1 |
| AF012106 | *Homo sapiens* DnaJ protein (HSPF2) mRNA, complete cds; Heat shock 40 kD protein 2 |
| J03132 | Human intercellular adhesion molecule-1 (ICAM-1) mRNA, CD54 |
| M91196 | *Homo sapiens* DNA-binding protein mRNA (Interferon consensus sequence binding protein 1) |
| NM_005531 | *Homo sapiens* interferon, gamma-inducible protein 16 (IFI16) mRNA |
| X67325 | *H. sapiens* p27 mRNA (interferon, alpha-inducible protein 27) |
| J03909 | Human gamma-interferon-inducible protein (IP-30) mRNA, complete cds |
| X03557 | Human mRNA for 56-KDa protein induced by interferon |
| AF083470 | *Homo sapiens* interferon induced tetratricopeptide protein IFI60 (IFIT4) mRNA, complete cds |
| J04164 | Human interferon-inducible protein 9-27 mRNA, complete cds |
| X57351 | Human 1-8D gene from interferon-inducible gene family |
| X57352 | Human 1-8U gene from interferon-inducible gene family |
| V00551 | Messenger RNA for human leukocyte (alpha) interferon |

TABLE 17-continued

| | |
|---|---|
| V00538 | Messenger RNA for human leukocyte (alpha) interferon |
| V00542 | Messenger RNA for human leukocyte (alpha) interferon |
| M28585 | Human leukocyte interferon-alpha mRNA, complete cds, clone pIFN105 |
| M54886 | Human interferon-alpha mRNA, complete cds |
| V00540 | Messenger RNA for human leukocyte (alpha) interferon |
| V00541 | Messenger RNA for human leukocyte interferon (one of eight). |
| V00550 | Messenger RNA for human leukocyte (alpha) interferon. |

TABLE 18

| | |
|---|---|
| J03171 | Human interferon-alpha receptor (HuIFN-alpha-Rec) mRNA, complete cds |
| X77722 | *H. sapiens* mRNA for interferon alpha/beta receptor |
| V00547 | Human messenger RNA for fibroblast (beta) interferon |
| X13274 | Human mRNA for interferon IFN-gamma |
| J03143 | Human interferon-gamma receptor mRNA, complete cds |
| U05875 | Human clone pSK1 interferon gamma receptor accessory factor-1 (AF-1) mRNA, complete cds |
| X02669 | Human mRNA for type 1 interferon-omega 1. |
| Y08915 | Immunoglobulin (CD79A) binding protein 1 |
| X57025 | Human IGF-I mRNA for insulin-like growth factor I |
| X04434 | Human mRNA for insulin-like growth factor I receptor |
| J03242 | Human insulin-lke growth factor II mRNA, complete cds |
| J03528 | Human cation-independent mannose 6-phosphate receptor mRNA; insulin-like growth factor II receptor |
| M31145 | Human insulin-like growth factor binding protein mRNA, complete cds |
| M35410 | Human insulin-like growth factor binding protein 2 (IGFBP2) mRNA |
| M31159 | Human growth hormone-dependent insulin-like growth factor-binding protein mRNA, complete cds |
| M62403 | Human insulin-like growth factor binding protein 4 (IGFBP4) mRNA, complete cds |
| AF055033 | *Homo sapiens* clone 24645 insulin-like growth factor binding protein 5 (IGFBP5) mRNA, complete cds |
| M62402 | Human insulin-like growth factor binding protein 6 (IGFBP6) mRNA, complete cds |
| S75725 | prostacyclin-stimulating factor [human, cultured diploid fibroblastcells, mRNA, 1124 nt]. |
| AF044195 | *Homo sapiens* IkappaB kinase complex associated protein (IKAP) mRNA, complete cds; IKKAP2 |
| AF080158 | *Homo sapiens* IkB kinase-b (IKK-beta) mRNA, IKK2/beta; IKK2 |
| AF074382 | *Homo sapiens* IkB kinase gamma subunit (IKK-gamma) mRNA, NLK |
| M57627 | Human interleukin 10 (IL10) mRNA, complete cds |
| U00672 | Human interleukin-10 receptor mRNA, complete cds |
| Z17227 | *Homo sapiens* mRNA for transmembrane receptor protein |
| M57765 | Human interleukin 11 mRNA, complete cds |

TABLE 19

| | |
|---|---|
| Z38102 | *H. sapiens* mRNA for interleukin-11 receptor |
| M65291 | Human natural killer cell stimulatory factor (NKSF) mRNA, complete cds, clone p35 |
| M65290 | Human natural killer cell stimulatory factor (NKSF) mRNA, complete cds, clone p40 |
| U03187 | Human IL12 receptor component mRNA, complete cds |
| U64198 | Human Il-12 receptor beta2 mRNA, complete cds |
| L06801 | *Homo sapiens* interleukin 13 mRNA, complete cds |
| Y09328 | *H. sapiens* mRNA for IL13 receptor alpha-1 chain |
| U70981 | Human interleukin-13 receptor mRNA, complete cds |
| AF070546 | *Homo sapiens* clone 24607 mRNA sequence |
| AF031167 | *Homo sapiens* interleukin 15 precursor (IL-15) mRNA, complete cds. |
| U31628 | Human interleukin-15 receptor alpha chain precursor (IL15RA) mRNA, complete cds |
| M90391 | *Homo sapiens* putative IL-16 protein precursor, mRNA, complete cds |
| NM_014443 | *Homo sapiens* interleukin 17B (IL17B), mRNA |
| NM_013278 | *Homo sapiens* interleukin 17C (IL17C), mRNA |
| U58917 | *Homo sapiens* IL-17 receptor mRNA, complete cds |
| D49950 | *Homo sapiens* mRNA for interferon-gamma inducing factor (IGIF), complete cds |
| AB019504 | *Homo sapiens* mRNA for interleukin-18 binding protein, complete cds |
| U43672 | Human putative transmembrane receptor IL-1Rrp mRNA, complete cds |
| NM_013371 | *Homo sapiens* interleukin 19 (IL19), mRNA |
| X02531 | Human mRNA for interleukin 1-alpha |
| M15330 | Human interleukin 1-beta (IL1B) mRNA, complete cds |
| M27492 | Human interleukin 1 receptor mRNA, complete cds |
| X59770 | *H. sapiens* IL-1R2 mRNA for type II interleukin-1 receptor, (cell line CB23). |
| D12763 | *Homo sapiens* mRNA for ST2 protein |

TABLE 20

| | |
|---|---|
| U49065 | Human interleukin-1 receptor-related protein mRNA, complete cds |
| X53296 | *H. sapiens* mRNA for IRAP |
| V00564 | Human mRNA encoding interleukin-2 (IL-2) a lymphozyte regulatory molecule |
| X01057 | Human mRNA for interleukin-2 receptor |
| M26062 | Human interleukin 2 receptor beta chain (p70-75) mRNA, complete cds |
| D11086 | Human mRNA for interleukin 2 receptor gamma chain |
| M17115 | Human multilineage-colony-stimulating factor mRNA, complete cds |
| M74782 | Human interleukin 3 receptor (hIL-3Ra) mRNA, complete cds |
| M13982 | Human interleukin 4 (IL-4) mRNA, complete cds |
| X52425 | Human IL-4-R mRNA for the interleukin 4 receptor |
| X04688 | Human mRNA for T-cell replacing factor (interleukin-5). |
| M75914 | Human interleukin 5 receptor alpha mRNA, complete cds |
| M14584 | Human interleukin 6 mRNA, complete cds |
| X12830 | Human mRNA for interleukin-6 (IL-6) receptor |
| M57230 | Human membrane glycoprotein gp130 mRNA, Interleukin 6 signal transducer (oncostatin M receptor) |

TABLE 20-continued

| | |
|---|---|
| J04156 | Human interleukin 7 (IL-7) mRNA, complete cds |
| M29696 | Human interleukin-7 receptor (IL-7) mRNA, complete cds |
| M17017 | Human beta-thromboglobulin-like protein mRNA, complete cds |
| L19591 | *Homo sapiens* interleukin 8 receptor alpha (IL8RA) mRNA, complete cds |
| L19593 | *Homo sapiens* interleukin 8 receptor beta (IL8RB) mRNA, complete cds |
| M30134 | Human P40 protein mRNA, complete cds |
| M84747 | Human interleukin 9 receptor mRNA, complete cds. |
| U58198 | Human interleukin enhancer binding factor 3 mRNA |
| X60787 | Human mRNA for transcription factor ILF |
| U10323 | Human nuclear factor NF45 mRNA, complete cds |
| U10324 | Human nuclear factor NF90 mRNA, complete cds |
| AF001954 | *Homo sapiens* growth inhibitor p33ING1 (ING1) mRNA, complete cds |
| NM_001564 | *Homo sapiens* inhibitor of growth family, member 1-like (ING1L) mRNA |
| NM_000207 | *Homo sapiens* insulin (INS), mRNA |
| NM_005542 | *Homo sapiens* insulin induced gene 1 (INSIG1) |
| NM_000208 | *Homo sapiens* insulin receptor (INSR), mRNA. |
| M10051 | Human insulin receptor mRNA, complete cds |
| J05046 | Human insulin receptor-related receptor (IRR) mRNA, 3' end |
| NM_000209 | *Homo sapiens* insulin promoter factor 1, homeodomain transcription factor (IPF1) |

TABLE 21

| | |
|---|---|
| L76191 | *Homo sapiens* interleukin-1 receptor-associated kinase (IRAK) mRNA, complete cds |
| AF026273 | *Homo sapiens* interleukin-1 receptor-associated kinase-2 mRNA, complete cds |
| X14454 | Human mRNA for interferon regulatory factor 1 |
| X15949 | Human mRNA for interferon regulatory factor-2 (IRF-2). |
| Z56281 | *H. sapiens* mRNA for interferon regulatory factor 3 |
| U52682 | Human lymphocyte specific interferon regulatory factor/interferon regulatory factor 4 (LSIRF/IRF4) mRNA, complete cds |
| U51127 | Human interferon regulatory factor 5 (Humirf5) mRNA, complete cds |
| AF027292 | *Homo sapiens* interferon regulatory factor 6 (IRF6) mRNA, complete cds |
| U53830 | *Homo sapiens* interferon regulatory factor 7A mRNA, complete cds |
| S62539 | insulin receptor substrate-1 [human, skeletal muscle, mRNA, 5828 nt]. |
| S62539 | insulin receptor substrate-1 [human, skeletal muscle, mRNA, 5828 nt]. |
| NM_003749 | *Homo sapiens* insulin receptor substrate 2 (IRS2) |
| NM_003604 | *Homo sapiens* insulin receptor substrate 4 (IRS4) |
| M13755 | Human interferon-induced 17-kDa/15-kDa protein mRNA (interferon-stimulated protein, 15 kDa) |
| U88964 | Human HEM45 mRNA, complete cds |
| M87503 | Human IFN-responsive transcription factor subunit mRNA; Interferon-stimulated transcription factor 3, gamma (48 kD); p48 |

TABLE 22

| | |
|---|---|
| L12002 | Human integrin alpha 4 subunit mRNA, complete cds; Integrin, alpha 4 (antigen CD49D, alpha 4 subunit of VLA-4 receptor) |
| Y00796 | Human mRNA for leukocyte-associated molecule-1 alpha subunit (LFA-1 alpha subunit)., CD11a |
| J03925 | Integrin, alpha M (complement component receptor 3, alpha; also known as CD11b (p170), macrophage antigen alpha polypeptide) |
| X07979 | Integrin, beta 1 (fibronectin receptor, beta polypeptide, antigen CD29 includes MDF2, MSK12); |
| M15395 | Human leukocyte adhesion protein (LFA-1/Mac-1/p150, 95 family) beta subunit mRNA, CD18 |
| AF049893 | *Homo sapiens* insulin upstream factor 1 (IUF1) mRNA |
| M64174 | Human protein-tyrosine kinase (JAK1) mRNA, Janus kinase 1 |
| AF005216 | *Homo sapiens* receptor-associated tyrosine kinase (JAK2) mRNA, Janus kinase 2 |
| U09607 | Human JAK family protein tyrosine kinase (JAK3) mRNA, complete cds |
| NM_002228 | *Homo sapiens* v-jun avian sarcoma virus 17 oncogene homolog (JUN) mRNA. |
| K00558 | human alpha-tubulin mRNA, complete cds |
| AF039597 | Ku86 autoantigen related protein 1 |
| X61656 | *H. sapiens* mRNA for growth factor receptor tyrosine kinase; Kinase insert domain receptor (a type III receptor tyrosine kinase) |
| AB034989 | KIAA0025 gene product; MMS-inducible gene; *Homo sapiens* mRNA for stress protein Herp |
| D23673 | Human mRNA, clone HH109 (screened by the monoclonal antibody of insulin receptor substrate-1 (IRS-1)). |
| M59964 | Human stem cell factor mRNA; (SCF); mast cell growth factor (MGF); c-kit ligand (KITLG) |
| AF036905 | *Homo sapiens* linker for activation of T cells (LAT) mRNA |
| M36881 | Human lymphocyte-specific protein tyrosine kinase (lck) mRNA |
| NM_000894 | *Homo sapiens* luteinizing hormone beta polypeptide (LHB) |
| M73746 | *Homo sapiens* lutropin/choriogonadotropin receptor (LHCGR) mRNA |
| M13451 | Human lamin C mRNA, complete cds, Lamin A |
| M34458 | Human lamin B mRNA, complete cds, |
| M94362 | Human lamin B2 (LAMB2) mRNA, partial cds |
| NM_016103 | *Homo sapiens* GTP-binding protein Sara (LOC51128) mRNA |
| AF125392 | *Homo sapiens* insulin induced protein 2 mRNA, complete cds |
| AF119666 | *Homo sapiens* insulin receptor tyrosine kinase substrate mRNA |

TABLE 23

| | |
|---|---|
| D12614 | Human mRNA for lymphotoxin (TNF-beta), complete cds |
| U77352 | *Homo sapiens* MAP kinase-activating death domain protein (MADD) mRNA |
| U68018 | Human mad protein homolog (hMAD-2) mRNA; JV18-1.MADR2 OR SMAD2 |
| U68019 | *Homo sapiens* mad protein homolog (hMAD-3) mRNA, complete cds |
| U44378 | Human homozygous deletion target in pancreatic carcinoma (DPC4); mothers against dpp homolog 4 (SMAD4) |
| AF035528 | *Homo sapiens* Smad6 mRNA, complete cds |
| AF010193 | *Homo sapiens* MAD-related gene SMAD7 (SMAD7) mRNA complete cds |
| NM_000240 | *Homo sapiens* monoamine oxidase A (MAOA), nuclear gene encoding mitochondrial protein, mRNA |
| M69177 | Human monoamine oxidase B (MAOB) mRNA, complete cds |
| L11284 | *Homo sapiens* ERK activator kinase (MEK1) mRNA |
| L11285 | *Homo sapiens* ERK activator kinase (MEK2) mRNA |

TABLE 23-continued

| | |
|---|---|
| D87116 | Human mRNA for MAP kinase kinase 3b, complete cds, MEK3 |
| U17743 | Human JNK activating kinase (JNKK1) mRNA, complete cds; SEK1 |
| U39064 | Human MAP kinase kinase 6 mRNA, complete cds; MEK6 |
| AF013588 | *Homo sapiens* mitogen-activated protein kinase kinase 7 (MKK7) mRNA, complete cds |
| AF042838 | *Homo sapiens* MEK kinase 1 (MEKK1) mRNA, partial cds |
| Y10256 | *H. sapiens* mRNA for serine/threonine protein kinase, NIK |
| NM_003188 | *Homo sapiens* mitogen-activated protein kinase kinase kinase 7 (MAP3K7), mRNA, TAK1 |
| AF096300 | *Homo sapiens* HPK/GCK-like kinase HGK mRNA, complete cds |
| M84489 | Human extracellular signal-regulated kinase 2 mRNA; ERK2 |
| U92268 | *Homo sapiens* mitogen activated protein kinase p38-2 mRNA, complete cds |
| X79483 | *H. sapiens* ERK6 mRNA for extracellular signal regulated kinase |
| X79483 | *H. sapiens* ERK6 mRNA for extracellular signal regulated kinase |
| AF004709 | *Homo sapiens* stress-activated protein kinase 4 (SAPK4) mRNA, complete cds |

TABLE 24

| | |
|---|---|
| L35253 | Human p38 mitogen activated protein (MAP) kinase mRNA; cytokine suppressive anti-inflammatory drug binding protein (CSAID binding protein; CSBP); MAX-interacting protein 2 (MXI2) |
| L35253 | Human p38 mitogen activated protein (MAP) kinase mRNA; cytokine suppressive anti-inflammatory drug binding protein (CSAID binding protein; CSBP); MAX-interacting protein 2 (MXI2) |
| X60188 | Human ERK1 mRNA for protein serine/threonine kinase |
| L26318 | Human protein kinase (JNK1) mRNA; SAPK |
| X60287 | *H. sapiens* max mRNA |
| NM_000529 | *Homo sapiens* melanocortin 2 receptor (adrenocorticotropic hormone) |
| M92424 | Human homolog of mouse-double-minute 2; p53-associated mdm2 protein |
| AF007111 | MDM2-like p53-binding protein (MDMX) |
| NM_002415 | *Homo sapiens* macrophage migration inhibitory factor (glycosylation-inhibiting factor) (MIF), |
| X72755 | *H. sapiens* Humig mRNA |
| AB014888 | *Homo sapiens* mRNA for MRJ |
| X70040 | *H. sapiens* RON mRNA for tyrosine kinase; Macrophage stimulating 1 receptor (c-met-related tyrosine kinase) |
| M30817 | Human interferon-induced cellular resistance mediator protein (MxA)mRNA |
| M30818 | Human interferon-induced cellular resistance mediator protein (MxB) mRNA |
| U70451 | Human myeloid differentiation primary response protein MyD88 mRNA, complete cds |
| NM_000261 | *Homo sapiens* myocilin, trabecular meshwork inducible glucocorticoid response (MYOC) |
| AF058696 | Nijmegen breakage syndrome 1 (nibrin) |
| U08015 | Human NF-ATc mRNA, complete cds |
| U43341 | Human transcription factor NFAT1 isoform B (NFAT1) mRNA, complete cds |
| L41067 | *Homo sapiens* NF-AT4c mRNA, complete cds |
| L41066 | *Homo sapiens* NF-AT3 mRNA, complete cds |
| U26173 | Human bZIP protein NF-IL3A (IL3BP1) mRNA, complete cds |
| M58603 | Human nuclear factor kappa-B DNA binding subunit (NF-kappa-B) mRNA, p105 |
| X61498 | *H. sapiens* mRNA for NF-kB subunit (p49/p100) |
| M69043 | *Homo sapiens* MAD-3 mRNA encoding IkB-like activity, complete cds, IkBalpha |
| L40407 | *Homo sapiens* thyroid receptor interactor (TRIP9) gene, complete cds |

TABLE 25

| | |
|---|---|
| U91616 | Human I kappa B epsilon (IkBe) mRNA, complete cds |
| X77909 | *H. sapiens* IKBL mRNA |
| U16258 | Human I kappa BR mRNA, complete cds |
| U08191 | Human R kappa B mRNA, complete cds |
| X52599 | Human mRNA for beta nerve growth factor |
| M14764 | Human nerve growth factor receptor mRNA |
| D50420 | Non-histone chromosome protein 2 (*S. cerevisiae*)-like 1 |
| U17327 | Human neuronal nitric oxide synthase (NOS1) mRNA |
| U20141 | Human inducible nitric oxide synthase mRNA |
| M93718 | Human nitric oxide synthase mRNA (endothelial) |
| M10901 | Human glucocorticoid receptor alpha mRNA, complete cds |
| L12260 | Human recombinant glial growth factor 2 mRNA, complete cds and flanking regions (neuregulin 1) |
| M86528 | Human neurotrophin-4 (NT-4) gene; neurotrophin 5 (neurotrophin 4/5) (NTF5) |
| U46752 | Oxidative stress induced like; Human phosphotyrosine independent ligand p62B B-cell isoform for the Lck SH2 domain mRNA, partial cds |
| M25650 | Human oxytocin mRNA |
| X64878 | *H. sapiens* mRNA for oxytocin receptor |
| AF000546 | *Homo sapiens* purinergic receptor P2Y5 mRNA |
| U24152 | Human p21-activated protein kinase (PAK-alpha; PAK1) |
| U24153 | Human p21-activated protein kinase (PAK-gamma; PAK2); PAK65; S6/H4 kinase |
| U41745 | Human PDGF associated protein mRNA (PAP) |
| NM_002592 | *Homo sapiens* proliferating cell nuclear antigen (PCNA) mRNA |
| AF100928 | *Homo sapiens* apoptosis-inducing factor AIF mRNA, nuclear gene encoding mitochondrial protein; Programmed cell death 8 |
| X06374 | Human platelet-derived growth factor A subunit precursor (PDGFA; PDGF-1) |
| M21574 | Human platelet-derived growth factor receptor alpha (PDGFRA) mRNA; CD140A antigen |

TABLE 26

| | |
|---|---|
| M21616 | Human platelet-derived growth factor receptor mRNA (PDGFRB); CD140B antigen |
| M28526 | Platelet/endothelial cell adhesion molecule (CD31 antigen), neutrophil; CD31 |
| NM_006211 | *Homo sapiens* proenkephalin (PENK), mRNA |
| X54936 | *H. sapiens* mRNA for placenta growth factor (PIGF). |
| AF010310 | p53 induced protein (Proline oxidase homolog) |
| Y13367 | *H. sapiens* mRNA for phosphoinositide 3-kinase; Phosphoinositide-3-kinase, class 2, alpha polypeptide |
| Y11312 | *H. sapiens* mRNA for phosphoinositide 3-kinase, Phosphoinositide-3-kinase, class 2, beta polypeptide |
| AJ000008 | *Homo sapiens* mRNA for C2 domain containing PI3-kinase, phosphoinositide-3-kinase, class 2, gamma polypeptide |
| Z46973 | *H. sapiens* mRNA for phosphatidylinositol 3-kinase, Phosphoinositide-3-kinase, class 3 |
| U79143 | Human phosphoinositide 3'-hydroxykinase p110-alpha subunit mRNA, Phosphoinositide-3-kinase, catalytic, alpha polypeptide |
| S67334 | phosphatidylinositol 3-kinase p110 beta isoform = 110 kda catalytic subunit [human, mRNA Partial, 3213 nt]. Phosphoinositide-3-kinase, catalytic, beta polypeptide |
| U86453 | Human phosphatidylinositol 3-kinase catalytic subunit p110delta mRNAPhosphoinositide-3-kinase, catalytic, delta polypeptide |
| X83368 | *H. sapiens* mRNA for phosphatidylinositol 3 kinase gamma, Phosphoinositide-3-kinase, catalytic, gamma polypeptide |
| M61906 | Human P13-kinase associated p85, Phosphoinositide-3-kinase, regulatory subunit, polypeptide 1 (p85 alpha) |

TABLE 26-continued

| | |
|---|---|
| X80907 | *H. sapiens* mRNA for p85 beta subunit of phosphatidyl-inositol-3-kinase, Phosphoinositide-3-kinase, regulatory subunit, polypeptide 2 (p85 beta) |
| D88532 | *Homo sapiens* mRNA for p55pik, Phosphoinositide-3-kinase, regulatory subunit, polypeptide 3 (p55, gamma) |
| Y08991 | *H. sapiens* mRNA for adaptor protein p150, Phosphoinositide-3-kinase, regulatory subunit 4 |
| M72393 | Human calcium-dependent phosphplipid-binding protein (PLA2) mRNA; Phospholipase A2, group IVA (cytosolic) |
| NM_003560 | *Homo sapiens* phospholipase A2, group VI (cytosolic, calcium-independent) (PLA2G6) |
| AF019770 | *Homo sapiens* macrophage inhibitory cytokine-1 (MIC-1) mRNA (prostate differentiation factor) |

TABLE 27

| | |
|---|---|
| M95678 | *Homo sapiens* phospholipase C-beta-2 mRNA; Phospholipase C, beta 2 |
| Z16411 | *H. sapiens* mRNA encoding phospholipase c; Phospholipase C, beta 3 (phosphatidylinositol-specific) |
| L41349 | *Homo sapiens* phospholipase C beta 4 (PLCB4) mRNA; Phospholipase C, beta 4 |
| M34667 | Human phospholipase C-gamma mRNA, complete cds |
| X05199 | Human mRNA for plasminogen |
| J03727 | Human phenylethanolamine N-methyltransferase mRNA, complete cds |
| NM_000939 | *Homo sapiens* proopiomelanocortin (adrenocorticotropin/oeta-lipotropin/alpha-melanocyte stimulating hormone/beta-melanocyte stimulating hormone/beta-endorphin) (POMC) |
| NM_000306 | *Homo sapiens* POU domain, class 1, transcription factor 1 (Pit1, growth hormone factor 1) (POU1F1) |
| L14778 | Human calmodulin-dependent protein phosphatase catalytic subunit (PPP3CA) mRNA, complete cds and alternative exon |
| M29551 | Human calcineurin A2 mRNA; |
| S46622 | calcineurin A catalytic subunit [human, testis, mRNA, 2134 nt]; Protein phosphatase 3 (formerly 2B), catalytic subunit, gamma isoform (calcineurin A gamma) |
| M28393 | Human perforin mRNA, complete cds |
| X52479 | Human PKC alpha mRNA for protein kinase C alpha; Protein kinase C, alpha |
| AL049654 | Novel human mRNA similar to mouse gene PICK1; Protein kinase C, alpha binding protein |
| X06318 | Human mRNA for protein kinase C (PKC) type beta I.; Protein kinase C, beta 1 |
| U48251 | *Homo sapiens* protein kinase C-binding protein RACK7 mRNA, partial cds; Protein kinase C binding protein 1 |
| U48250 | Human protein kinase C-binding protein RACK17 mRNA, partial cds; Protein kinase C binding protein 2 |
| D10495 | *Homo sapiens* mRNA for protein kinase C delta-type; Protein kinase C, delta |
| X65293 | *H. sapiens* mRNA for protein kinase C-Epsilon; Protein kinase C, epsilon |
| Z15114 | *H. sapiens* mRNA for protein kinase C gamma (partial); Protein kinase C, gamma |
| M55284 | Human protein kinase C-L (PRKCL) mRNA; Protein kinase C, eta |
| L18964 | Human protein kinase C iota isoform (PRKCI) mRNA; Protein kinase C, iota |
| D26181 | Human mRNA for novel protein kinase PKN; Protein kinase C-like 1 |
| U33052 | Human lipid-activated, protein kinase PRK2 mRNA; Protein kinase C-like 2 |
| X75756 | *H. sapiens* mRNA for protein kinase C mu; Protein kinase C, mu |

TABLE 27-continued

| | |
|---|---|
| AB015982 | *Homo sapiens* EPK2 mRNA for serine/threonine kinase; Protein kinase C, nu |

TABLE 28

| | |
|---|---|
| L07032 | Human protein kinase C theta (PKC) mRNA; Protein kinase C, theta |
| J03075 | Human 80K-H protein (kinase C substrate) mRNA; Protein kinase C substrate 80K-H |
| Z15108 | *H. sapiens* mRNA for protein kinase C zeta; Protein kinase C, zeta |
| U47077 | *Homo sapiens* DNA-dependent protein kinase catalytic subunit (DNA-PKcs) mRNA |

TABLE 29

| | |
|---|---|
| M59979 | prostaglandin G/H synthase 1 precursor (PGH synthase 1; PGHS1; PTGS1); cyclooxygenase 1 (COX1) |
| M90100 | prostaglandin G/H synthase 2 precursor (PGH synthase 2; PGHS2; PTGS2); cyclooxygenase 2 (COX2) |
| D13540 | *Homo sapiens* SH-PTP3 mRNA for protein-tyrosine phosphatase; Protein tyrosine phosphatase, non-receptor type 11; Shp2 |
| D21210 | Human mRNA for protein tyrosine phosphatase (PTP-BAS, type 2); Protein tyrosine phosphatase, non-receptor type 13 (APO-1/CD95 (Fas)-associated phosphatase); FAP |
| X62055 | *H. sapiens* PTP1C mRNA for protein-tyrosine phosphatase 1C.; Protein tyrosine phosphatase, non-receptor type 6; SHP-1 |
| D11327 | Human mRNA for protein-tyrosine phosphatase; Protein tyrosine phosphatase, non-receptor type 7, HePTP |
| Y00062 | Human mRNA for T200 leukocyte common antigen (CD45, LC-A). |
| AF060231 | *Homo sapiens* herpesvirus entry protein C (HVEC) mRNA; Poliovirus receptor-related 1 (herpesvirus entry mediator C); nectin) |
| M29870 | Human ras-related C3 botulinum toxin substrate (rac) mRNA ras-related C3 botulinum toxin substrate 1; p21-rac1; ras-like protein TC25 |
| M29871 | Human ras-related C3 botulinum toxin substrate (rac) mRNA; p21-rac2; small G protein |
| Z75311 | RAD50 (*S. cerevisiae*) homolog |
| AF029670 | RAD51 (*S. cerevisiae*) homolog C |
| AF086904 | Protein kinase Chk2 |
| M23379 | Human GTPase-activating protein ras p21 (RASA) mRNA; GAP |
| M15400 | Human retinoblastoma susceptibility mRNA, complete cds (RB1) |
| NM_002892 | *Homo sapiens* retinoblastoma-binding protein 1 (RBBP1) mRNA |
| S66431 | RBP2 = retinoblastoma binding protein 2 [human, Nalm-6 pre-B cell leukemia, mRNA, 6455 nt]. |
| X74262 | Human chromatin assembly factor 1 p48 subunit (CAF1 p48 subunit); retinoblastoma-binding protein 4 |
| X85134 | *H. sapiens* RBQ-3 mRNA |
| X85133 | *H. sapiens* RBQ-1 mRNA |
| U35143 | Human retinoblastoma-binding protein (RbAp46) mRNA, complete cds |
| AF043431 | *Homo sapiens* retinoblastoma-interacting protein (RBBP8) mRNA, complete cds |

TABLE 30

| | |
|---|---|
| AF039564 | *Homo sapiens* retinoblastoma binding protein (RBBP9) mRNA, complete cds. |

TABLE 30-continued

| | |
|---|---|
| L14812 | Human retinoblastoma related protein (p107) mRNA; Retinoblastoma-like 1 |
| X74594 | Human retinoblastoma-like protein 2 (RBL2; RB2); 130-kDa retinoblastoma-associated protein (p130) |
| L19067 | Human NF-kappa-B transcription factor p65 subunit mRNA, complete cds. |
| M83221 | *Homo sapiens* I-Rel mRNA, complete cds. |
| NM_000537 | *Homo sapiens* renin (REN) |
| AF037195 | *Homo sapiens* regulator of G protein signaling RGS14 mRNA, complete cds. |
| U50062 | *Homo sapiens* RIP protein kinase mRNA, Receptor (TNFRSF)-interacting serine-threonine kinase 1 |
| AF027706 | *Homo sapiens* serine/threonine kinase RICK (RICK) mRNA; RIP2 |
| M63488 | Replication protein A1 (70 kD) |
| X56932 | *H. sapiens* mRNA for 23 kD highly basic protein |
| U14971 | Human ribosomal protein S9 mRNA, complete cds |
| AF020044 | *Homo sapiens* lymphocyte secreted C-type lectin precursor, mRNA, complete cds |
| M57502 | Human secreted protein (I-309) mRNA; Small inducible cytokine A1 (I-309, homologous to mouse Tca-3) |
| D49372 | Human mRNA for eotaxin; Small inducible cytokine subfamily A (Cys-Cys), member 11 (eotaxin) |
| U59808 | Human monocyte chemotactic protein-4 precursor (MCP-4) mRNA; Small inducible cytokine subfamily A (Cys-Cys), member 13 |
| Z49270 | *H. sapiens* mRNA for chemokine HCC-1; Small inducible cytokine subfamily A (Cys-Cys), member 14 |
| AF031587 | *Homo sapiens* MIP-1 delta mRNA; Small inducible cytokine subfamily A (Cys-Cys), member 15 |
| AF039955 | *Homo sapiens* liver CC chemokine-1 precursor (SCYA16) mRNA; Small inducible cytokine subfamily A, member 16 |
| D43767 | Human mRNA for chemokine; Small inducible cytokine subfamily A (Cys-Cys), member 17 |
| Y13710 | *Homo sapiens* mRNA for alternative activated macrophage specific CC chemokine 1; Small inducible cytokine subfamily A (Cys-Cys), member 18, pulmonary and activation-regulated |
| U77180 | Human macrophage inflammatory protein 3 beta (MIP-3beta), Small inducible cytokine subfamily A (Cys-Cys), member 19 |
| S71513 | monocyte chemoattractant protein-1 [human, mRNA, 739 nt], MCP-1 |

TABLE 31

| | |
|---|---|
| U77035 | Human macrophage inflammatory protein 3 alpha (MIP-3a) mRNA; Small inducible cytokine subfamily A (Cys-Cys), member 20 |
| AF001979 | *Homo sapiens* beta chemokine mRNA; Small inducible cytokine subfamily A (Cys-Cys), member 21 |
| U83171 | Human macrophage-derived chemokine precursor (MDC) mRNA; Small inducible cytokine subfamily A (Cys-Cys), member 22 |
| U58913 | Human chemokine (hmrp-2a) mRNA; small inducible cytokine subfamily A (Cys-Cys), member 23 |
| U85768 | Human myeloid progenitor inhibitory factor-1 MPIF-2 mRNA |

TABLE 32

| | |
|---|---|
| U86358 | Human chemokine (TECK) mRNA; Small inducible cytokine subfamily A (Cys-Cys), member 25 |
| AB010447 | *Homo sapiens* mRNA for CC chemokine eotaxin3; Small inducible cytokine subfamily A (Cys-Cys), member 26 |

TABLE 32-continued

| | |
|---|---|
| AJ243542 | *Homo sapiens* mRNA for CCL27 chemokine, small inducible cytokine subfamily A (Cys-Cys), member 27 |
| M23452 | Human macrophage inflammatory protein (G0S19-1) mRNA, Small inducible cytokine subfamily A (Cys-Cys), member 3; Mip-1a |
| J04130 | Human activation (Act-2) mRNA, complete cds |
| M21121 | Human T cell-specific protein (RANTES) mRNA, Small inducible cytokine A5 |
| X72308 | *Homo sapiens* mRNA for monocyte chemotactic protein-3 (MCP-3), Small inducible cytokine A7 (monocyte chemotactic protein 3) |
| Y10802 | *H. sapiens* mRNA for monocyte chemotactic protein 2 |
| X02530 | Human mRNA for gamma-interferon inducible early response gene (with homology to platelet proteins). |
| AF030514 | *Homo sapiens* interferon stimulated T-cell alpha chemoattractant precursor, mRNA, complete cds |
| AF073957 | *Homo sapiens* CXC chemokine BRAK mRNA, Small inducible cytokine subfamily B (Cys-X-Cys), member 14 |
| X78686 | *H. sapiens* ENA-78 mRNA; Small inducible cytokine subfamily B (Cys-X-Cys), member 5 (epithelial-derived neutrophil-activating peptide 78) |
| U81234 | Human chemokine alpha 3 (CKA-3) mRNA; small inducible cytokine subfamily B (Cys-X-Cys), member 6 (granulocyte chemotactic protein 2) |
| D43768 | numan mRNA for SCM-1 (single cysteine motif-1); Small inducible cytokine subfamily C, member 1 (lymphotactin) |
| NM_003175 | *Homo sapiens* small inducible cytokine subfamily C, member 2 (SCYC2), mRNA. |
| U84487 | Human CX3C chemokine precursor, mRNA, alternatively spliced, complete cds |
| U10117 | Human endothelial-monocyte activating polypeptide II mRNA; small inducible cytokine subfamily E, member 1 (endothelial monocyte-activating) |
| L36033 | Human pre-B cell stimulating factor homologue (SDF1b) mRNA, complete cds; Stromal cell-derived factor 1 |
| M30640 | selectin E (endothelial adhesion molecule 1) |
| M25280 | selectin L (lymphocyte adhesion molecule 1) |

TABLE 33

| | |
|---|---|
| M25322 | selectin P (granule membrane protein 140 kD, antigen CD62) |
| U02297 | selectin P ligand |
| X68148 | *H. sapiens* SHC mRNA, Src homology 2 domain-containing transforming protein 1 |
| M20747 | Human insulin-responsive glucose transporter (GLUT4) mRNA; Solute carrier family 2 (facilitated glucose transporter), member 4 |
| NM_001043 | *Homo sapiens* solute carrier family 6 (neurotransmitter transporter, noradrenalin), member 2 (SLC6A2) |
| NM_000454 | *Homo sapiens* superoxide dismutase 1, soluble (amyotrophic lateral sclerosis 1 (adult)) (SOD1); Superoxide dismutase 1, soluble (amyotrophic lateral sclerosis 1 (adult)) |
| X07834 | Human mRNA for manganese superoxide dismutase; Superoxide dismutase 2, mitochondrial |
| J02947 | Human extracellular-superoxide dismutase (SOD3) mRNA; Superoxide dismutase 3, extracellular |
| L13858 | Human guanine nucleotide exchange factor mRNA, complete cds, SOS1, Sons of Sevenless |
| M60618 | Human nuclear autoantigen (SP-100) mRNA |
| NM_000582 | *Homo sapiens* secreted phosphoprotein 1 (osteopontin, bone sialoprotein I, early T-lymphocyte activation 1) (SPP1) |

TABLE 33-continued

| | |
|---|---|
| U83867 | Human alpha II spectrin mRNA, Fodrin |
| J03161 | Human serum response factor (SRF) mRNA; Serum response factor (c-fos serum response element-binding transcription factor) |
| D86640 | *Homo sapiens* mRNA for stac, (src homology three (SH3) and cysteine rich domain) |
| M97935 | *Homo sapiens* transcription factor ISGF-3 mRNA, complete cds |
| M97934 | *Homo sapiens* interferon alpha induced transcriptional activator (ISGF-3) mRNA sequence |
| L29277 | *Homo sapiens* DNA-binding protein (APRF) mRNA, complete cds |
| L78440 | *Homo sapiens* STAT4 mRNA, complete cds |
| L41142 | *Homo sapiens* signal transducer and activator of transcription (STAT5) mRNA |
| U16031 | Human transcription factor IL-4 Stat mRNA, complete cds |
| U04735 | Human microsomal stress 70 protein ATPase core (stch) mRNA; Stress 70 protein chaperone, microsome-associated, 60 kD |
| U26424 | Human Ste20-like kinase (MST2) mRNA; Serine/threonine kinase 3 (Ste20, yeast homolog) |
| U60207 | Human stress responsive serine/threonine protein kinase Krs-2 mRNA, Serine/threonine kinase 4 |

TABLE 34

| | |
|---|---|
| L28824 | *Homo sapiens* protein tyrosine kinase (Syk) mRNA; Spleen tyrosine kinase |
| U49928 | *Homo sapiens* TAK1 binding protein (TAB1) mRNA, complete cds |
| U63830 | Human TRAF family member-associated NF-kB activator TANK mRNA, I-TRAF |
| M57732 | Human hepatic nuclear factor 1 (TCF1) mRNA |
| M83233 | *Homo sapiens* transcription factor (HTF4) mRNA, complete cds |
| U08336 | Human basic helix-loop-helix transcription factor mRNA, complete cds |
| D89928 | *Homo sapiens* HKL1 mRNA, complete cds |

TABLE 35

| | |
|---|---|
| NM_007109 | *Homo sapiens* transcription factor 19 (SC1) (TCF19), mRNA |
| X58840 | Human mRNA for variant hepatic nuclear factor 1 (vHNF1), TCF2 |
| U19345 | *Homo sapiens* AR1 (TCF20) mRNA, partial cds |
| AF047419 | *Homo sapiens* epicardin mRNA, complete cds. |
| M31523 | Human transcription factor (E2A) mRNA, complete cds |
| NM_003199 | *Homo sapiens* transcription factor 4 (TCF4) |
| M62810 | Human mitochondrial transcription factor 1 mRNA |
| NM_003202 | *Homo sapiens* transcription factor 7 (T-cell specific, HMG-box) (TCF7) mRNA. |
| Y11306 | *Homo sapiens* mRNA for hTCF-4 |
| D15050 | Human mRNA for transcription factor AREB6; Transcription factor 8 (represses interleukin 2 expression) |
| D43642 | Human YL-1 mRNA for YL-1 protein (nuclear protein with DNA-binding ability), complete cds |
| AB012124 | *Homo sapiens* TCFL5 mRNA for transcription factor-like 5, complete cds |
| NM_003212 | *Homo sapiens* teratocarcinoma-derived growth factor 1 (TDGF1) mRNA |
| L23959 | *Homo sapiens* E2F-related transcription factor (DP-1) mRNA, complete cds. |
| NM_003227 | *Homo sapiens* transferrin receptor 2 (TFR2), mRNA |
| X01060 | Human mRNA for transferrin receptor |
| X70340 | *H. sapiens* mRNA for transforming growth factor alpha |
| X02812 | Human transforming growth factor-beta (TGF-beta; TGFB) |

TABLE 35-continued

| | |
|---|---|
| M19154 | Human transforming growth factor-beta-2 mRNA; glioblastoma -derived T-cell suppressor factor (G-TSF); bsc-1 cell growth inhibitor; polyergin; cetermin |
| J03241 | Human transforming growth factor-beta 3 (TGF-beta3) mRNA, complete cds. |
| L11695 | Human activin receptor-like kinase (ALK-5) mRNA, complete cds |
| D50683 | *Homo sapiens* mRNA for TGF-betaIIR alpha, complete cds |
| L07594 | Human transforming growth factor-beta type III receptor (TGF-beta) mRNA, complete cds |
| NM_000360 | *Homo sapiens* tyrosine hydroxylase (TH), mRNA |
| L33410 | Human c-mpl ligand (ML) mRNA, complete cds |
| NM_006288 | *Homo sapiens* Thy-1 cell surface antigen (THY1), mRNA |
| U02571 | Human tissue inhibitor of metalloproteinase-3 precursor (TIMP-3) mRNA, complete cds |

TABLE 36

| | |
|---|---|
| U88540 | *Homo sapiens* Toll-like receptor 1 (TLR1) mRNA, complete cds |
| U88878 | *Homo sapiens* Toll-like receptor 2 (TLR2) mRNA, complete cds |
| U88879 | *Homo sapiens* Toll-like receptor 3 (TLR3) mRNA, complete cds |
| U88880 | *Homo sapiens* Toll-like receptor 4 (TLR4) mRNA, complete cds |
| U88881 | *Homo sapiens* Toll-like receptor 5 (TLR5) mRNA, partial cds. |
| M10988 | Human tumor necrosis factor (TNF) mRNA |
| M59465 | Human tumor necrosis factor alpha inducible protein A20 mRNA complete cds |
| M31165 | Tumor necrosis factor, alpha-induced protein 6 |
| AF016268 | *Homo sapiens* death receptor 5 (DR5) mRNA, Tumor necrosis factor receptor superfamily, member 10b |
| AF016267 | *Homo sapiens* TRAIL receptor 3 mRNA, complete cds |
| AF018253 | *Homo sapiens* receptor activator of nuclear factor-kappa B (RANK) mRNA, complete cds |
| U94332 | Human osteoprotegerin (OPG) mRNA, complete cds |
| U74611 | Human Apo-3 mRNA; Tumor necrosis factor receptor superfamily, member 12 (translocating chain-association membrane protein) |
| NM_001192 | *Homo sapiens* tumor necrosis factor receptor superfamily, member 17 (TNFRSF17), mRNA |
| X55313 | *H. sapiens* TNF-R mRNA for tumor necrosis factor receptor type 1. |
| M32315 | Human tumor necrosis factor receptor mRNA, TNF R2 |
| X75962 | *H. sapiens* mRNA for 0X40 homologue |
| X60592 | Human CDw40 mRNA for nerve growth factor receptor-related B-lymphocyte activation molecule; CD40 |
| X63717 | *H. sapiens* mRNA for APO-1 cell surface antigen, FAS |
| M83554 | *H. sapiens* lymphocyte activation antigen CD30 mRNA, complete cds |
| L12964 | Human activation dependent T cell mRNA, complete cds |
| U37518 | Human TNF-related apoptosis inducing ligand TRAIL mRNA, complete cds |
| AF053712 | *Homo sapiens* osteoprotegerin ligand mRNA, complete cds |

TABLE 37

| | |
|---|---|
| AF039390 | *Homo sapiens* vascular endothelial cell growth inhibitor (VEGI) mRNA, partial cds |
| D90224 | Human mRNA for glycoprotein 34 (gp34). |
| L07414 | Human CD40-ligand mRNA (Tumor necrosis factor (ligand) superfamily, member 5); CD40L |
| D38122 | Human mRNA for Fas ligand, complete cds; FasL |
| L09753 | *Homo sapiens* CD30 ligand mRNA, complete cds. |
| U03398 | Human receptor 4-1BB ligand mRNA, complete cds |

TABLE 37-continued

| | |
|---|---|
| M14695 | Human p53 cellular tumor antigen mRNA, complete cds |
| U58334 | Human Bcl2, p53 binding protein Bbp/53BP2 (BBP/53BP2) mRNA |
| NM_005427 | *Homo sapiens* tumor protein p73 (TP73) mRNA: Human p73 (monoallelically expressed p53-related protein) |
| X02592 | Human mRNA for T-cell receptor alpha chain (TCR-alpha). |
| L41690 | *Homo sapiens* TNF receptor-1 associated protein (TRADD) mRNA, 3' end of cds |
| NM_005658 | *Homo sapiens* TNF receptor-associated factor 1 (TRAF1) mRNA. |
| U12597 | Human tumor necrosis factor type 2 receptor associated protein (TRAP3) mRNA, complete cds |
| NM_003300 | *Homo sapiens* TNF receptor-associated factor 3 (TRAF3) mRNA. |
| X80200 | *H. sapiens* MLN62 mRNA (TNF receptor-associated factor 4) |
| AB000509 | *Homo sapiens* mRNA for TRAF5, complete cds |
| U78798 | Human TNF receptor associated factor 6 (TRAF6) mRNA, complete cds |
| AF043254 | *Homo sapiens* heat shock protein 75 (hsp75) mRNA, partial cds (tumor necrosis factor type 1 receptor associated protein) |
| M12886 | Human T-cell receptor active beta-chain mRNA, complete cds |
| U35048 | Human putative regulatory protein TGF-beta-stimulated clone 22 homolog (TSC22) |
| NM_000549 | *Homo sapiens* thyroid stimulating hormone, beta (TSHB) |
| NM_000369 | *Homo sapiens* thyroid stimulating hormone receptor (TSHR) |
| X54637 | Human tyk2 mRNA for non-receptor protein tyrosine kinase; Tyrosine kinase 2 |
| M26880 | Human ubiquitin mRNA, complete cds |
| AF016371 | *Homo sapiens* U-snRNP-associated cyclophilin (USA-CyP) mRNA, complete cds |
| NM_001078 | *Homo sapiens* vascular cell adhesion molecule 1 (VCAM1) |
| M32977 | Human heparin-binding vascular endothelial growth factor (VEGF) mRNA |
| U48801 | Human vascular endothelial growth factor B precursor (VEGFB) |

TABLE 38

| | |
|---|---|
| U43142 | Human vascular endothelial growth factor related protein VRP mRNA vascular endothelial growth factor C precursor (VEGF-C); FLT4 ligand |
| U10564 | Human CDK tyrosine 15-kinase WEE1Hu (Wee1Hu) mRNA, complete cds. |
| AF100779 | *Homo sapiens* connective tissue growth factor related protein WISP-1 (WISP1) mRNA, complete cds |
| AF100780 | *Homo sapiens* connective tissue growth factor related protein WISP-2 (WISP2) mRNA, complete cds. |
| AF100781 | *Homo sapiens* connective tissue growth factor related protein WISP-3 (WISP3) mRNA, complete cds. |
| U81787 | Human Wnt10B mRNA, complete cds |
| Y12692 | *Homo sapiens* mRNA for WNT11 gene |
| X07876 | Human mRNA for irp protein (int-1 related protein) Wingless-type MMTV integration site family member 2 |
| Z71621 | *H. sapiens* Wnt-13 mRNA |
| U53476 | Human proto-oncogene Wnt7a mRNA, complete cds. |
| Y11094 | *H. sapiens* mRNA for WNT-8B protein |
| L20422 | Human 14-3-3n protein mRNA; Tyrosine 3-monooxygenase/tryptophan 5-monooxygenase activation protein, eta polypeptide |
| M86400 | Human phospholipase A2 mRNA, complete cds |
| L05148 | Human protein tyrosine kinase related mRNA sequence; Zeta-chain (TCR) associated protein kinase (70 kD) |

TABLE 39

| | CD3− cell/CD3+ cell | | |
|---|---|---|---|
| Name | ave (n = 3) | stdev | CV (%) |
| ABCC3 | 21.92 | 8.05 | 36.73 |
| LYN | 14.90 | 0.09 | 40.15 |
| PTGS1 | 14.66 | 8.94 | 0.58 |
| CDKN1C | 14.00 | 11.98 | 85.57 |
| FLT3 | 13.91 | 7.16 | 51.49 |
| FCER1G | 13.20 | 12.96 | 91.63 |
| CHUK | 11.63 | 3.76 | 32.30 |
| VEGFC | 10.80 | 4.31 | 39.92 |
| POLK | 10.65 | 10.14 | 95.21 |
| AVPR1A | 10.22 | 6.37 | 62.29 |
| CYP7A1 | 9.66 | 2.67 | 27.70 |
| PRKCBP2 | 9.62 | 9.49 | 98.70 |
| GNG11 | 8.14 | 4.24 | 52.03 |
| GNAZ | 8.06 | 2.92 | 36.17 |
| AVPR2 | 7.72 | 5.35 | 69.27 |
| CD9 | 7.62 | 1.50 | 19.69 |
| GJB3 | 7.49 | 4.21 | 79.72 |
| DTR | 7.39 | 2.97 | 40.21 |
| HLA-DRB1 | 7.31 | 4.82 | 81.16 |
| RPC32 | 7.30 | 5.82 | 79.79 |
| NRG1 | 7.25 | 2.92 | 61.00 |
| MAFG | 7.19 | 3.82 | 29.64 |
| MGST2 | 6.95 | 3.36 | 48.37 |
| RAB13 | 6.75 | 2.38 | 22.94 |
| SLC7A7 | 6.38 | 1.63 | 25.63 |
| CYP1B1 | 6.36 | 3.18 | 50.01 |
| IL6 | 6.07 | 2.06 | 33.91 |
| PDGFA | 6.07 | 2.96 | 48.81 |
| MYCL1 | 6.06 | 3.14 | 30.99 |
| FES | 6.04 | 4.23 | 70.04 |
| TNFRSF1B | 5.86 | 3.74 | 63.82 |
| IPF1 | 5.79 | 5.75 | 99.45 |
| YWHAH | 5.46 | 1.61 | 29.41 |
| PIG3 | 5.31 | 2.78 | 67.68 |
| BTK | 5.26 | 2.92 | 55.53 |
| E2F3 | 5.00 | 2.52 | 50.53 |
| FCGR2B | 4.92 | 1.53 | 44.29 |
| UGT2B7 | 4.72 | 2.70 | 40.31 |
| ATP1B4 | 4.66 | 3.77 | 81.02 |
| PENK | 4.63 | 0.82 | 17.65 |
| BAG4 | 4.60 | 1.53 | 85.30 |
| PLA2G4A | 4.48 | 2.87 | 64.04 |
| TLR4 | 4.46 | 0.89 | 19.95 |
| FGR | 4.32 | 0.93 | 33.34 |
| ALDH1 | 4.22 | 2.58 | 61.08 |
| NOS1 | 4.21 | 2.74 | 65.02 |
| TLR5 | 4.14 | 1.23 | 51.76 |
| ABCC1 | 4.09 | 2.77 | 78.31 |
| ALDH2 | 4.08 | 3.04 | 65.86 |
| ARHGAP6 | 4.08 | 0.86 | 21.04 |
| IL1R2 | 3.88 | 1.88 | 57.22 |
| SOD2 | 3.76 | 0.66 | 17.57 |
| NR1H4 | 3.66 | 1.59 | 43.29 |
| TCF4 | 3.65 | 0.90 | 95.77 |
| SKIL | 3.42 | 0.71 | 20.79 |
| IL8RA | 3.41 | 0.72 | 74.47 |
| POU2F2 | 3.36 | 0.77 | 49.91 |
| CDC25C | 3.33 | 1.34 | 42.41 |
| PAK1 | 3.28 | 1.25 | 37.96 |
| SLC1A4 | 3.19 | 0.69 | 21.61 |
| SLC1A3 | 3.15 | 0.72 | 22.93 |
| BRAF | 3.13 | 0.07 | 2.37 |
| ATF3 | 3.11 | 0.46 | 14.66 |
| TRA@ | 15.08 | 11.13 | 73.78 |
| CD3G | 12.03 | 1.36 | 11.32 |
| CD3E | 10.55 | 1.10 | 10.39 |
| IL7R | 9.77 | 6.15 | 62.90 |
| BCL2 | 9.54 | 2.88 | 30.18 |
| PCNA | 8.14 | 4.35 | 53.41 |
| HSPA10 | 7.52 | 3.62 | 48.14 |
| EPHX2 | 7.04 | 2.33 | 33.07 |
| CD8B1 | 6.97 | 3.98 | 57.03 |
| FYN | 6.97 | 0.97 | 13.87 |
| STAT1 | 6.44 | 3.54 | 54.87 |
| HSPF1 | 6.44 | 0.87 | 13.55 |

TABLE 39-continued

CD3− cell/CD3+ cell

| Name | ave (n = 3) | stdev | CV (%) |
|---|---|---|---|
| CCR5 | 5.63 | 2.43 | 43.20 |
| ELF1 | 5.33 | 3.42 | 64.21 |
| NR3C2 | 5.22 | 4.78 | 91.53 |
| TGFBR2 | 5.01 | 2.88 | 57.45 |
| ATRX | 4.65 | 2.49 | 53.64 |
| HLJ1 | 4.64 | 3.41 | 73.62 |
| CYP2J2 | 4.58 | 1.29 | 28.22 |
| E2F4 | 4.44 | 1.96 | 44.28 |
| STAT4 | 4.35 | 4.75 | 108.99 |
| NFATC3 | 4.26 | 2.62 | 61.62 |
| PIK3R1 | 4.17 | 1.23 | 29.47 |
| PPP3CB | 4.12 | 2.00 | 48.48 |
| CLK1 | 4.11 | 4.04 | 98.37 |
| RBL2 | 3.76 | 2.16 | 57.55 |
| KIAA0194 | 3.75 | 0.91 | 24.32 |
| GSTM3 | 3.75 | 2.21 | 58.89 |
| GZMA | 3.74 | 4.32 | 115.44 |
| CDC25B | 3.70 | 0.50 | 13.54 |
| KRAS2 | 3.65 | 0.98 | 26.90 |
| ITGA4 | 3.49 | 1.62 | 46.24 |
| IL13RA2 | 3.48 | 2.01 | 57.64 |
| SOD1 | 3.47 | 0.21 | 6.20 |
| CCNG1 | 3.38 | 1.25 | 36.86 |
| PAP | 3.30 | 0.87 | 26.40 |
| ABCE1 | 3.27 | 0.48 | 14.75 |
| TNFRSF1 | 3.25 | 1.01 | 30.96 |
| CHST5 | 3.19 | 2.34 | 73.37 |
| STAC | 3.16 | 2.62 | 82.98 |
| ATP1A3 | 3.14 | 0.87 | 27.84 |
| HINT | 3.14 | 1.49 | 47.46 |
| ABCC5 | 3.12 | 1.06 | 34.01 |
| TAF1B | 3.11 | 1.33 | 42.84 |
| CD80 | 3.10 | 0.20 | 6.29 |
| CD28 | 3.10 | 0.94 | 30.25 |
| STCH | 3.08 | 0.86 | 27.91 |
| TTF1 | 3.07 | 0.73 | 23.81 |
| POLR2C | 3.05 | 1.49 | 48.89 |
| HGF | 3.01 | 1.37 | 45.36 |

TABLE 40

| Name of gene | t value | p value |
|---|---|---|
| ABCE1 | −24.009 | 0.000071 |
| IFNB1 | −16.646 | 0.000298 |
| BMI1 | −15.039 | 0.000443 |
| KRAS2 | −14.382 | 0.000527 |
| CD80 | −14.224 | 0.000550 |
| IL8RA | 13.916 | 0.000598 |
| BAG4 | 13.105 | 0.000754 |
| POLK | 13.054 | 0.000766 |
| NFATC2 | −12.400 | 0.000933 |
| NRG1 | 12.049 | 0.001041 |
| TLR5 | 11.925 | 0.001083 |
| HGF | −10.946 | 0.001501 |
| POLI | −10.621 | 0.001682 |
| CDC25B | −10.463 | 0.001780 |
| IL6 | 10.452 | 0.001787 |
| SELE | −10.449 | 0.001789 |
| MAX | 10.384 | 0.001832 |
| FCGR2B | 10.296 | 0.001891 |
| COX10 | −10.208 | 0.001953 |
| YWHAH | 10.138 | 0.002005 |
| ADH6 | 9.976 | 0.002130 |
| PRKCZ | −9.925 | 0.002171 |
| AVPR2 | 9.872 | 0.002215 |
| GJB3 | 9.808 | 0.002269 |
| CLK2 | −9.694 | 0.002371 |
| TRA@ | −9.543 | 0.002514 |
| EPHX2 | −9.540 | 0.002517 |
| CD3G | −9.441 | 0.002617 |
| MAP2K6 | −9.413 | 0.002646 |
| ALDH1 | 9.196 | 0.002886 |
| PCNA | −9.134 | 0.002959 |
| CD3E | −9.131 | 0.002962 |

What is claimed is:

1. An oligonucleotide array comprising multiple subblock regions and oligonucleotides of different genes positioned to each of said multiple subblock regions, each of said multiple subblock regions having oligonucleotides positioned thereon based on at least one of gene function and gene expression,
wherein said oligonucleotides within a subblock region are positioned according to an arrangement pattern, said pattern being an arrangement of oligonucleotides of the different genes,
wherein the arrangement is formed from at least oligonucleotides of genes associated with each other at a first predetermined correlation degree being positioned closer to each other than oligonucleotides of genes associated with each other at a second predetermined correlation degree which is lower than the first correlation degree, and
wherein a correlation degree between oligonucleotides of genes associated with each other is based on a classification algorithm using at least one of significant probability value (P value), fluorescent differential display (FDD) and a classification algorithm of a supervised method.

2. The oligonucleotide array according to claim 1, wherein said oligonucleotides are derived from genes related to a particular phenotype.

3. The oligonucleotide array according to claim 2, wherein said phenotype is related to psychological stress response.

4. The oligonucleotide array according to claim 3, wherein said oligonucleotides are derived from one of the following: stress tolerance or survival related genes and hormonal genes, and stress tolerance related transcription factors and signaling molecules.

5. The oligonucleotide array according to claim 1 wherein said correlation degrees are those determined in a database.

6. The oligonucleotide array according to claim 5 wherein said correlation degrees are determined by one or a combination of two or more of gene interrelationship score, pairwise information of ligand and receptor, protein-protein interaction information, and gene passway information.

7. The oligonucleotide array according to claim 1, wherein a correlation degree is statistically calculated from an expression amount of oligonucleotides of genes as determined from experimental results using samples for comparison.

8. The oligonucleotide array according to claim 7, wherein said samples to be compared comprise samples from patients with a particular disease and samples from healthy subjects.

* * * * *